United States Patent
Lv et al.

(10) Patent No.: US 9,809,572 B2
(45) Date of Patent: Nov. 7, 2017

(54) DEUTERATED DIAMINOPYRIMIDINE COMPOUNDS AND PHARMACEUTICAL COMPOSITIONS COMPRISING SUCH COMPOUNDS

(71) Applicant: Suzhou Zelgen Biopharmaceuticals Co., Ltd., Jiangsu (CN)

(72) Inventors: Binhua Lv, Jiangsu (CN); Chengwei Li, Jiangsu (CN); Benwen Cao, Jiangsu (CN); Xudong Pang, Jiangsu (CN)

(73) Assignee: Suzhou Zelgen Biopharmaceuticals Co., Ltd., Jiangsu (CN)

( * ) Notice: Subject to any disclaimer, the term of this patent is extended or adjusted under 35 U.S.C. 154(b) by 0 days.

(21) Appl. No.: 14/786,069

(22) PCT Filed: Apr. 22, 2014

(86) PCT No.: PCT/CN2014/075958
§ 371 (c)(1),
(2) Date: Feb. 16, 2016

(87) PCT Pub. No.: WO2014/173291
PCT Pub. Date: Oct. 30, 2014

(65) Prior Publication Data
US 2016/0185753 A1    Jun. 30, 2016

(30) Foreign Application Priority Data

Apr. 22, 2013 (CN) .......................... 2013 1 0141192

(51) Int. Cl.
*C07D 401/12* (2006.01)
*C07D 211/26* (2006.01)
*C07D 239/42* (2006.01)

(52) U.S. Cl.
CPC .......... *C07D 401/12* (2013.01); *C07D 211/26* (2013.01); *C07D 239/42* (2013.01); *C07B 2200/13* (2013.01)

(58) Field of Classification Search
CPC ... C07D 401/12; C07D 211/26; C07D 239/42
See application file for complete search history.

(56) References Cited

U.S. PATENT DOCUMENTS 5,846,514 A    12/1998    Foster et al.
8,592,432 B2   11/2013    Chen et al.

2010/0291025 A1 *  11/2010  Rao ................ A61K 31/505
                                              424/85.2
2013/0040957 A1    2/2013   Dhanoa
2013/0296357 A1    11/2013  Li et al.

FOREIGN PATENT DOCUMENTS

| CN | 1148843 A | 4/1997 | |
| CN | 101616895 A | 12/2009 | |
| CN | 102131788 A | 7/2011 | |
| CN | 103458881 A | 12/2013 | |
| WO | 2008073687 A2 | 6/2008 | |
| WO | WO 2008073687 A2 * | 6/2008 | ........... C07D 213/74 |
| WO | 2012106540 A1 | 8/2012 | |

OTHER PUBLICATIONS

T.A. Baillie, Pharmacological Reviews, 33(2), 81-132 (1981).*
International Search Report dated Aug. 4, 2014 in International Application No. PCT/CN2014/075958.

* cited by examiner

*Primary Examiner* — Alexander R Pagano
*Assistant Examiner* — Ebenezer O Sackey
(74) *Attorney, Agent, or Firm* — Panitch Schwarze Belisario & Nadel LLP

(57) ABSTRACT

Deuterated diaminopyrimidine compounds and pharmaceutical compositions containing such compounds are described. In particular, disclosed are deuterated diaminopyrimidine compounds of formula (I), and pharmaceutical compositions containing such compounds or crystal forms, pharmaceutically acceptable salt, hydrates or solvates thereof. The disclosed deuterated diaminopyrimidine compounds can be used for treating and/or preventing protein kinase-associated diseases, such as cell proliferative disease, cancer, immune disease and the like.

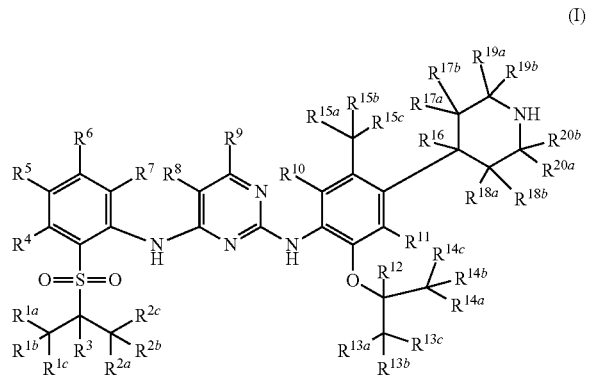

16 Claims, 2 Drawing Sheets

DEUTERATED DIAMINOPYRIMIDINE COMPOUNDS AND PHARMACEUTICAL COMPOSITIONS COMPRISING SUCH COMPOUNDS

CROSS REFERENCE TO RELATED APPLICATION

This application is a Section 371 of International Application No. PCT/CN2014/075958, filed Apr. 22, 2014, which was published in the Chinese language on Oct. 30, 2014, under International Publication No. WO 2014/173291 A1 and the disclosure of which is herein incorporated by reference in its entirety.

FIELD OF THE INVENTION

The present invention relates to the field of pharmaceutics. Specifically, the present invention relates to a new deuterated diamino pyrimidine compound, and pharmaceutical compositions comprising said compound.

BACKGROUND OF THE INVENTION

Anaplastic lymphoma kinase (ALK) is a member of the insulin receptor tyrosine kinase superfamily, ALK fusion protein, mutation and overexpression thereof are associated with various diseases. ALK was firstly discovered in anaplastic large cell lymphoma (ALCL) cell lines, the fusion protein gene formed by translocation of the 2nd and the 5th balanced chromosomal contains the 3' end portion of the ALK gene (including intracellular domain and protein kinase domain) and the nucleolar phosphoprotein gene (Nucleophosmin, NPM gene). Over twenty types of ALK fusion proteins produced by different chromosome rearrangements have been discovered. They participate in the pathogenesis of diseases including anaplastic large cell lymphoma, diffuse large B-cell lymphoma, inflammatory myofibroblastic tumor, neuroblastoma, etc. EML4-ALK fusion protein and other four ALK fusion proteins play a fundamental role in the development of about 5% of non-small cell lung cancer. The downstream signaling pathways involving ALK fusion proteins involves Ras/Raf/MEK/ERK1/2 proliferation module and JAK/STAT cell survival pathway, and this intricate signal transduction network affects cell proliferation, differentiation and apoptosis. ALK kinase inhibitor can be used to treat cancer, autoimmune diseases and the like. In August 2011, Pfizer's selective ALK and c-Met dual inhibitor crizotinib (trade name Xalkori) was approved by the US Food and Drug Administration for the treatment of advanced lung small cell lung cancer. Drug-resistance emerges during the clinical application of Crizotinibs, thereby stimulating the development of second-generation ALK kinase inhibitor drugs, for the treatment of non-small cell lung cancer and other diseases.

Diaminopyrimidine compounds and derivatives thereof are a class of inhibitors for protein kinases such as ALK kinase. A series of diaminopyrimidine derivatives having 2,4-dual-substitutients on pyrimidine ring has been disclosed in WO2008073687 and WO2012106540. Wherein the compound LDK378 (CERITINIB), of which the chemical name is 5-chloro-$N^2$-(2-isopropoxy-5-methyl-4-(piperidin-4-yl)phenyl)-$N^4$-(2-(isopropylsulfonyl)phenyl) pyrimidine-2,4-diamine, is a selective ALK kinase inhibitor, and it can be used in the treatment of cancer and cell proliferative diseases and other related diseases. At present, the compound is in the Phase II clinical trials of treating cell proliferative diseases (such as non-small cell lung cancer).

Although the targeted inhibition of different protein kinases is beneficial for the treatment of various kinase-related diseases, the discovery of novel compounds which specifically inhibit some protein kinase and has good drug-gability such as oral bioavailability is still very challenging. In addition, there are some side effects and drug resistance problems forh some currently available protein kinase inhibitors.

Thus, there is still a need in the art to develop compounds having kinases (e.g., ALK kinases) inhibitory activity or better pharmacodynamic/pharmacokinetics properties.

SUMMARY OF THE INVENTION

The object of the present invention is to provide a type of novel compounds having ALK kinases inhibitory activity and/or better pharmacodynamic/pharmacokinetics properties, and uses thereof.

In the first aspect of the present invention, a deuterated diaminopyrimidine compound of formula (I), or a crystal form, pharmaceutically acceptable salt, hydrate or solvate thereof is provided:

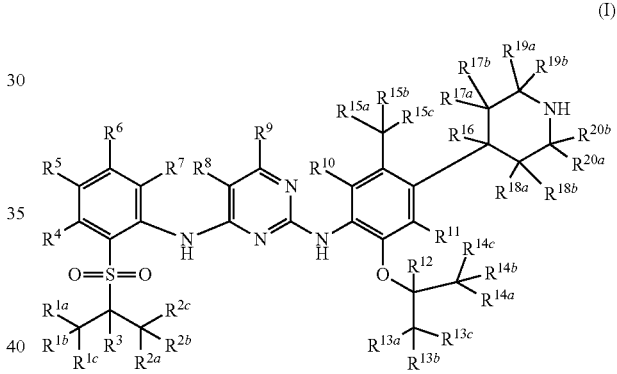

(I)

Wherein $R^{1a}$, $R^{1b}$, $R^{1c}$, $R^{2a}$, $R^{2b}$, $R^{2c}$, $R^3$, $R^4$, $R^5$, $R^6$, $R^7$, $R^9$, $R^{10}$, $R^{11}$, $R^{12}$, $R^{13a}$, $R^{13b}$, $R^{13c}$, $R^{14a}$, $R^{14b}$, $R^{14c}$, $R^{15a}$, $R^{15b}$, $R^{15c}$, $R^{16}$, $R^{17a}$, $R^{17b}$, $R^{18a}$, $R^{18b}$, $R^{19a}$, $R^{19b}$, $R^{20a}$ and $R^{20b}$ are independently hydrogen, deuterium or halogen;

$R^8$ is hydrogen, deuterium, halogen, cyano, undeuterated C1-C6 alkyl or C1-C6 alkoxy, one- or multiple-deuterated or per-deuterated C1-C6 alkyl or C1-C6 alkoxy, or one- or multiple-halogenated or per-halogenated C1-C6 alkyl or C1-C6 alkoxy;

with the proviso that at least one of $R^{1a}$, $R^{1b}$, $R^{1c}$, $R^{2a}$, $R^{2b}$, $R^{2c}$, $R^3$, $R^4$, $R^5$, $R^6$, $R^7$, $R^9$, $R^{10}$, $R^{11}$, $R^{12}$, $R^{13a}$, $R^{13b}$, $R^{13c}$, $R^{14a}$, $R^{14b}$, $R^{14c}$, $R^{15a}$, $R^{15b}$, $R^{15c}$, $R^{16}$, $R^{17a}$, $R^{17b}$, $R^{18a}$, $R^{18b}$, $R^{19a}$, $R^{19b}$, $R^{20a}$ or $R^{20b}$ is deuterated or deuterium.

In another preferred embodiment, the deuterium isotope content at the deuterium-substituted position is at least greater than natural isotopic deuterium content (about 0.015%), preferably greater than 30%, more preferably greater than 50%, more preferably greater than 75%, more preferably greater than 95%, more preferably greater than 99%.

In another preferred embodiment, the compound of formula (I) contains at least one deuterium atom, more preferably two deuterium atoms, more preferably four deuterium atoms, more preferably 6 deuterium atoms.

In another preferred embodiment, $R^{1a}$, $R^{1b}$, $R^{1c}$, $R^{2a}$, $R^{2b}$, $R^{2c}$ and $R^3$ are independently hydrogen or deuterium.

In another preferred embodiment, $R^{12}$, $R^{13a}$, $R^{13b}$, $R^{13c}$, $R^{14a}$, $R^{14b}$ and $R^{14c}$ are independently hydrogen or deuterium.

In another preferred embodiment, $R^{15a}$, $R^{15b}$ and $R^{15c}$ are independently hydrogen or deuterium.

In another preferred embodiment, $R^{16}$, $R^{17a}$, $R^{17b}$, $R^{18a}$, $R^{18b}$, $R^{19a}$, $R^{19b}$, $R^{20a}$ and $R^{20b}$ are independently hydrogen or deuterium.

In another preferred embodiment, each $R^8$ is independently selected from: halogen, cyno, one- or multiple-deuterated or per-deuterated methyl or methoxyl, or trifluoromethyl.

In another preferred embodiment, $R^3$ is deuterium;

In another preferred embodiment, $R^8$ is chlorine;

In another preferred embodiment, $R^{12}$ is deuterium;

In another preferred embodiment, $R^{15a}$, $R^{15b}$ and $R^{15c}$ are deuterium;

In another preferred embodiment, $R^{19a}$, $R^{19b}$, $R^{20a}$ and $R^{20b}$, are deuterium;

In another preferred embodiment, the compound is one of the following compounds, or a pharmaceutical acceptable salt thereof:

5-chloro-$N^2$-(2-isopropoxy-5-methyl-4-(piperidin-4-yl)phenyl)-$N^4$-(2-((2-d-prop-2-yl)sulfon yl)phenyl)pyrimidine-2,4-diamine;

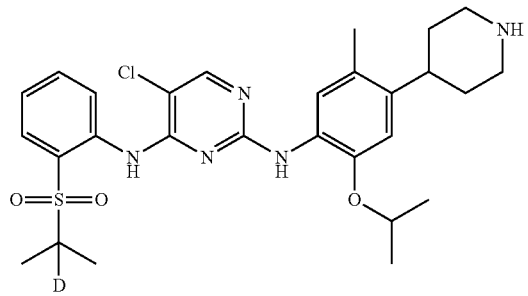 [SMILES: [2H]C(C)(C)S(=O)(=O)c1ccccc1Nc1nc(Nc2cc(C)c(C3CCNCC3)cc2OC(C)C)ncc1Cl]

5-chloro-$N^2$-(2-isopropoxy-5-methyl-4-(piperidin-4-yl)phenyl)-$N^4$-(2-(($d_7$-isopropyl)sulfonyl)phenyl)pyrimidine-2,4-diamine;

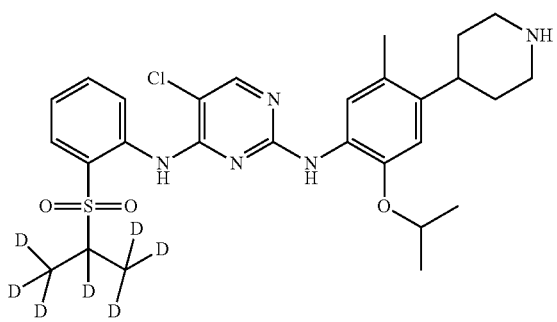 [SMILES: [2H]C([2H])([2H])C([2H])(C([2H])([2H])[2H])S(=O)(=O)c1ccccc1Nc1nc(Nc2cc(C)c(C3CCNCC3)cc2OC(C)C)ncc1Cl]

5-chloro-$N^2$-((2-d-prop-2-yloxy)-5-methyl-4-(piperidin-4-yl)phenyl)-$N^4$-(2-(isopropylsulfonyl)phenyl)pyrimidine-2,4-diamine;

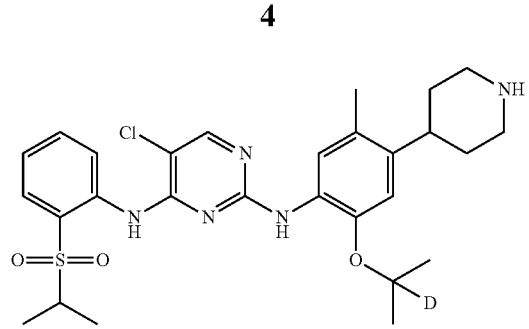

5-chloro-$N^2$-(2-($d_7$-isopropoxy)-5-methyl-4-(piperidin-4-yl)phenyl)-$N^4$-(2-(isopropylsulfonyl)phenyl)pyrimidine-2,4-diamine;

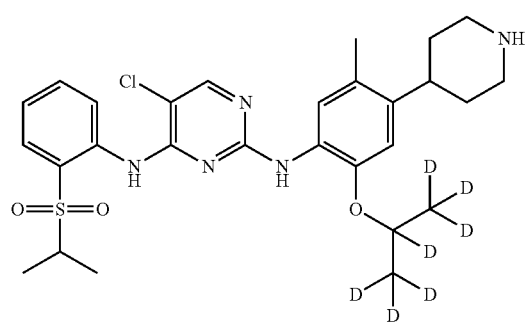 [SMILES: [2H]C([2H])([2H])C([2H])(Oc1cc(C2CCNCC2)c(C)cc1Nc1ncc(Cl)c(Nc2ccccc2S(=O)(=O)C(C)C)n1)C([2H])([2H])[2H]]

5-chloro-$N^2$-(2-isopropoxy-5-($d_3$-methyl)-4-(piperidin-4-yl)phenyl)-$N^4$-(2-(isopropylsulfonyl) phenyl)pyrimidine-2,4-diamine;

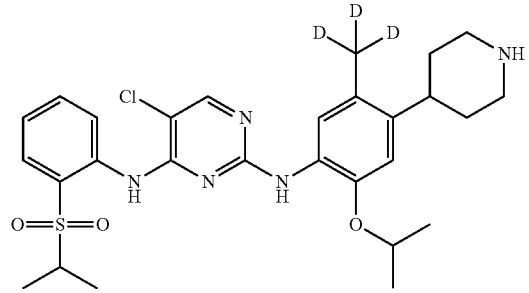 [SMILES: [2H]C([2H])([2H])c1cc(Nc2ncc(Cl)c(Nc3ccccc3S(=O)(=O)C(C)C)n2)c(OC(C)C)cc1C1CCNCC1]

5-chloro-$N^2$-(2-isopropoxy-5-methyl-4-(4-d-piperidin-4-yl)phenyl)-$N^4$-(2-(isopropylsulfonyl) phenyl) pyrimidine-2,4-diamine;

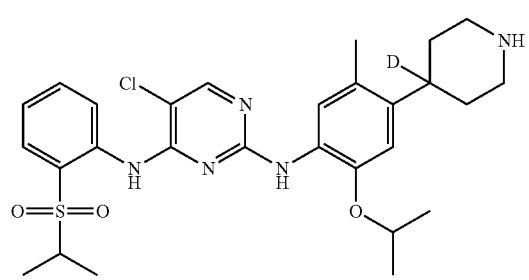 [SMILES: [2H]C1(c2cc(OC(C)C)c(Nc3ncc(Cl)c(Nc4ccccc4S(=O)(=O)C(C)C)n3)cc2C)CCNCC1]

5-chloro-$N^2$-(2-isopropoxy-5-methyl-4-(2,2,6,6-$d_4$-piperidin-4-yl)phenyl)-$N^4$-(2-(isopropylsulfonyl) phenyl) pyrimidine-2,4-diamine;

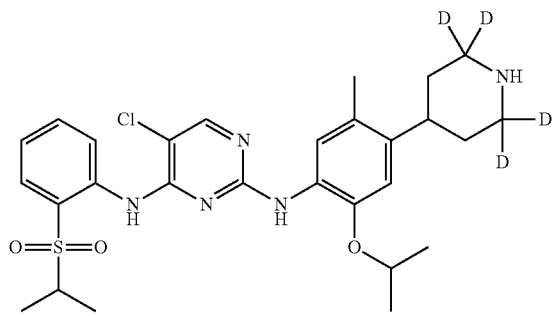 [SMILES: [2H]C1([2H])CC(c2cc(OC(C)C)c(Nc3ncc(Cl)c(Nc4ccccc4S(=O)(=O)C(C)C)n3)cc2C)CC([2H])([2H])N1]

5-chloro-$N^2$-(2-isopropoxy-5-methyl-4-(2,2,4,6,6-$d_5$-piperidin-4-yl)phenyl)-$N^4$-(2-(isopropylsulfonyl) phenyl) pyrimidine-2,4-diamine;

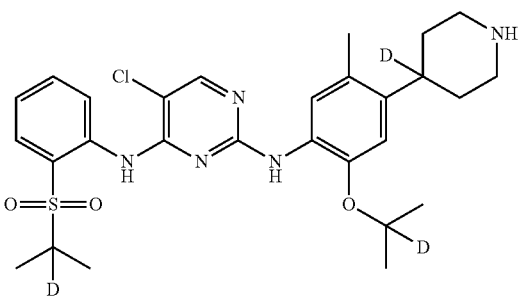

5-chloro-$N^2$-((2-d-prop-2-yloxy)-5-($d_3$-methyl)-4-(4-d-piperin-4-yl)phenyl)-$N^4$-(2-((2-d-prop-2-yl) sulfonyl) phenyl) pyrimidine-2,4-diamine;

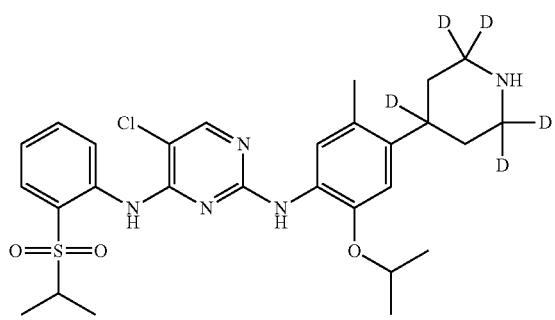 [SMILES: [2H]C1([2H])CC([2H])(c2cc(OC(C)C)c(Nc3ncc(Cl)c(Nc4ccccc4S(=O)(=O)C(C)C)n3)cc2C)CC([2H])([2H])N1]

5-chloro-$N^2$-((2-d-prop-2-yloxy)-5-methyl-4-(piperidin-4-yl)phenyl)-$N^4$-(2-((2-d-prop-2-yl)sulfonyl) phenyl) pyrimidine-2,4-diamine;

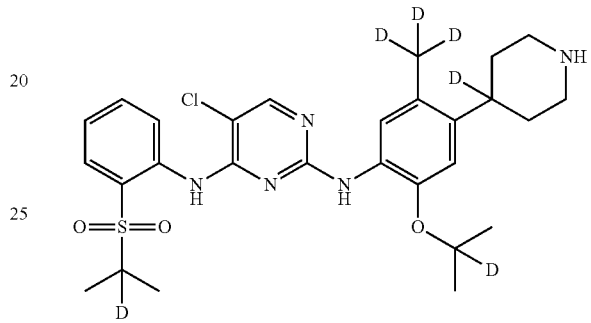

5-chloro-$N^2$-(2-(2-d-Prop-2-yloxy)-5-methyl-4-(2,2,6,6-$d_4$-piperidin-4-yl)phenyl)-$N^4$-(2-((2-d-prop-2-yl) sulfonyl) phenyl) pyrimidine-2,4-diamine;

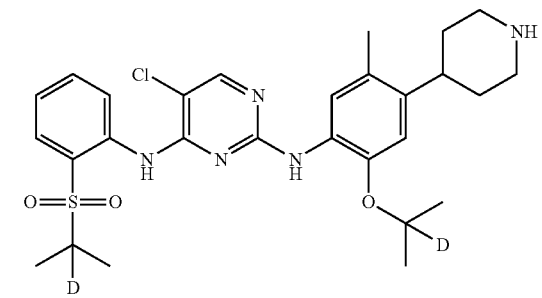 [SMILES: [2H]C(C)(C)Oc1cc(C2CCNCC2)c(C)cc1Nc1ncc(Cl)c(Nc2ccccc2S(=O)(=O)C([2H])(C)C)n1]

5-chloro-$N^2$-(2-($d_7$-isopropoxy)-5-methyl-4-(2,2,6,6-$d_4$-piperidin-4-yl)phenyl)-$N^4$-(2-(($d_7$-isopropyl) sulfonyl) phenyl) pyrimidine-2,4-diamine;

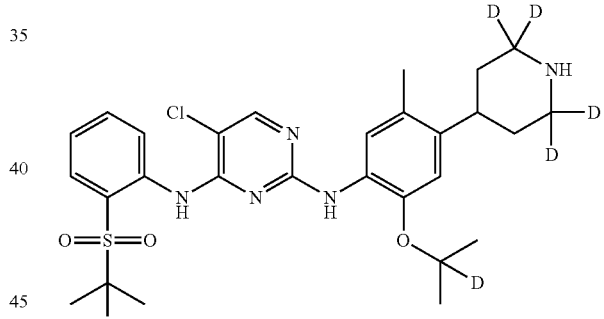

5-chloro-$N^2$-(2-(2-d-prop-2-yloxy)-5-methyl-4-(2,2,4,6,6-$d_5$-piperidin-4-yl)phenyl)-$N^4$-(2-((2-d-prop-2-yl) sulfonyl) phenyl)pyrimidine-2,4-diamine;

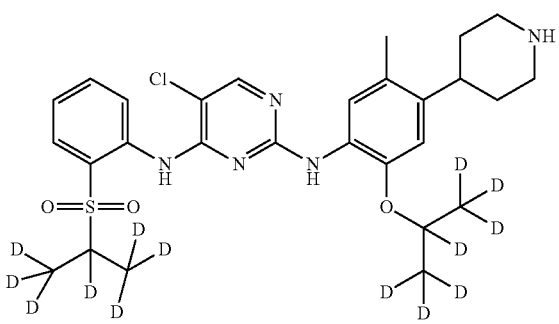 [SMILES: [2H]C([2H])([2H])C([2H])(Oc1cc(C2CCNCC2)c(C)cc1Nc1ncc(Cl)c(Nc2ccccc2S(=O)(=O)C([2H])(C([2H])([2H])[2H])C([2H])([2H])[2H])n1)C([2H])([2H])[2H]]

5-chloro-$N^2$-((2-d-prop-2-yloxy)-5-methyl-4-(4-d-piperidin-4-yl)phenyl)-$N^4$-(2-((2-d-prop-2-yl) sulfonyl) phenyl) pyrimidine-2,4-diamine;

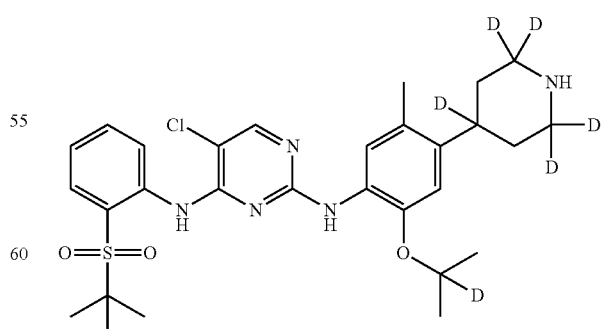

5-chloro-$N^2$-(2-(2-d-prop-2-yloxy)-5-($d_3$-methyl)-4-(2,2,4,6,6-$d_5$-piperidin-4-yl) phenyl)-$N^4$-(2-((2-d-prop-2-yl) sulfonyl) phenyl)pyrimidine-2,4-diamine;

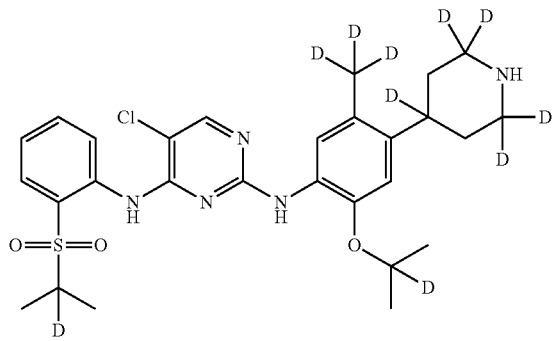 [SMILES: [2H]C1([2H])CC([2H])(c2cc(OC([2H])(C)C)c(Nc3ncc(Cl)c(Nc4ccccc4S(=O)(=O)C([2H])(C)C)n3)cc2C([2H])([2H])[2H])CC([2H])([2H])N1]

5-chloro-N²-(2-(2-d-prop-2-yloxy)-5-methyl-4-(2,2,6,6-d₄-piperidin-4-yl)phenyl)-N⁴-(2-(isopropylsulfonyl) phenyl)pyrimidine-2,4-diamine;

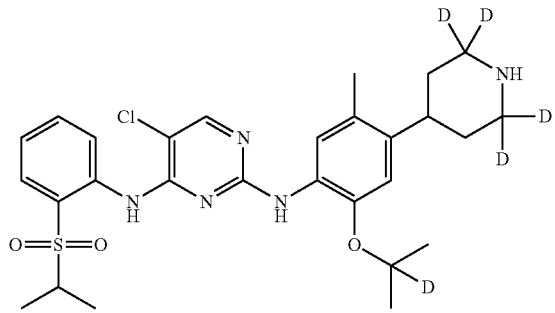 [SMILES: [2H]C1([2H])CC(c2cc(OC([2H])(C)C)c(Nc3ncc(Cl)c(Nc4ccccc4S(=O)(=O)C(C)C)n3)cc2C)CC([2H])([2H])N1]

5-chloro-N²-(2-(2-d-prop-2-yloxy)-5-(d-methyl)-4-(2,2,6,6-d₄-piperidin-4-yl)phenyl)-N⁴-(2-(isopropylsulfonyl) phenyl)pyrimidine-2,4-diamine;

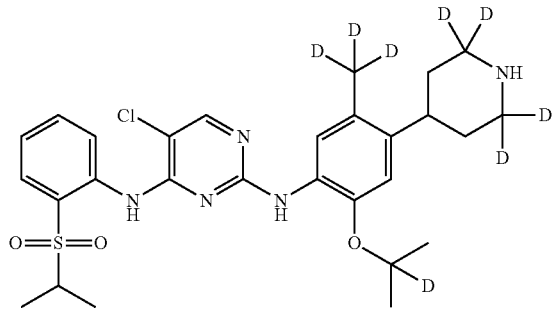 [SMILES: [2H]C1([2H])CC(c2cc(OC([2H])(C)C)c(Nc3ncc(Cl)c(Nc4ccccc4S(=O)(=O)C(C)C)n3)cc2C([2H])([2H])[2H])CC([2H])([2H])N1]

5-chloro-N²-(2-(2-d-prop-2-yloxy)-5-(d₃-methyl)-4-(2,2,4,6,6-d₅-piperidin-4-yl)phenyl)-N⁴-(2-(isopropylsulfonyl) phenyl)pyrimidine-2,4-diamine;

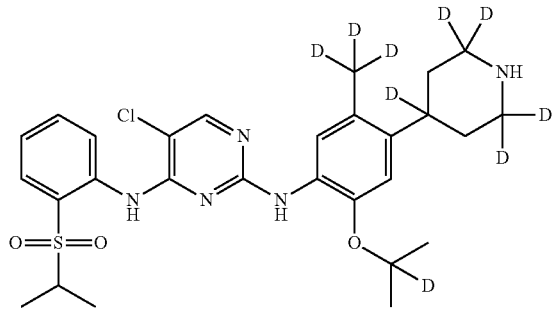 [SMILES: [2H]C1([2H])CC([2H])(c2cc(OC([2H])(C)C)c(Nc3ncc(Cl)c(Nc4ccccc4S(=O)(=O)C(C)C)n3)cc2C([2H])([2H])[2H])CC([2H])([2H])N1]

5-chloro-N²-(2-(2-d-prop-2-yloxy)-5-(d₃-methyl)-4-(2,2,6,6-d₄-piperidin-4-yl)phenyl)-N⁴-(2-((2-d-prop-2-yl) sulfonyl) phenyl)pyrimidine-2,4-diamine;

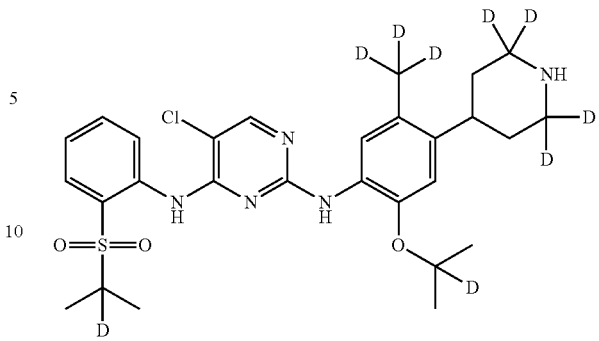

5-chloro-N²-(2-(d₇-isopropoxy)-5-(d₃-methyl)-4-(2,2,4,6,6-d₅-piperidin-4-yl)phenyl)-N⁴-(2-((d₇-isopropyl) sulfonyl) phenyl) pyrimidine-2,4-diamine;

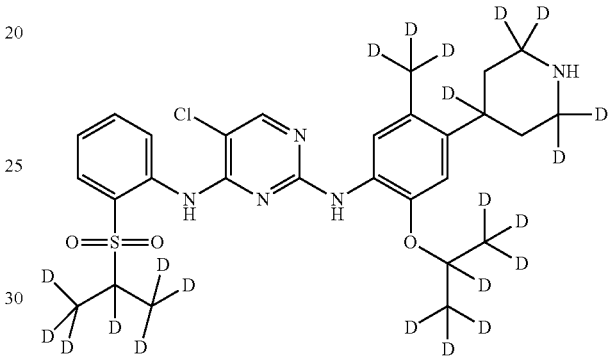

5-chloro-N²-(2-isopropoxy-5-methyl-4-(2,2,4,6,6-d₅-piperdin-4-yl)phenyl)-N⁴-(2-((2-d-prop-2-yl) sulfonyl) phenyl) pyrimidine-2,4-diamine;

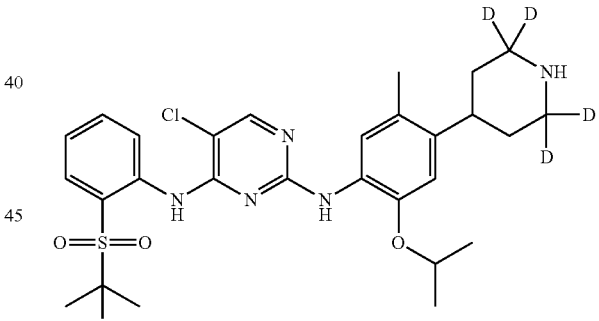

5-chloro-N²-(2-isopropoxy-5-methyl-4-(2,2,4,6,6-d₅-piperidin-4-yl)phenyl)-N⁴-(4-fluoro-2-(isopropylsulfonyl) phenyl) pyrimidine-2,4-diamine;

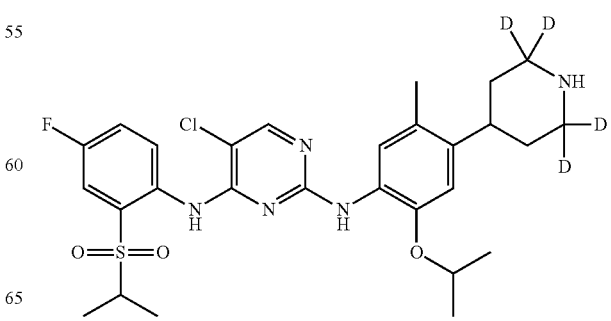

In another preferred embodiment, the compound is

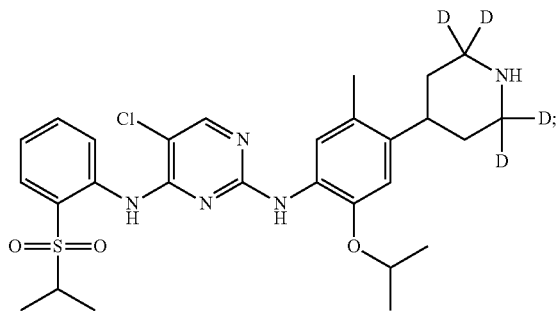

which possesses the following characteristics: MS calculated: 561; MS found: 562 (M+H)+, 584 (M+Na)+.

In another preferred embodiment, the compound is

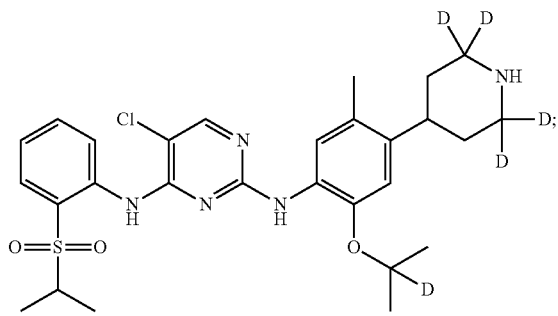

which possesses the following characteristics: MS calculated: 562; MS found: 563 (M+H)+, 585 (M+Na)+.

In another preferred embodiment, the compound is

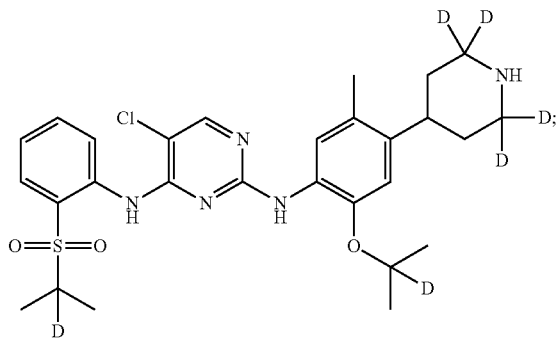

which possesses the following characteristics: MS calculated: 563; MS found: 564 (M+H)+, 586 (M+Na)+.

In another preferred embodiment, the compound is

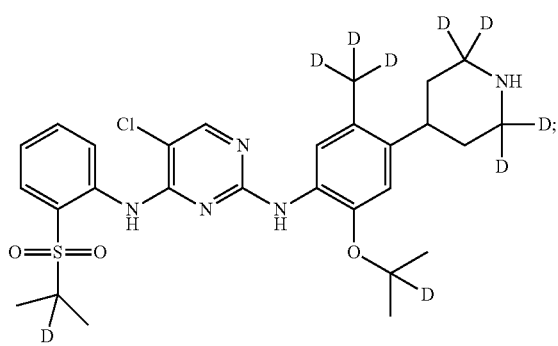

which possesses the following characteristics: MS calculated: 566; MS found: 567 (M+H)+, 589 (M+Na)+.

In another preferred embodiment, the compound is

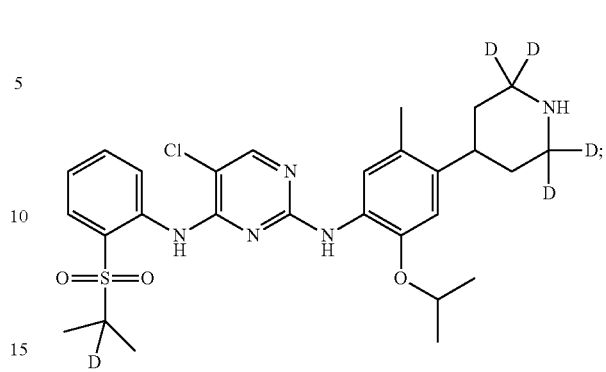

which possesses the following characteristics: MS calculated: 562; MS found: 563 (M+H)+, 585 (M+Na)+.

In another preferred embodiment, undeuterinated compounds are not included in the compound.

In another preferred embodiment, the undeuterated compound is
5-chloro-$N^2$-(2-isopropoxy-5-methyl-4-(piperidin-4-yl)phenyl)-$N^4$-(2-(isopropylsulfonyl)phenyl) pyrimidine-2,4-diamine.

In another preferred embodiment, the compound is prepared by the method described in examples 1-16.

In the second aspect of the present invention, a method of preparing a pharmaceutical composition is provided, which comprises the following step: mixing compounds of the first aspect of the present invention, or a crystal form, pharmaceutically acceptable salt, hydrate or solvate thereof with a pharmaceutically acceptable carrier to form a pharmaceutical composition.

In the third aspect of the present invention, a pharmaceutical composition is provided, which comprises a pharmaceutically acceptable carrier and the compound of the first aspect of the present invention, or a crystal form, pharmaceutically acceptable salt, hydrate or solvate thereof.

In another preferred embodiment, the pharmaceutical composition is an injection, capsule, tablet, pill, powder or granule.

In another preferred embodiment, the pharmaceutical composition comprises other therapeutic medicines, and the other therapeutic medicines are medicines for treating cancers, cell proliferative disorders, cardiovascular diseases, inflammations, infections, autoimmune diseases, viral diseases, or metabolic disorders.

More preferably, the other therapeutic medicine comprises (but not limited to): 5-fluorouracil, FOLFOX, Avastin™ (avastin, bevacizumab), bexarotene, bortezomib, calcitriol, canertinib, capecitabine, gemcitabine, carboplatin, celecoxib, cetuximab, cisplatin, dasatinib, digoxin, enzastaurin, erlotinib, etoposide, everolimus, fulvestrant, gefitinib, genistein, imatinib, irinotecan, lapatinib, lenalidomide, letrozole, leucovorin, matuzumab, oxaliplatin, Taxol (paclitaxel), docetaxel, panitumumab, pegylated granulocyte colony stimulating factor (pegfilgrastin), peglated alfa-interferon, pemetrexed, Polyphenon® E, satraplatin, sirolimus, sunitinib (sutent, sunitinib), sulindac acid (sulindac), Taxotere (taxotere), temozolomide (temodar, temozomolomide), Torisel, temsirolimus, tipifarnib, trastuzumab, valproic acid, vinflunine, Volociximab, Vorinostat, sorafenib, Crizotinib, Lcotinib, lapatinib, Tofacitinib, PD-0332991 (Palbociclib), ambrisentan, CD40 and/or CD154-specific antibodies, fusion proteins, NF-kB inhibitors, nonsteroidal anti-inflammatory drug, clotting factor FXa inhibitors (such as rivaroxaban, etc.), anti-TNF antibodies, antibiotics such as calicheamicin, actinomycin, Adriamycin (doxorubicin) and other prostaglandin drugs or montelukast.

In the fourth aspect of the present invention, a use of the compound of the first aspect of the present invention, or a crystal form, pharmaceutically acceptable salt, hydrate or solvate thereof in the preparation of pharmaceutical compositions that inhibit protein kinases (e.g. ALK kinases) is provided.

In another preferred embodiment, the pharmaceutical composition of the invention can be used to treat the following diseases: cancers, cell proliferative disorders, inflammations, infections, autoimmune diseases, organ transplantations, viral diseases, cardiovascular diseases, or metabolic diseases.

In another preferred embodiment, the cancers include (but are not limited to): lung cancer, head and neck cancer, breast cancer, prostate cancer, esophageal cancer, colorectal cancer, colon cancer, nasopharyngeal cancer, uterine cancer, pancreatic cancer, lymphoma, leukemia, osteosarcoma, melanoma, kidney cancer, stomach cancer, liver cancer, bladder cancer, thyroid cancer or colon cancer.

In another preferred embodiment, the immune diseases or inflammation include (but are not limited to): rheumatoid arthritis, osteoarthritis, rheumatoid spondylitis, gout, asthma, bronchitis, rhinitis, chronic obstructive pulmonary disease, cystic fibrosis disease.

In another preferred embodiment, the cell proliferative disorders include (but are not limited to): lung cancer, head and neck cancer, breast cancer, prostate cancer, esophageal cancer, colorectal cancer, colon cancer, nasopharyngeal cancer, uterine cancer, pancreatic cancer, lymphoma, leukemia, osteosarcoma, melanoma, kidney cancer, stomach cancer, liver cancer, bladder cancer, thyroid cancer or colon cancer.

In another preferred embodiment, the cancer is non-small cell lung cancer.

In the fifth aspect of the present invention, a method of inhibiting protein kinase (e.g. ALK kinases) or a method of treating diseases (such as cancer, cell proliferative disorders, inflammation, infection, immune diseases, organ transplantation, viral disease, cardiovascular diseases or metabolic disease) is provided, comprising the following steps: administering the compound of the first aspect of the present invention, or a crystal form, pharmaceutically acceptable salt, hydrate or solvate thereof, or administering the pharmaceutical composition of the third aspect of the present invention to a subject in need thereof.

It should be understood that, in the present invention, each of the technical features specifically described above and below (such as those in the Examples) can be combined with each other, thereby constituting new or preferred technical solutions which need not be specified again herein.

EMBODIMENTS FOR CARRYING OUT THE INVENTION

Figure 1:
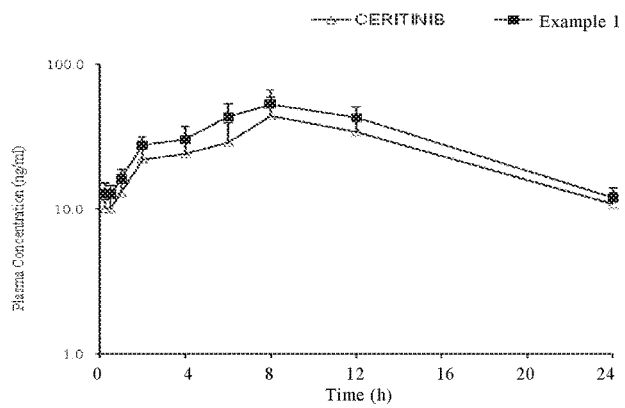
FIG. 1 is a curve of time vs the plasma concentration of compound in male rats respectively administered with 5 mg/kg of control compound CERITINIB and compound of Example 1 by gavage.

Through research, the inventor has unexpectedly discovered that the deuterated diaminopyrimidine compound or pharmaceutically acceptable salts thereof are obviously superior to the undeuterated compound in pharmacokinetic and/or pharmacodynamic properties, which, therefore, are more suitable to be used as ALK kinases inhibitory compounds, and more suitable to be used in the preparation of medicines for treating cancer and diseases associated ALK kinases. The present invention is completed on this basis.

Definitions

As used herein, "halogen" refers to F, Cl, Br, and I. More preferably, the halogen is selected from F, Cl and Br.

As used herein, "C1-C6 alkyl" refers to a straight or branched alkyl which comprises 1 to 6 carbon atoms, such as methyl, ethyl, propyl, isopropyl, butyl, isobutyl, tert-butyl and the like.

As used herein, "C1-C6 alkoxy" refers to a straight or branched alkoxy which comprises 1 to 6 carbon atoms, such as methoxy, ethoxy, propoxy, isopropoxy, butoxy, isobutoxy, tert-butoxy, and the like.

As used herein, "deuterated" means that one or more hydrogen in a compound or group is (are) replaced by deuterium. "Deuterated" may be mono-substituted, di-substituted, multiple-substituted or fully substituted. The term "one- or multiple-deuterated" and "deuterated for one or more times" can be used interchangeably.

As used herein, "undeuterated compound" refers to a compound, the ratio of deuterium atoms of which is not more than the natural isotopic deuterium content (about 0.015%).

In another preferred embodiment, deuterium isotope content at the deuterium substituted position is greater than the natural isotopic deuterium content (0.015%), more preferably greater than 50%, more preferably greater than 75%, more preferably greater than 95%, more preferably greater than 97%, more preferably greater than 99%, more preferably greater than 99.5%.

In another preferred embodiment, the compound of formula (I) contains at least two deuterium atoms, more preferably four deuterium atoms, more preferably six deuterium atoms, more preferably eight deuterium atoms.

In the compound of formula (I), N can be $^{14}N$ and/or $^{15}N$; O can be $^{16}O$ and/or $^{18}O$.

Preferably, in the compound of formula (I), N is $^{14}N$ and/or O is $^{16}O$.

In another preferred embodiment, in the compound, $^{14}N$ isotope content at the nitrogen atom position is ≥95%, preferably ≥99%.

In another preferred embodiment, in the compound, $^{16}O$ isotope content at the oxygen atom position is ≥95%, preferably ≥99%.

Active Ingredients

As used herein, the term "the compound of the present invention" refers to the compound of formula (I). The term also comprises crystal forms, pharmaceutically acceptable salts, hydrates or solvates of the compound of formula (I).

Among which, the term "pharmaceutically acceptable salt" refers to a salt formed by the compound of the present invention and an acid or alkali which is suitable for a medicine. The pharmaceutically acceptable salts include inorganic and organic salts. A preferred type of salts are salts formed by the compounds of the present invention and an acid. Suitable salt-forming acids include, but are not limited to: inorganic acids such as hydrochloric acid, hydrobromic acid, hydrofluoric acid, sulfuric acid, nitric acid, phosphoric acid, and the like; organic acids such as formic acid, acetic acid, trifluoroacetic acid, propionic acid, oxalic acid, malonic acid, succinic acid, fumaric acid, maleic acid, lactic acid, malic acid, tartaric acid, citric acid, picric acid, benzoic acid, methanesulfonic acid, ethanesulfonic acid, p-toluene-sulfonic acid, benzenesulfonic acid, naphthalenesulfonic acid and the like; and amino acids such as proline, phenyl-alanine, aspartic acid, glutamic acid, and the like. Another preferred type of salts are salts formed by the compounds of the present invention and bases, e.g., alkali metal salts (e.g. sodium or potassium salts), alkaline earth metal salts (e.g. calcium or magnesium salts), ammonium salts (e.g., lower alkanol ammonium salts or other pharmaceutically acceptable amine salts), for example, methylamine salt, ethylamine salt, propylamine salt, dimethylamine salt, trimethylamine salts, diethylamine salts, triethylamine salts, tert-butyl amine salts, ethylenediamine salts, hydroxyethylamine salts, bi-hydroxyethylamine salts, tri-hydroxyethylamine salts, and amine salts formed by morpholine, piperazine, and lysine.

The term "solvate" refers to a complex of specific ratio formed by coordinating the compound of the present invention with solvent molecules. "Hydrate" refers to a complex formed by coordinating the compound of the present invention with water.

Moreover, the compounds of the present invention further comprise prodrugs of diaminopyrimidine compounds of formula (I). The term "prodrug" includes a type of compounds which have biological activity or non-activity, and would convert to the compound of formula (I) though metabolism or chemical reactions in the human body when administered by appropriate method, or the salt or solvate formed by a compound of formula (I). The prodrugs include (but are not limited to) the carboxylic acid ester, carbonic ester, phosphate, nitrate, sulfate, sulfone ester, sulfoxide esters, amino compounds, carbamates, azo compounds, phosphoramides, glucoside, ether, acetal of the compound, etc.

Preparation Method

Hereinafter the preparation of compounds of formula (I) will be described in detail, but such specific methods do not constitute any limitation to the present invention. The compounds of the invention may also be readily prepared by optionally combining various synthetic methods described in this specification or known in the art, such a combination can be readily performed by one of ordinary skill in the art to which the present invention belongs.

The methods used in the present invention for preparing the undeuterated diaminopyrimidine compounds and physiologically compatible salts thereof are known. Preparation of corresponding deuterated diaminopyrimidine compounds can be conducted by using the corresponding deuterated starting compound through the same synthesizing route. For example, a compound of formula (I) of the present invention can be prepared according to the method described in WO2008073687, except that deuterated materials are used instead of non-deuterated materials.

Generally, in the preparation process, each reaction is generally conducted in an inert solvent, under room temperature to reflux temperature (such as 0° C.~80° C., preferably from 0° C.~50° C.). The reaction time is usually 0.1 hours-60 hours, preferably 0.5 to 48 hours.

The following general preparative route may be used in the synthesis of compounds of formula (I) of the present invention.

Synthetic route I

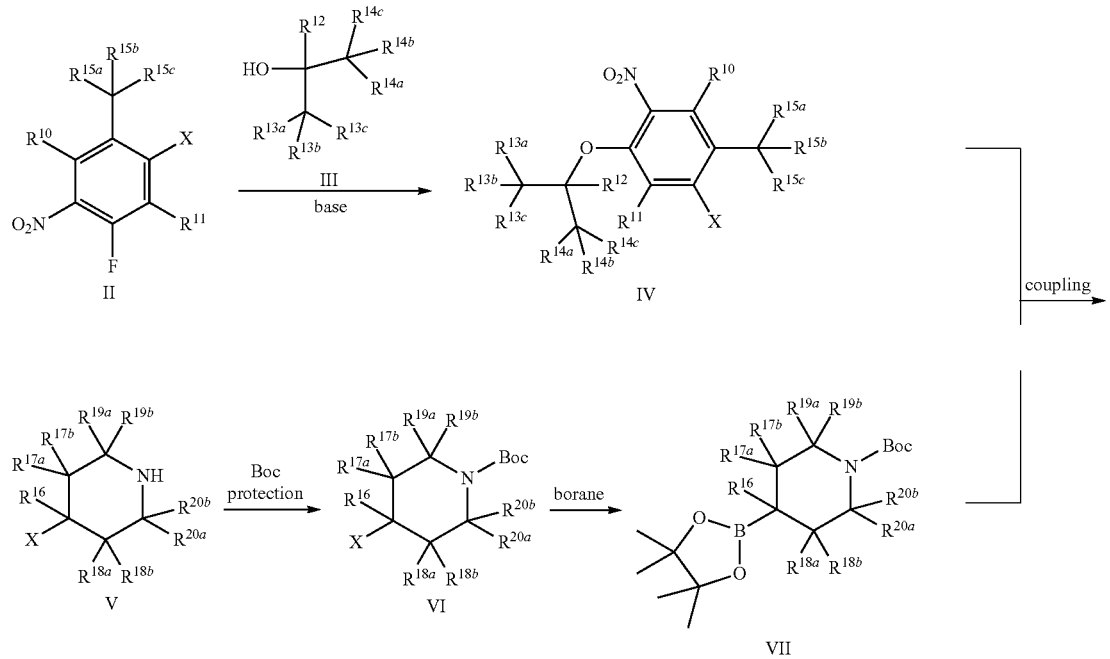

-continued
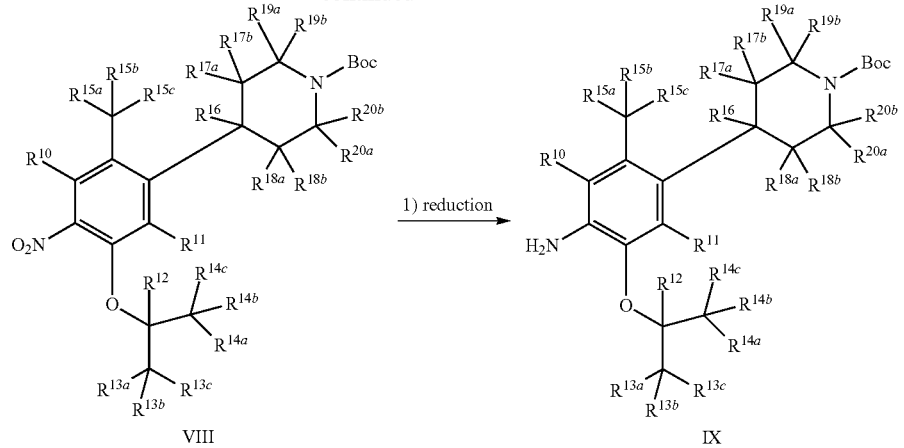
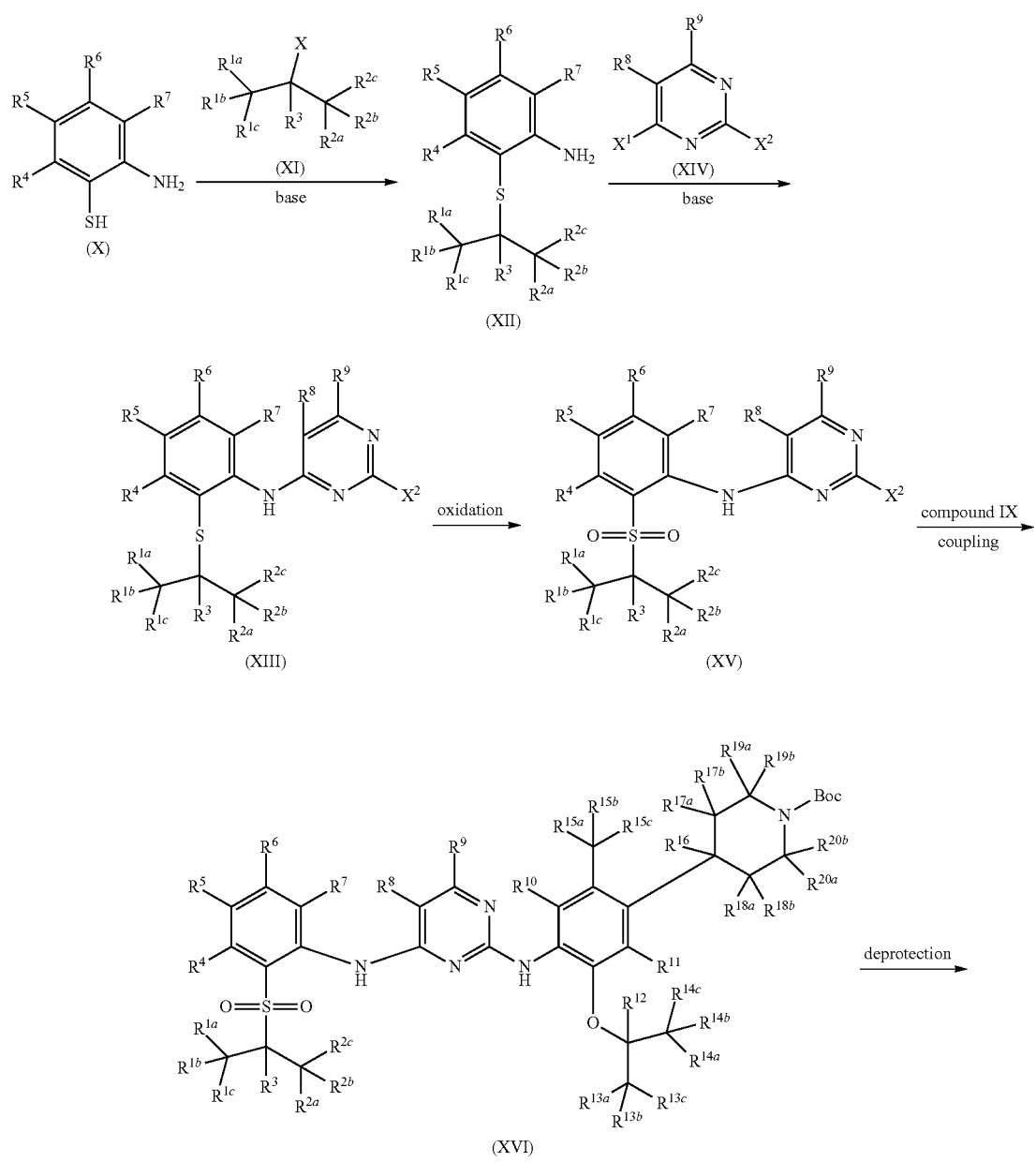

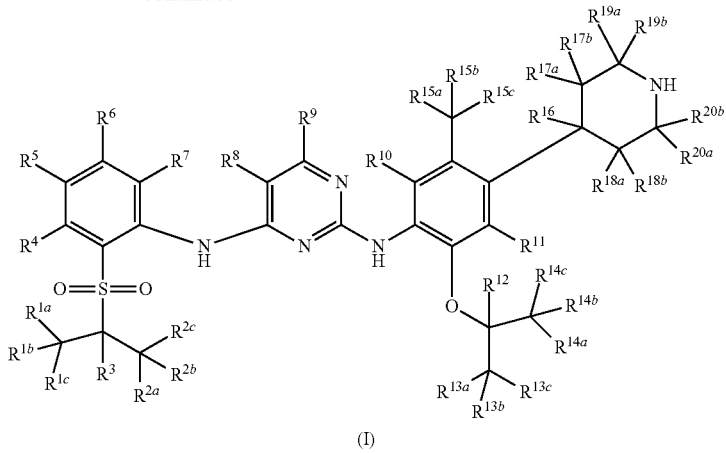

(I)

Wherein: X, $X^1$, $X^2$ are selected from F, Cl, Br, I, OTs, OMs, OTf; and $R^{1a}$, $R^{1b}$, $R^{1c}$, $R^{2a}$, $R^{2b}$, $R^{2c}$, $R^3$, $R^4$, $R^5$, $R^6$, $R^7$, $R^9$, $R^{10}$, $R^{11}$, $R^{12}$, $R^{13a}$, $R^{13b}$, $R^{13c}$, $R^{14a}$, $R^{14b}$, $R^{14c}$, $R^{15a}$, $R^{15b}$, $R^{15c}$, $R^{16}$, $R^{17a}$, $R^{17b}$, $R^{18a}$, $R^{18b}$, $R^{19a}$, $R^{19b}$, $R^{20a}$ or $R^{20b}$ are defined as above.

As shown in Synthetic route I, nitrobenzene compound II reacts with alkanol compound III under alkaline condition to provide compound IV. 4-chloro-piperidine compound V is Boc-protected to give compound VI, and boron compound VII is obtained by borane reaction. Compound IV and boron compound VII are coupled to obtain compound VIII by Suzuki coupling, and then aniline compound IX is obtained by reduction. Under basic condition, benzene sulfide compound XII is obtained from thiophenol compound X and alkyl halide compound XI through substitution reaction, then compound XII and 2,4-dihalogenated pyrimidine compound XIV are subjected to substitution reaction under basic condition to obtain 2-halosubstituted pyrimidine compound XIII, and then compound XV is obtained through an oxidation reaction. Compound XV and aniline compound IX are used to obtain compound XVI by coupling; and the compound I of the present invention is obtained from compound XVI through deprotection reaction of Boc. The above reactions are conducted in an inert solvent, such as dichloromethane, dichloroethane, acetonitrile, n-hexane, toluene, tetrahydrofuran, N,N-dimethylformamide, N,N-dimethylacetamide, dimethylsulfoxide, isopropanol, n-butanol, t-butanol, dioxane, etc., under a temperature of 0-200° C. The base is selected from potassium carbonate, cesium carbonate, sodium hydroxide, potassium hydroxide, n-butyllithium, t-butyllithium, iso-butyllithium, diisopropyl amino lithium, potassium phosphate, bis (trimethylsilyl) amino lithium, bis (trimethylsilyl) amino potassium, potassium tert-butoxide, sodium tert-butoxide, sodium ethoxide, 4-dimethylaminopyridine, pyridine, triethylamine, diisopropyl ethyl amine, and the like.

Synthetic route II

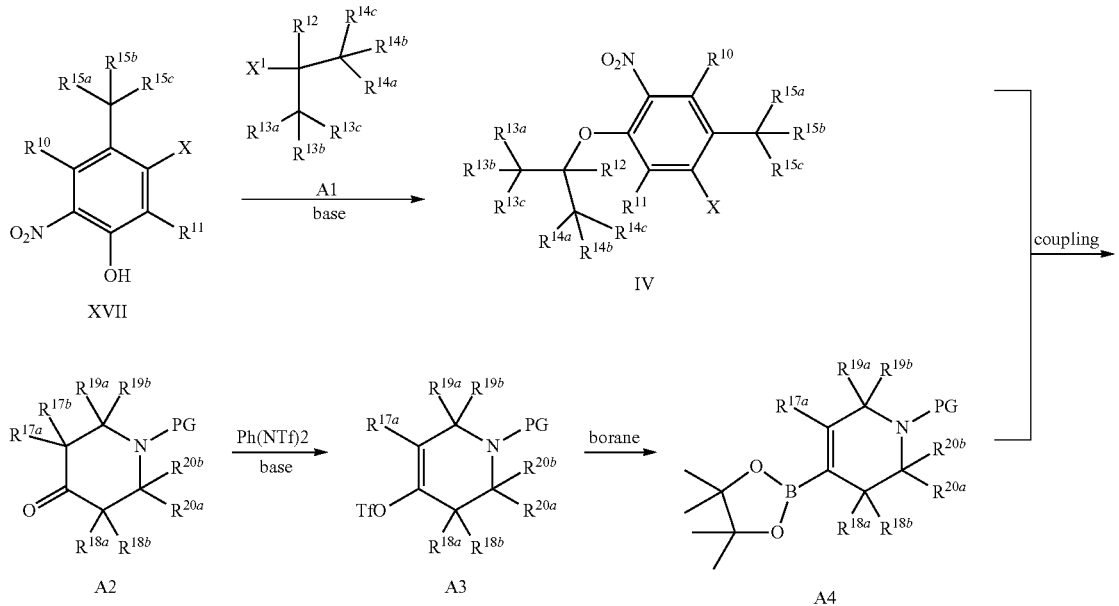

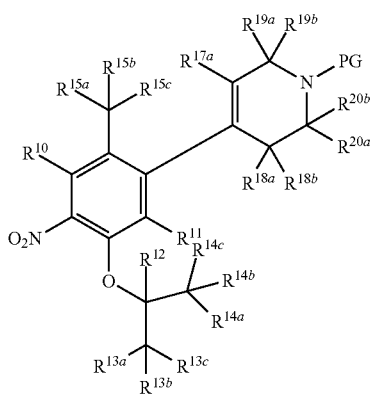

A5

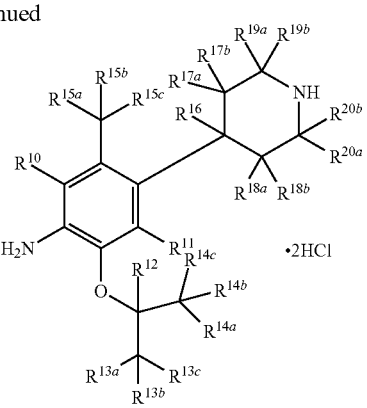

A6

1) reduction
2) deprotection
3) HCl

•2HCl compound XV

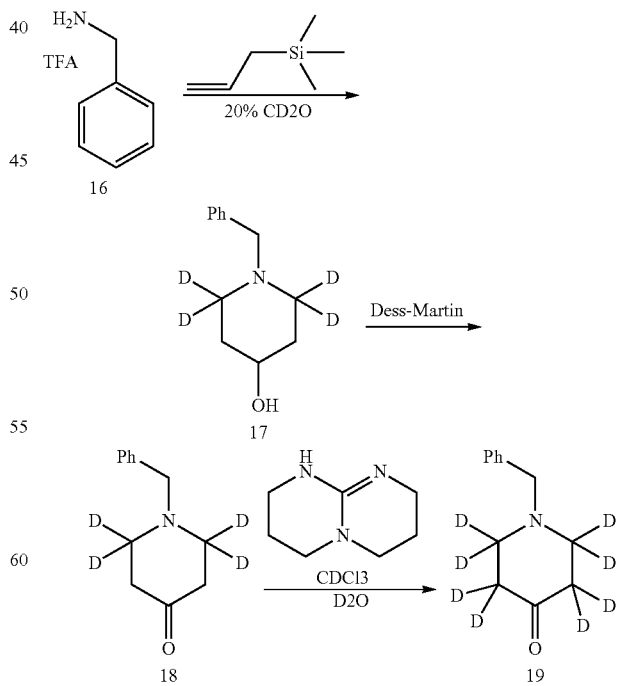

(I)

Wherein: X, $X^1$, $X^2$ are selected from F, Cl, Br, I, OTs, OMs, OTf; and $R^{1a}$, $R^{1b}$, $R^{1c}$, $R^{2a}$, $R^{2b}$, $R^{2c}$, $R^3$, $R^4$, $R^5$, $R^6$, $R^7$, $R^9$, $R^{10}$, $R^{11}$, $R^{12}$, $R^{13a}$, $R^{13b}$, $R^{13c}$, $R^{14a}$, $R^{14b}$, $R^{14c}$, $R^{15a}$, $R^{15b}$, $R^{15c}$, $R^{16}$, $R^{17a}$, $R^{17b}$, $R^{18a}$, $R^{18b}$, $R^{19a}$, $R^{19b}$, $R^{20a}$ or $R^{20b}$ are defined as above. PG is an amino protection group, such as tert-butoxycarbonyl group, a benzyl group, benzyloxycarbonyl group, p-methoxybenzyl group, and the like.

As shown in Synthetic route II, o-nitrophenol compound XVII reacts with compound A1 under a basic condition to provide compound IV. Under alkaline conditions, 4-piperidone compound A2 reacts with N-phenyl bi(trifluoromethylsulfonyl) imide to obtain compound A3, then it reacts with bispinacolatodiboronmin to obtain compound A4. Compound A5 is obtained from compound IV and compound A4 through SUZUKI coupling reaction; compound aniline hydrochloride A6 is obtained from compound A5 through reduction with hydrogen or deuterium gas, deprotection, and salification with hydrochloride; and compound A6 and compound XV are condensated to obtain compound I of the present invention. The above reactions are conducted in an inert solvent, such as dichloromethane, dichloroethane, acetonitrile, n-hexane, toluene, tetrahydrofuran, N,N-dimethylformamide, N,N-dimethylacetamide, dimethylsulfoxide, isopropanol, n-butanol, t-butanol, dioxane, etc., under a temperature of 0-200° C. The base is selected from potassium carbonate, cesium carbonate, sodium hydroxide, potassium hydroxide, n-butyllithium, t-butyllithium, iso-butyllithium, diisopropyl amino lithium, potassium phosphate, bis (trimethylsilyl) amino lithium, bis (trimethylsilyl) amino potassium, potassium tert-butoxide, sodium tert-butoxide, sodium ethoxide, 4-dimethylaminopyridine, pyridine, triethylamine, diisopropyl ethyl amine, and the like.

Deuterated compound A2 can be prepared by the following routes:

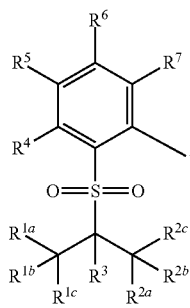

16

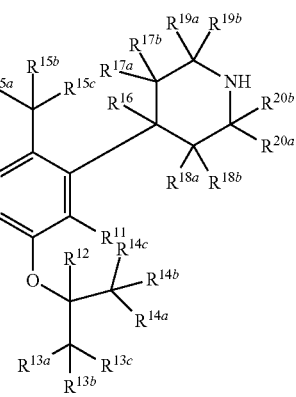

17

18 → 19

Referring to Journal of Labelled Compounds and Radiopharmaceuticals 2007, 50, 131-137, benzylamine trifluoroacetate 16 reacts with allyl trimethylsilyl ether and deuterated formaldehyde to obtain compound 17, and then compound 18 is obtained through Dess-Martin oxidation. Compound 18 is subjected to deuterium-hydrogen exchange with deuterated chloroform/heavy water under 1, 5, 7-trinitrine diazabicyclo (4.4.0) dec-5-ene to obtain compound 19.

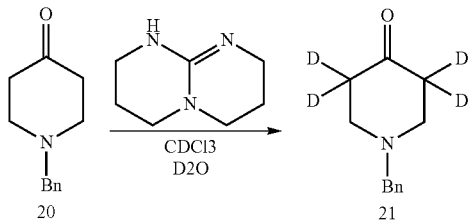

Compound 20 is subjected to deuterium-hydrogen exchange with deuterated chloroform/heavy water under 1,5,7-trinitrine diazabicyclo (4.4.0)dec-5-ene to obtain compound 21.

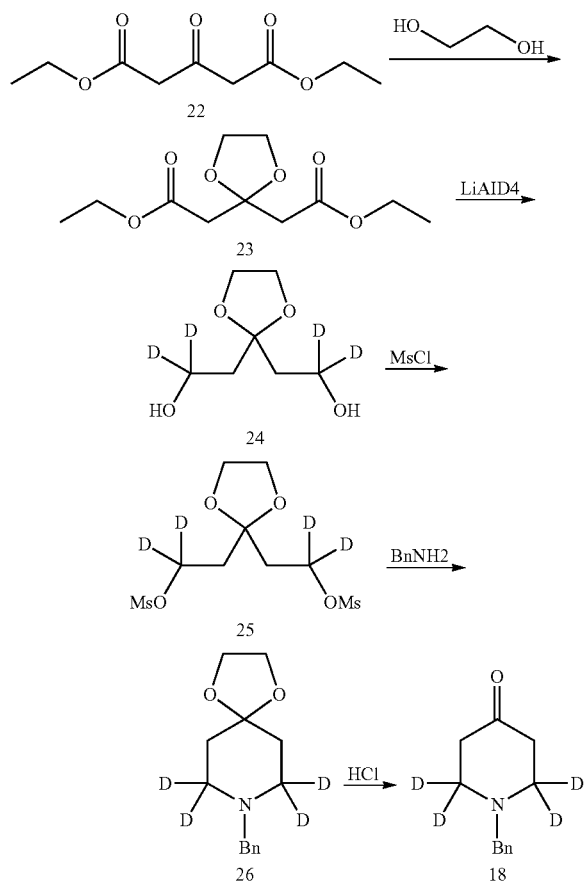

Compound 22 is protected by ethylene glycol to give ketal compound 23, which is then reduced by LiAlD$_4$ to give compound 24; compound 24 is protected by mesyl to give compound 25, and compound 25 reacts with benzylamine to give compound 26, which is deprotected by hydrochloric acid to give compound 18.

Deuterated compound A8 and A10 can be prepared by the following routes:

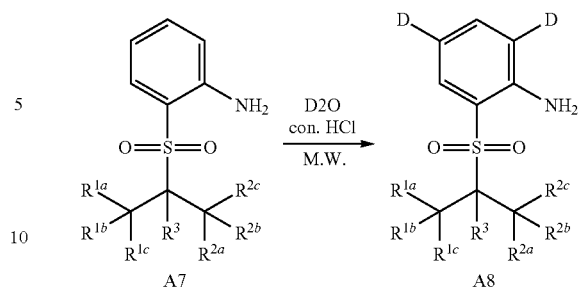

Wherein $R^{1a}$, $R^{1b}$, $R^{1c}$, $R^{2a}$, $R^{2b}$, $R^{2c}$, $R^3$ are defined as above.

Referring to Organic Letters, 2008, pp 4351-4353, compound A7 is microwave-heated in concentrated hydrochloric acid and heavy water to obtain compound A8.

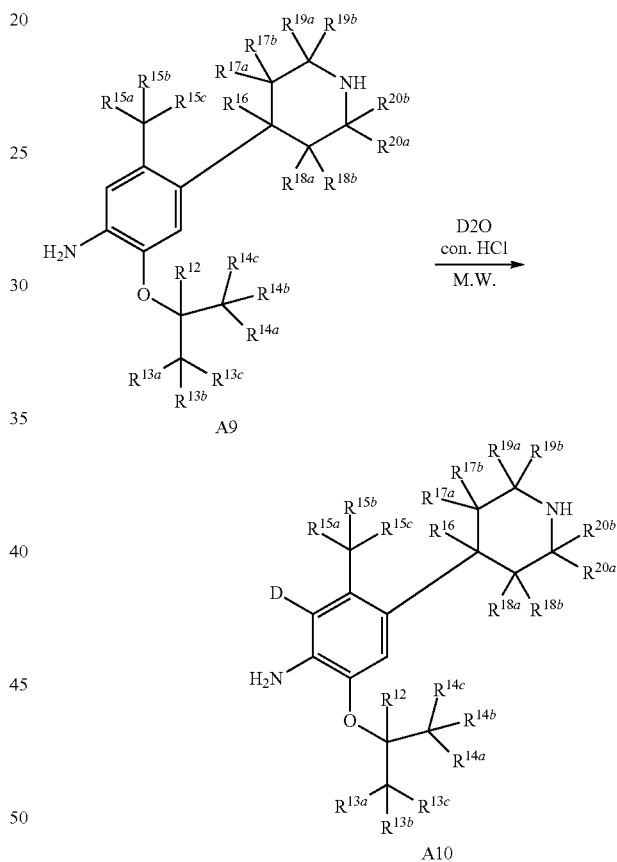

Wherein $R^{12}$, $R^{13a}$, $R^{13b}$, $R^{13c}$, $R^{14a}$, $R^{14b}$, $R^{14c}$, $R^{15a}$, $R^{15b}$, $R^{15c}$, $R^{16}$, $R^{17a}$, $R^{17b}$, $R^{18a}$, $R^{18b}$, $R^{19a}$, $R^{19b}$, $R^{20a}$ or $R^{20b}$ are defined as above.

Referring to Organic Letters, 2008, pp 4351-4353, compound A9 is microwave-heated in concentrated hydrochloric acid and heavy water to obtain compound A10.

Pharmaceutical Composition and Administration Thereof

The compounds of the present invention possess outstanding activity of inhibiting protein kinase, such as ALK kinases. Therefore, the compound of the present invention, and crystal forms, pharmaceutically acceptable inorganic or organic salts, hydrates or solvates thereof, and the pharmaceutical composition comprising the compound of the present invention as a main active ingredient can be used for treating, preventing and alleviating diseases mediated by protein kinase, (e.g. ALK kinases). Based on the prior art, the compounds of the invention can be used to treat the following diseases: cancers, cell proliferative disorders, cardiovascular diseases, inflammations, infections, autoimmune diseases, organ transplantations, viral diseases, cardiovascular diseases or metabolic diseases.

The pharmaceutical composition of the invention comprises the compound of the present invention or pharmaceutically acceptable salts thereof in a safe and effective dosage range and pharmaceutically acceptable excipients or carriers. Wherein, the term "safe and effective dosage" refers to the amount of the compound which is enough to improve the patient's condition without any serious side effect. Generally, the pharmaceutical composition contains 1-2000 mg of the compounds of the invention per dose, preferably, 10-1000 mg of the compounds of the invention per dose. Preferably, "per dose" means one capsule or tablet.

"Pharmaceutically acceptable carrier" means one or more compatible solid or liquid fillers or gel materials, which are suitable for human, and must have sufficient purity and sufficiently low toxicity. "Compatibility" herein means that components of the composition can be blended with the compounds of the invention or with each other, and would not significantly reduce the efficacy of the compounds. Some examples of pharmaceutically acceptable carriers include cellulose and the derivatives thereof (such as sodium carboxymethyl cellulose, sodium ethyl cellulose, cellulose acetate, etc.), gelatin, talc, solid lubricants (such as stearic acid, magnesium stearate), calcium sulfate, vegetable oils (such as soybean oil, sesame oil, peanut oil, olive oil, etc.), polyols (such as propylene glycol, glycerol, mannitol, sorbitol, etc.), emulsifiers (such as Tween®), wetting agent (such as sodium dodecyl sulfate), coloring agents, flavoring agents, stabilizers, antioxidants, preservatives, pyrogen-free water, etc.

There is no special limitation on administration mode for the compound or pharmaceutical compositions of the present invention, and the representative administration mode includes (but is not limited to): oral, intratumoral, rectal, parenteral (intravenous, intramuscular or subcutaneous), and topical administration.

Solid dosage forms for oral administration include capsules, tablets, pills, powders and granules. In these solid dosage forms, active compounds are mixed with at least one conventional inert excipient (or carrier), such as sodium citrate or $CaHPO_4$, or mixed with any of the following components: (a) fillers or compatibilizer, for example, starch, lactose, sucrose, glucose, mannitol and silicic acid; (b) binders, for example, hydroxymethyl cellulose, alginates, gelatin, polyvinylpyrrolidone, sucrose and arabic gum; (c) humectant, such as, glycerol; (d) disintegrating agents such as agar, calcium carbonate, potato starch or tapioca starch, alginic acid, certain composite silicates, and sodium carbonate; (e) dissolution-retarding agents, such as paraffin; (f) absorption accelerators, for example, quaternary ammonium compounds; (g) wetting agents, such as cetyl alcohol and glyceryl monostearate; (h) adsorbents, for example, kaolin; and (i) lubricants such as talc, stearin calcium, magnesium stearate, solid polyethylene glycol, sodium lauryl sulfate, or mixtures thereof. In capsules, tablets and pills, the dosage forms may also contain buffering agents.

The solid dosage forms such as tablets, sugar pills, capsules, pills and granules can be prepared by using coating and shell materials, such as enteric coatings and any other materials known in the art. They can contain an opaque agent. The release of the active compounds or compounds in the compositions can be released in a delayed mode in certain part of the digestive tract. Examples of the embedding components include polymers and waxes. If necessary, the active compounds and one or more above excipients can form microcapsules.

Liquid dosage forms for oral administration include pharmaceutically acceptable emulsions, solutions, suspensions, syrups or tinctures. In addition to the active compounds, the liquid dosage forms may contain any conventional inert diluents known in the art such as water or other solvents, solubilizers and emulsifiers, for example, ethanol, isopropanol, ethyl carbonate, ethyl acetate, propylene glycol, 1,3-butanediol, dimethyl formamide, as well as oil, in particular, cottonseed oil, peanut oil, corn germ oil, olive oil, castor oil and sesame oil, or the combination thereof.

Besides these inert diluents, the composition may also contain additives such as wetting agents, emulsifiers, and suspending agents, sweeteners, flavoring agents and perfume.

In addition to the active compounds, the suspension may contain suspending agent, for example, ethoxylated isooctadecanol, polyoxyethylene sorbitol and sorbitan esters, microcrystalline cellulose, methanol aluminum and agar, or the combination thereof.

The compositions for parenteral injection may comprise physiologically acceptable sterile aqueous or anhydrous solutions, dispersions, suspensions or emulsions, and sterile powders which can be re-dissolved into sterile injectable solutions or dispersions. Suitable aqueous and non-aqueous carriers, diluents, solvents or excipients include water, ethanol, polyols and any suitable mixtures thereof.

The dosage forms for topical administration of compounds of the invention include ointments, powders, patches, aerosol, and inhalants. The active ingredients are mixed with physiologically acceptable carriers and any preservatives, buffers, or propellant if necessary, under sterile conditions.

Compounds of the present invention can be administrated alone, or in combination with any other pharmaceutically acceptable compounds.

When the pharmaceutical compositions are used, a safe and effective amount of compound of the present invention is applied to a mammal (such as human) in need thereof, wherein the dose of administration is a pharmaceutically effective dose. For a person weighed 60 kg, the daily dose is usually 1-2000 mg, preferably 50-1000 mg. Of course, the particular dose should also depend on various factors, such as the route of administration, patient healthy status, which are well within the skills of an experienced physician.

Compared to non-deuterated compounds known in the prior art, the compounds of the present invention possess a number of advantages. The main advantages of the present invention are:

(1) The compounds of the present invention have a good inhibitory activity to protein kinase (such as ALK kinase).

(2) The metabolism of the deuterated compounds in the organism is changed by deuterate technology, thus rendering the compound better pharmacokinetic parameters characteristic. In this case, the dose may be varied and a long-acting preparation can be formed to improve the applicability.

(3) The drug concentration of the compound in animals can be enhanced through substitution of deuterium for hydrogen in the compound due to the deuterium isotope effect, thus improving drug efficacy.

(4) The security compound may be improved through substitution of deuterium for hydrogen in the compound, since some metabolites is suppressed.

The present invention will be further illustrated below with reference to the specific examples. It should be understood that these examples are only to illustrate the invention but not to limit the scope of the invention. The experimental methods with no specific conditions described in the following examples are generally performed under the conventional conditions, or according to the manufacture's instructions. Unless indicated otherwise, parts and percentage are calculated by weight.

The deuterated starting material used in the following embodiments (e.g., 1-bromo-5-fluoro-2-($d_3$-methyl)-4-nitrobenzene), may be deuterated compounds obtained from non-deuterated compounds (such as 1-bromo-5-fluoro-2-methyl-4-nitrophenyl) through deuteration reaction by a conventional method.

Example 1

Preparation of 5-chloro-$N^2$-(2-isopropoxy-5-methyl-4-(2,2,6,6-$d_4$-piperidin-4-yl) phenyl)-$N^4$-(2-(isopropylsulfonyl) phenyl)pyrimidine-2,4-diamine (Compound 13)

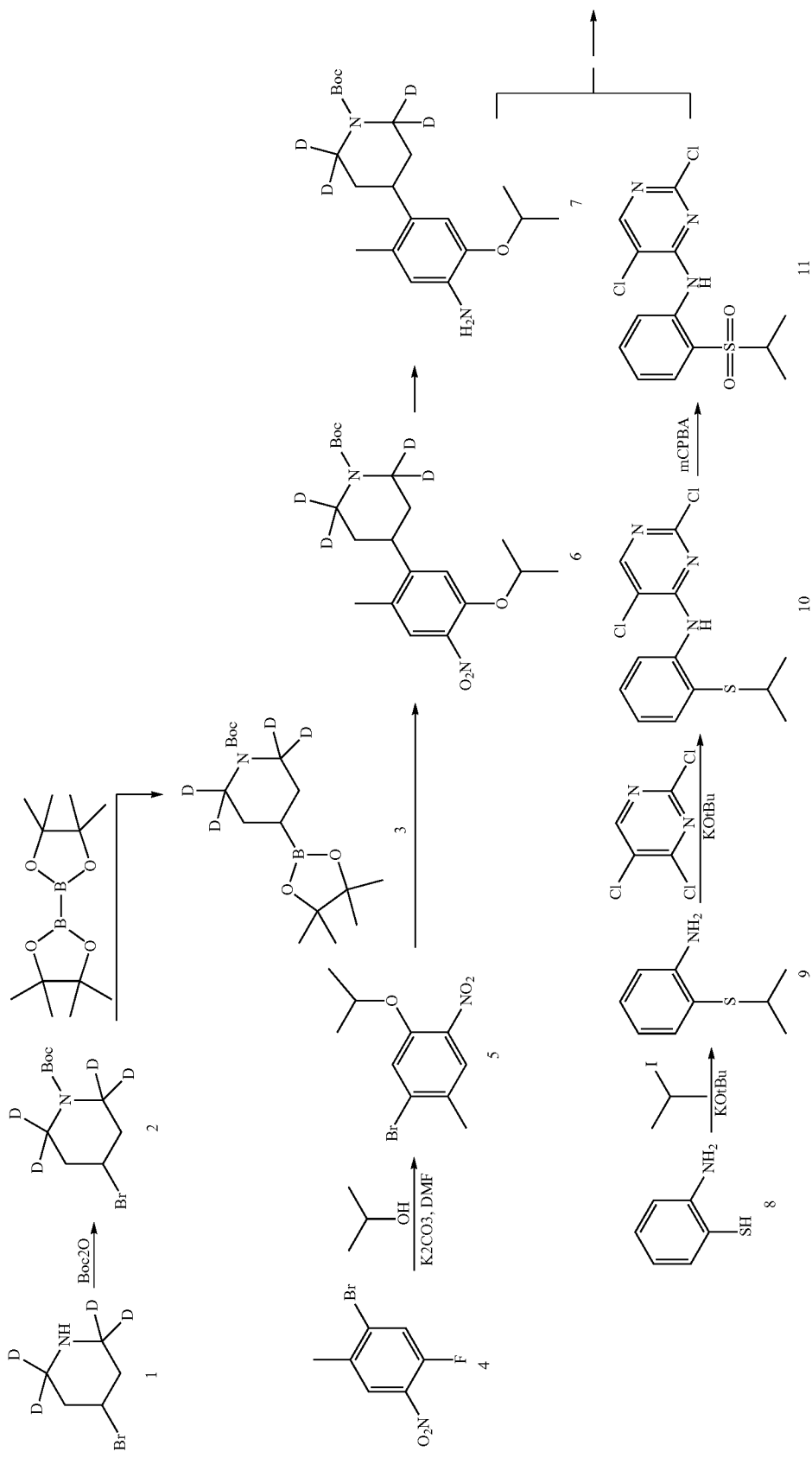

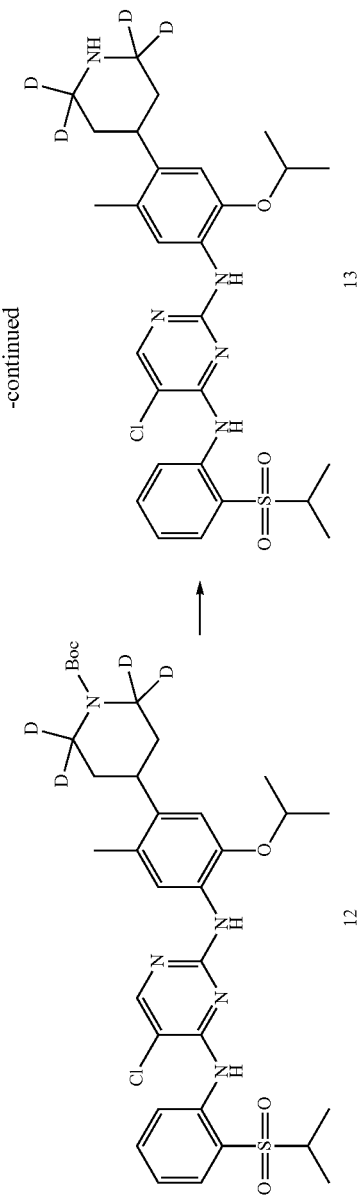

1. Preparation of 4-bromo-2,2,6,6-$d_4$-piperidine-1-carboxylic acid tert-butyl ester (Compound 2)

Compound 4-bromo-2,2,6,6-$d_4$-piperidine (0.84 g, 5 mmol) and dichloromethane (10 mL) were added into a flask successively. Under 0° C., N,N-diisopropylethylamine (0.65 g, 5 mmol) was added dropwise. After stirring for 0.5 hours, ditert-butyl dicarbonate (1.64 g, 7.5 mmol) in dichloromethane (10 mL) was added dropwise. Upon addition, the reaction solution was stirred at room temperature overnight. The reaction solution was respectively washed with hydrochloric aqueous solution (1 N, 2×10 mL) and saturated brine (10 mL). The organic layer was dried over anhydrous sodium sulfate, filtered and concentrated by a rotary evaporator under vacuo to give a crude product. The crude product was purified by silica gel column chromatography (eluent: n-hexane/ethyl acetate=5/1, v/v) to give the desired product as a colorless oil (1.23 g, yield 92%). $^1$H NMR (400 MHz, CDCl3) δ 4.34 (tt, J=7.69, 3.8 Hz, 1H), 2.16-2.05 (m, 2H), 1.95-1.82 (m, 2H), 1.48 (s, 9H).

2. Preparation of 4-(4,4,5,5-tetrabutyl-1,3,2-dioxaborolan-2-yl)-2,2,6,6-$d_4$-piperidine-1-carboxylic acid tert-butyl ester (Compound 3)

Cuprous iodide (48 mg, 0.25 mmol), triphenylphosphine (86 mg, 0.33 mmol), lithium methoxide (0.2 g, 5 mmol) and bis (pinacolato) diboron (0.965 g, 3.8 mmol) were sequentially added to a Schlenk reaction tube. System was replaced with argon for 3 to 4 times. Under argon, 4-bromo-2,2,6,6-$d_4$-piperidine-1-carboxylic acid tert-butyl ester (0.67 g, 2.5 mmol) in N,N-dimethylformamide (5 mL) was added. At 40° C., the reaction was stirred for 24 hrs. The reaction liquid was cooled to room temperature; ethyl acetate was added to dilute the reaction liquid, filtered through celite, and the filter cake was washed with ethyl acetate. The filterate was combined, and concentrated by a rotary evaporator under vacuo to give a crude product. Purificate by silica gel column chromatography to give the desired product as a earthy yellow oil (0.47 g, yield 60%). GC-MS Calcd.: 315; GC-MS Found: 315; $^1$HNMR (CDCl3, 400 MHz) δ 1.50-1.58 (m, 2H), 1.40-1.46 (m, 2H), 1.38 (s, 9H), 1.16 (s, 12H), 1.00-1.08 (m, 1H).

3. Preparation of 1-bromo-5-isopropoxy-2-methyl-4-nitrobenzene (Compound 5)

Compound 1-bromo-5-fluoro-2-methyl-4-nitrobenzene (4.68 g, 20 mmol) and anhydrous N,N-dimethylformamide (15 mL) were added into the flask successively. Under the protection of nitrogen, Potassium carbonate (8.29 g, 60 mmol) and isopropanol (2.40 g, 40 mmol) were added successively. The temperature was raised to 50° C., and the reaction mixture was stirred overnight. After cooled to room temperature, water (20 mL) and ethyl acetate (30 mL) were added to dilute the reaction liquid; the reaction liquid was stirred for 15 mins, and was layered. Then the aqueous layer was extracted with ethyl acetate (30 mL) for twice. The organic layers were combined, and washed with water and brine successively, dried over anhydrous sodium sulfate, filtered and concentrated by a rotary evaporator under vacuo to give a crude product. The crude product was purified by silica gel column chromatography (eluent: petroleum ether/ethyl acetate=10/1, v/v) to give the desired product as a yellow solid (4.44 g, yield 81%).

4. Preparation of 4-(5-isopropoxy-2-methyl-4-nitrophenyl)-2,2,6,6-$d_4$-piperidine-1-carboxylic acid tert-butyl ester (Compound 6)

Compound 1-bromo-5-isopropoxy-2-methyl-4-nitrobenzene (1.37 g, 5.0 mmol), aqueous sodium carbonate (2 M, 8.35 mL, 16.7 mmol) and 1,2-methoxyethane (50 mL) were added into a flask successively. Under stirring, 4-(4,4,5,5-tetrabutyl-1,3,2-dioxaborolan-2-yl)-2,2,6,6-$d_4$-piperidine-1-carboxylic acid tert-butyl ester (1.50 g, 4.76 mmol) was added. The above suspension was degassed under an argon atmosphere for 5 mins, to which was added triphenylphosphine (0.26 g, 1 mmol) and palladium acetate (0.11 g, 0.5 mmol), refluxed for 24 h under 85° C. It was cooled to room temperature, ethyl acetate (50 mL) and water (40 mL) were added, and layered. Then the aqueous layer was extracted with ethyl acetate for twice. The organic layers were combined, and washed with water and brine successively, dried over anhydrous sodium sulfate, filtered and concentrated by a rotary evaporator under vacuo to give a crude product. The crude product was purified by silica gel column chromatography to give the desired product as a white solid (1.37 g, yield 75%). MS Calcd.: 382; MS Found: 383 (M+H)$^+$, 405 (M+Na)$^+$.

5. Preparation of 4-(4-amino-5-isopropoxy-2-methylphenyl)-2,2,6,6-$d_4$-piperidine-1-carboxylic acid tert-butyl ester (Compound 7)

4-(5-isopropoxy-2-methyl-4-nitrophenyl)-2,2,6,6-$d_4$-piperidine-1-carboxylic acid tert-butyl ester (1.30 g, 3.40 mmol), ethanol (10 mL) and water (1 mL) were sequentially added to a hydrogenation reaction flask. 10% palladium carbon (0.13 g) was added under nitrogen. After the system was replaced with hydrogen for 3 to 4 times, it was stirred at 40° C. for 5 hours at a hydrogen pressure of 1 atm. The reaction was detected to have completed by HPLC. The reaction solution was cooled to room temperature, filtered through Celite, and the filter cake was washed with ethanol. The filterate was combined, and concentrated by a rotary evaporator under vacuo to give the desired product, off-white solid (1.16 g, yield: 97%). MS Calcd.: 352; MS Found: 353 (M+H)$^+$.

6. Preparation of 2-(isopropylthio) aniline (Compound 9)

Under the protection of nitrogen, compound 2-aminothiophenol (12.52 g, 0.1 mol), 2-iodopropane (18.71 g, 0.11 mol) and ethanol (130 mL) was successively added to a flask. Under stirring, potassium tert-butoxide (14.61 g, 0.13 mol) was slowly added under 0° C. The reaction was warmed to room temperature and conducted for 4 hours, and the reaction was monitored as being substantially completed by HPLC. The reaction mixture was filtered through Celite, the filter cake was washed with ethanol and the combined filtrate was concentrated in vacuo by rotary evaporator. The residue was dissolved in ethyl acetate (200 mL), washed with water and brine successively. It was dried over anhydrous sodium sulfate, filtered and concentrated by a rotary evaporator under vacuo to give a crude product. The crude product was purified by silica gel column chromatography to give the desired product as yellowish oil. MS Calcd.: 167; MS Found: 168 (M+H)$^+$.

7. Preparation of 2,5-dichloro-N-(2-(isopropylthio) phenyl) pyrimidin-4-amine (Compound 10)

Under the protection of nitrogen, 2-(isopropylthio) aniline (0.50 g, 3.0 mmol), 2,4,5-trichloropyrimidine (0.37 g, 2.0 mmol) and anhydrous N,N-dimethyl formamide (12 mL) were successively added to a flask. Under stirring, potassium tert-butoxide (0.67 g, 6.0 mol) was slowly added at 0° C. The reaction was warmed to room temperature for 2 hrs. The reaction mixture was added into pure water (100 mL) to quench the reaction. Then it was extracted with ethyl acetate for three times. The organic layers were combined, and washed with water and brine successively. It was dried over anhydrous sodium sulfate, filtered and concentrated by a rotary evaporator under vacuo to give a crude product. The crude product was purified by silica gel column chromatography to give the desired product as white soild. MS Calcd.: 314; MS Found: 315 (M+H)$^+$, 337 (M+Na)$^+$.

8. Preparation of 2,5-dichloro-N-(2-(isopropylsulfonyl) phenyl) pyrimidin-4-amine (Compound 11)

Under the protection of nitrogen, 2,5-dichloro-N-(2-(isopropylthio) phenyl) pyrimidin-4-amine (0.50 g, 1.59 mmol) and dichloromethane (50 mL) were successively added into a flask. 3-chloroperbenzoic acid (85%, 0.41 g, 2.0 mmol) was added under stirring. The reaction was kept at room temperature for 5 hrs. Dichloromethane (20 mL) was added, and it was washed with water, saturated sodium bicarbonate solution and brine successively. The organic layer was dried over anhydrous sodium sulfate, filtered and concentrated by a rotary evaporator under vacuo to give a crude product. The crude product was purified by silica gel column chromatography to give the desired product (0.33 g, yield: 60%). MS Calcd.: 345; MS Found: 346 (M+H)$^+$, 368 (M+Na)$^+$.
$^1$HNMR (CDCl$_3$, 400 MHz) δ 10.10 (s, 1H), 8.65 (d, 1H), 8.32 (s, 1H), 7.92 (m, 1H), 7.71-7.76 (m, 1H), 7.29-7.32 (m, 1H), 3.18-3.25 (m, 1H), 1.36 (s, 6H).

9. Preparation of 4-(4-(5-chloro-4-(2-(isopropylsulfonyl) phenyl)amino) pyrimidin-2-yl-amino)-5-isopropoxy-2-methylphenyl)-2,2,6,6-d$_4$-piperidine-1-carboxylic acid tert-butyl ester (Compound 12)

Under the protection of nitrogen, 4-(4-amino-5-isopropoxy-2-methylphenyl)-2,2,6,6-d$_4$-piperidine-1-carboxylic acid tert-butyl ester (353 mg, 1 mmol), 2,5-dichloro-N-(2-(isopropylsulfonyl) phenyl) pyrimidin-4-amine (346 mg, 1 mmol), 4,5-bisdiphenyl phosphine-9,9-dimethyl-xanthene (xantphos, 58 mg, 0.1 mmol), palladium acetate (18 mg, 0.08 mmol), cesium carbonate (978 mg, 3 mmol) and tetrahydrofuran (10 mL) were successively added into a flask. Under stirring, the mixture was bubbled in nitrogen sufficiently for 10 min. The mixture was charged into a tube, the tube was sealed and the reaction was conducted by microwave at 150° C. for 30 mins. Then the mixture was cooled and diluted by tetrahydrofuran, filtered and concentrated by rotary evaporator under vacuo to give a crude product. The crude product was purified by column chromatography to give the desired product (0.20 g, yield: 30%). MS Calcd.: 661; MS Found: 662 (M+H)$^+$, 684 (M+Na)$^-$.

10. Preparation of 5-chloro-N$^2$-(2-isopropoxy-5-methyl-4-(2,2,6,6-d$_4$-piperidin-4-yl) phenyl)-N$^4$-(2-(isopropylsulfonyl)phenyl)pyrimidine-2,4-diamine (Compound 13)

Under the protection of nitrogen, 4-(4-(5-chloro-4-(2-(isopropylsulfonyl) phenylamino) pyrimidin-2-yl-amino)-5-isopropoxy-2-methylphenyl)-2,2,6,6-d$_4$-piperidine-1-carboxylic acid tert-butyl ester (0.18 g, 0.27 mmol) and dichloromethane (5 mL) were successively added into a flask. Trifluoroacetic acid (3 ml) was added dropwise under stirring. The reaction was kept at room temperature for 1.5 hrs. Saturated aqueous sodium carbonate was added, the reaction solution was concentrated with rotary evaporator in vacuo, and extracted with ethyl acetate for three times. The organic layers were combined, and washed with water and brine successively, dried over anhydrous sodium sulfate, filtered and concentrated by a rotary evaporator under vacuo to give a crude product. The crude product was purified by preparative LC-MS to give the desired product as white solid (0.12 g, yield: 80%). MS Calcd.: 561; MS Found: 562 (M+H)$^+$, 584 (M+Na)$^+$.

Another method for preparing compound 13:

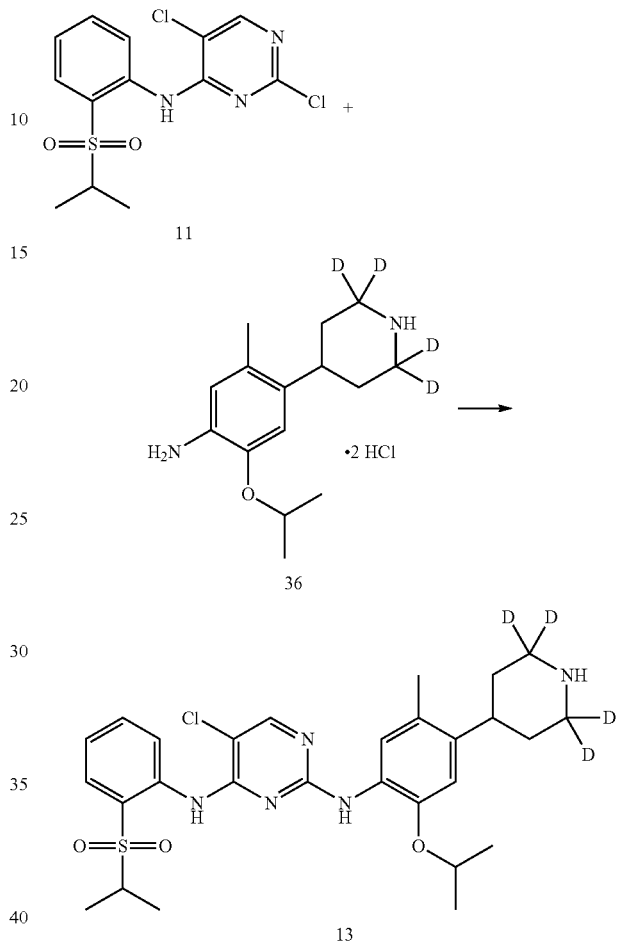

Under the protection of nitrogen, compound 2-isopropoxy-5-methyl-4-(2,2,6,6-d$_4$-piperidin-4-yl) aniline dihydrochloride (0.50 g, 1.54 mmol), 2,5-dichloro-N-(2-(isopropylsulfonyl) phenyl) pyrimidin-4-amine (0.58 g, 1.69 mmol) and isopropanol (6 ml) were added into a flask, the reaction was warmed to 85° C. and conducted overnight, and the reaction was monitored as being substantially completed by HPLC. The reaction mixture was cooled to room temperature, and stirred for 3 hours to precipitate the solid. The mixture was filtered, and the filter cake was beating washed with cold isopropanol to give the desired product hydrochloride. The hydrochloride was dissolved in pure water, an aqueous solution of sodium carbonate was added dropwise slowly to neutralize the pH to 8.5, and then extracted with ethyl acetate for three times. The combined organic phase was dried over anhydrous sodium sulfate, and concentrated to give the desired product as a white solid (0.68 g, yield: 78%). MS Calcd.: 561; MS Found: 562 (M+H)$^+$, 584 (M+Na)$^+$. $^1$HNMR (DMSO-d$_6$+D$_2$O, 400 MHz) δ 8.47 (d, J=7.6 Hz, 1H), 8.24 (s, 1H), 7.85-7.83 (dd, J=7.6, 2.0 Hz, 1H), 7.62 (t, J=7.6 Hz, 1H), 7.52 (s, 1H), 7.36 (t, J=7.6 Hz, 1H), 6.79 (s, 1H), 4.53-4.50 (m, 1H), 3.45-3.38 (m, 1H), 2.94-2.92 (m, 1H), 2.33 (s, 3H), 1.79-1.64 (m, 4H), 1.21 (d, 6H), 1.15 (d, 6H).

Example 2
Preparation of 5-chloro-$N^2$-(2-(2-d-prop-2-yloxy)-5-methyl-4-(2,2,6,6-$d_4$-piperidin-4-yl)phenyl)-$N^4$-(2-(isopropylsulfonyl)phenyl)pyrimidine-2,4-diamine
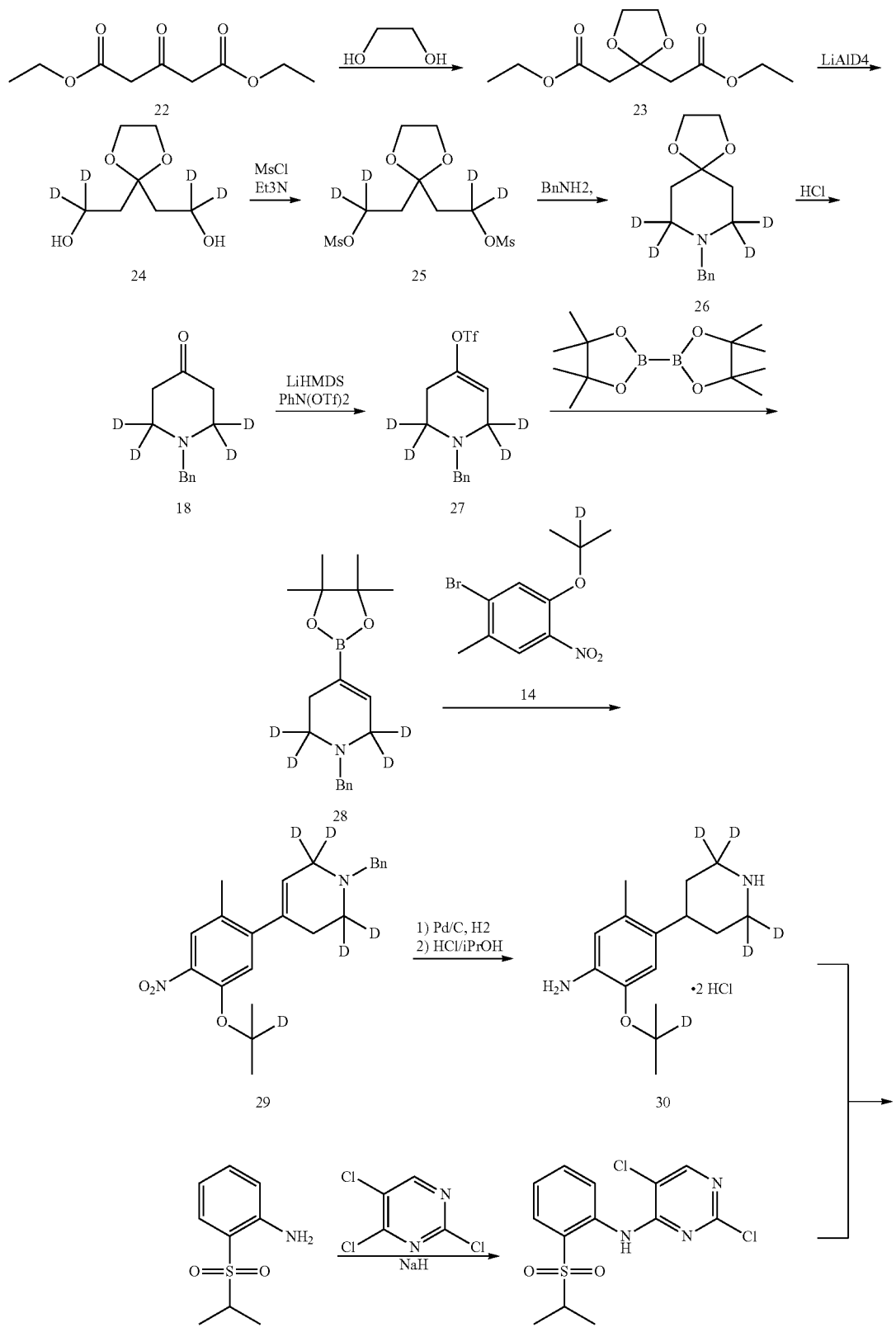

-continued

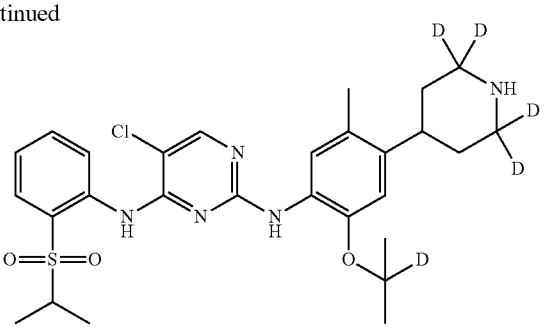

31

1. Preparation of 1-bromo-5-(2-d-prop-2-yloxyl)-2-methyl-4-nitrobenzene (Compound 14)

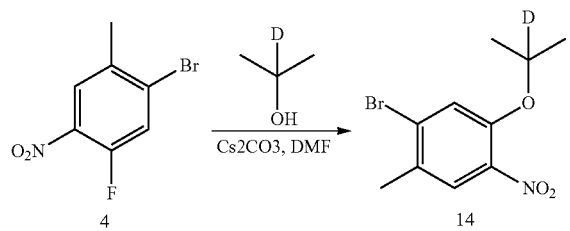

Compound 1-bromo-5-fluoro-2-methyl-4-nitrobenzene (468 mg, 2 mmol) and anhydrous N,N-dimethylformamide (5 mL) were added into a flask successively. Under the protection of nitrogen, cesium carbonate (1.95 g, 6 mmol) and 2-d-isopropanol (240 mg, 4 mmol) were added successively. The temperature was raised to 50° C., and the reaction mixture was stirred overnight. After cooled to room temperature, water and ethyl acetate were added to dilute the reaction liquid; it was stirred for 15 min, and layered. Then the aqueous layer was extracted with ethyl acetate for twice. The organic layers were combined, washed with water and brine successively, dried over anhydrous sodium sulfate, filtered and concentrated by a rotary evaporator under vacuo to give a crude product. The crude product was purified by TLC preparative plate chromatography (eluent: petroleum ether/ethyl acetate=10/1, v/v) to give the desired product as a yellow solid (468 mg, yield 85%).

Compound 14 can also be prepared by the following routes:

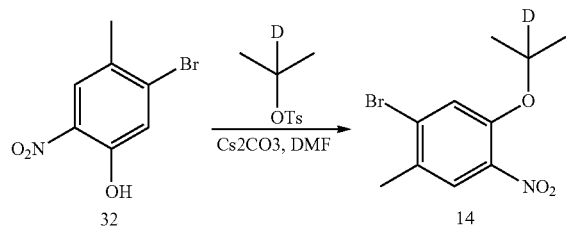

Under the protection of nitrogen, compound 5-bromo-4-methyl-2-nitrophenol (194 mg, 0.84 mmol), N,N-dimethylformamide (5 mL), 2-d-isopropyl p-toluenesulfonate (150 mg, 0.70 mmol), cesium carbonate (454 mg, 1.40 mmol) were added in a flask, warmed to 60° C. overnight. After cooled to room temperature, the reaction was quenched by adding water, and extracted by ethyl acetate, kept for separation, and the organic layer was washed successively with water and saturated brine, dried over anhydrous magnesium sulfate, and filtered, and the filtrate was concentrated in vacuo with rotary evaporator to give a crude product, and purified by TLC preparative plate chromatography (developing solvent: petroleum ether/ethyl acetate=10/1, v/v) to give the desired product as a yellow solid (140 mg, 73% yield). $^1$HNMR (DMSO-d6, 400 MHz) δ 8.08 (s, 1H), 7.46 (s, 1H), 2.41 (s, 3H), 1.28 (s, 6H).

2. Preparation of diethyl 2,2'-(1,3-dioxolane-2,2-diyl)diacetate

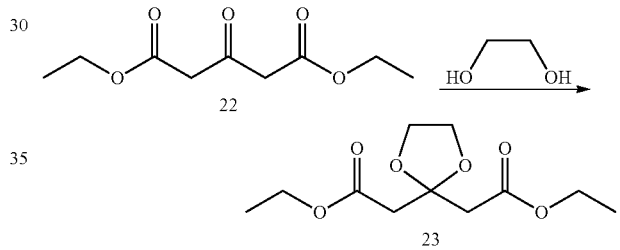

Under the protection of nitrogen, compound diethyl 1,3-acetone dicarboxylate (8 g, 40 mmol), dichloromethane (80 mL) and ethylene glycol (8.9 mL, 160 mmol) were added into a flask, cooled to 0° C., and boron trifluoride diethyl etherate (7.6 mL, 60 mmol) was added dropwise. Upon addition, the reaction mixture was stirred for 1 hr at 0° C., and then naturally warmed to room temperature and stirred overnight. After cooled to 0° C., water (40 mL) was added dropwise, and the aqueous phase was separated and extracted with dichloromethane. The combined organic phase was washed with saturated brine, dried over anhydrous magnesium sulfate, and filtered. The filtrate was concentrated with rotary evaporator in vacuo to give the desired product as a yellow liquid (9 g, yield 92%). $^1$HNMR (CDCl$_3$, 400 MHz) δ 4.20-4.15 (q, 4H), 4.03 (s, 4H), 2.96 (s, 4H), 1.30-1.27 (t, 6H).

3. Preparation of 2,2'-(1,3-dioxolane-2,2-diyl)-1,1,1',1'-d$_4$-diethanol

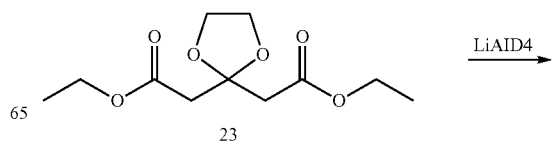

-continued

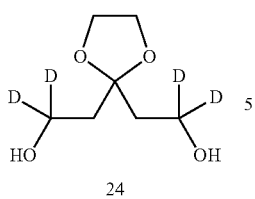

Under the protection of nitrogen, deuterated lithium aluminum hydride (510 mg, 12 mg) and tetrahydrofuran (40 mL) were added into a flask successively, and cooled to 0° C. Compound diethyl 2,2'-(1,3-dioxolane-2,2-diyl) diacetate (1.5 g, 6 mmol) was dissolved in tetrahydrofuran (10 mL), and the solution was added into the above reaction solution dropwise. Upon addition, the reaction mixture was stirred for 1 h at 0° C., and then naturally warmed to room temperature and stirred overnight. The reaction liquid was cooled to 0° C. in an ice bath, aqueous solution of 2 N NaOH was added dropwise, filtered, and the filter cake was drip-washed with ethyl acetate, and the filtrate was concentrated with rotary evaporator in vacuo to give the desired product as a colorless liquid (800 mg, yield 79%). $^1$HNMR (CDCl$_3$, 400 MHz) δ 4.08 (s, 4H), 3.75 (s, 2H), 1.99 (s, 4H).

4. Preparation of (1,3-dioxolane-2,2-diyl)bis(1,1-d$_2$-ethyl-2,1-diyl) dimethanesulfonate

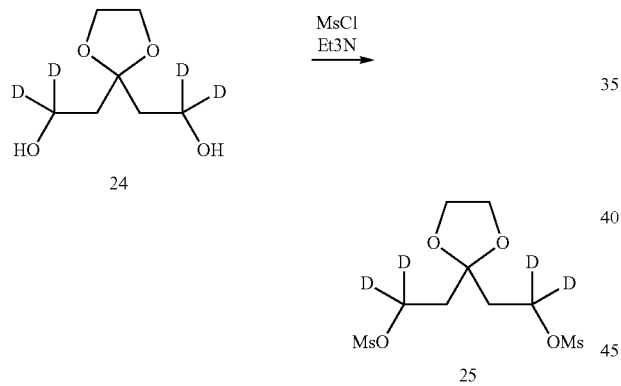

Under the protection of nitrogen, 2,2'-(1,3-dioxolane-2,2-diyl)-1,1,1',1'-d$_4$-diethanol (800 mg, 4.81 mmol), triethylamine (1.15 g, 11.38 mmol) and tetrahydrofuran (16 mL) were added into a flask successively, and cooled to −30° C. Methanesulfonyl chloride (1.38 g, 12.03 mmol) was dissolved in tetrahydrofuran (2 mL), and the solution was added into the above reaction solution dropwise. Upon addition, the dry ice bath was removed, the reaction liquid was warmed naturally to room temperature and stirred overnight. Into the reaction liquid was successively added methylene chloride and saturated ammonium chloride solution, and the organic layer was separated, washed with saturated brine, dried over anhydrous magnesium sulfate, and filtered, and the filtrate was concentrated in vacuo with rotary evaporator to give a crude product, and purified by TLC preparative plate chromatography (developing solvent: petroleum ether/ethyl acetate=1/50, v/v) to give the desired product as a white solid (900 mg, 58% yield). $^1$HNMR (CDCl$_3$, 400 MHz) δ 4.00 (s, 4H), 3.05 (s, 6H), 2.15 (s, 4H).

5. Preparation of 1-benzyl-4-(2,2,6,6-d$_4$-piperidine)-ethyleneketal

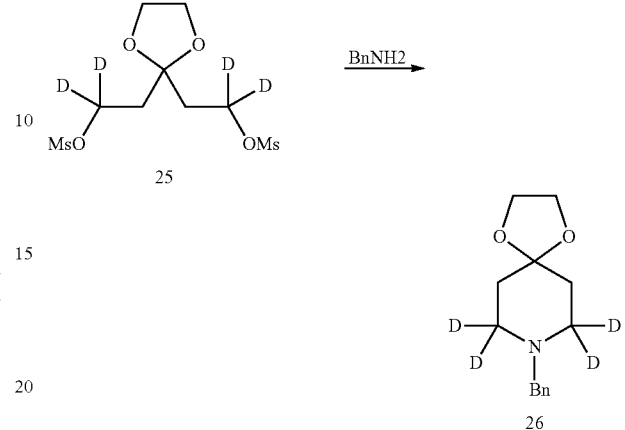

(1,3-dioxolane-2,2-diyl) bis (1,1-d$_2$-ethyl-2,1-diyl) dimethanesulfonate (300 mg, 0.89 mmol) and absolute ethanol (10 mL) was added into a flask, and benzylamine (973 mg, 8.90 mmol) was added by stirring. The reaction liquid was stirred and refluxed overnight. The reaction liquid was cooled to room temperature, and water was added to quench the reaction. Extracted with dichloromethane, the combined organic phase was successively washed with saturated ammonium chloride solution, water and brine, and dried over anhydrous sodium sulfate. The combined organic phase was concentrated in vacuo to give a crude product. The crude product was separated and purified by preparative TLC (developing solvent: methanol/dichloromethane=5/95, v/v) to give the desired product (145 mg, yield 66%). $^1$HNMR (CDCl$_3$, 400 MHz) δ 7.39-7.31 (m, 5H), 3.97 (s, 4H), 3.62 (s, 2H), 1.80 (s, 4H).

6. Preparation of 1-benzyl-2,2,6,6-d$_4$-piperidin-4-one

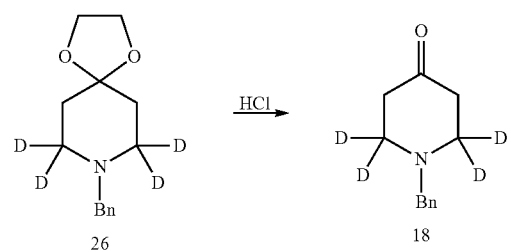 [SMILES: [2H]C1([2H])CC2(CC([2H])([2H])N1Cc1ccccc1)OCCO2 ; Cl ; [2H]C1([2H])CC(=O)CC([2H])([2H])N1Cc1ccccc1]

Compound 1-benzyl-4-(2,2,6,6-d$_4$-piperidine)-ethyleneketal (135 mg, 0.57 mmol) and absolute methanol (5 mL) were added into the flask successively. Under stirring, 2 M hydrochloric acid (3 ml, 5.7 mmol) was added, and refluxed for 6 h. The solvent was removed by concentration under reduced pressure, and saturated sodium bicarbonate solution was added for neutralization, and extracted with dichloromethane. The oil phase was dried over anhydrous sodium sulfate and concentrated, the crude product was purified by TLC preparative plate chromatography (developing solvent: methanol/methylene chloride=4/96, v/v) to give the desired product as a yellow oil (83 mg, 75% yield).

7. Preparation of 1-benzyl-1,2,3,6-(2,2,6,6-d₄-tetra-hydropyridin)-4-yl-trifluoromethanesulfonate

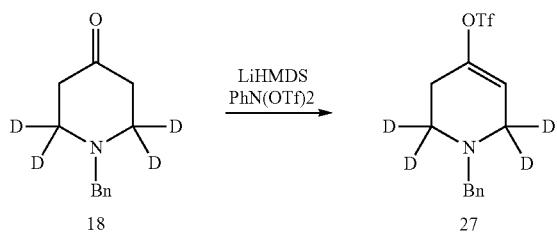 [SMILES: [2H]C1([2H])CC(=O)CC([2H])([2H])N1Cc1ccccc1 ; [2H]C1([2H])C=C(OS(=O)(=O)C(F)(F)F)CC([2H])([2H])N1Cc1ccccc1]

Compound 1-benzyl-2,2,6,6-d₄-piperidin-4-one (80 mg, 0.41 mmol) and anhydrous tetrahydrofuran (5 ml) were added into a flask successively, and was cooled to −78° C. Under nitrogen protection, LiHMDS in tetrahydrofuran (0.5 ml, 0.49 mmol, 1M) was added, and kept stirring for 30 min. After that, PhN(Tf)₂ (175 mg, 0.49 mmol) was added, stirred at room temperature for one hour, then stirred under reflux for 2 hours. Water was added to quench the reaction. The mixture was extracted with ethyl acetate, and the oil phases were washed with saturated sodium bicarbonate solution separately, dried over anhydrous sodium sulfate and concentrated, and the crude product was purified by TLC preparative plate chromatography (developing solvent: ethyl acetate/petroleum ether=15/85, v/v) to give the desired product as a yellow oil (85 mg, yield 63%). ¹HNMR (CDCl₃, 400 MHz) δ 7.37-7.30 (m, 5H), 5.75 (s, 1H), 3.65 (s, 2H), 2.46 (s, 2H).

8. Preparation of 1-benzyl-2,2,6,6-d₄-4-(4,4,5,5-tetramethyl-1,3,2-dioxaborolan-2-yl)-1,2,3,6-tetrahydropyridine

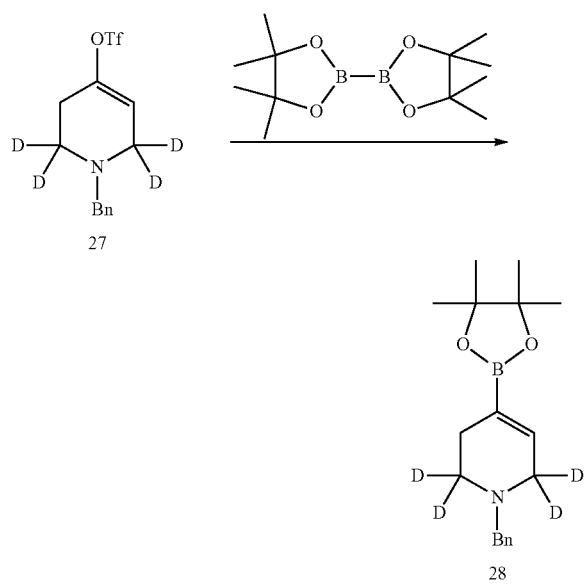

Compound 1-benzyl-1,2,3,6-(2,2,6,6-d₄-tetrahydropyridin)-4-yl trifluoromethanesulfonate (85 mg, 0.26 mmol) and dioxane (3 ml) were added into a flask successively. Under nitrogen protection, bis(pinacolato)diboron (73 mg, 0.29 mmol), Pd₂(dba)₃ (10 mg), PCy₃ (8 mg) and potassium acetate (38 mg, 0.39 mmol) were added with stirring. The reaction mixture was heated to 80° C., and stirred overnight. Water and dichloromethane were added for extraction; the oil phase was dried over anhydrous sodium sulfate, and concentrated. The crude product was purified by TLC prep plate to obtain the desired product as offwhite solid (56 mg, 75% yield).

9. Preparation of 1-benzyl-2,2,6,6-d₄-4-(5-(2-d-prop-2-yl)oxyl-2-methyl-4-nitrophenyl)-1,2,3,6-tetrahydropyridine

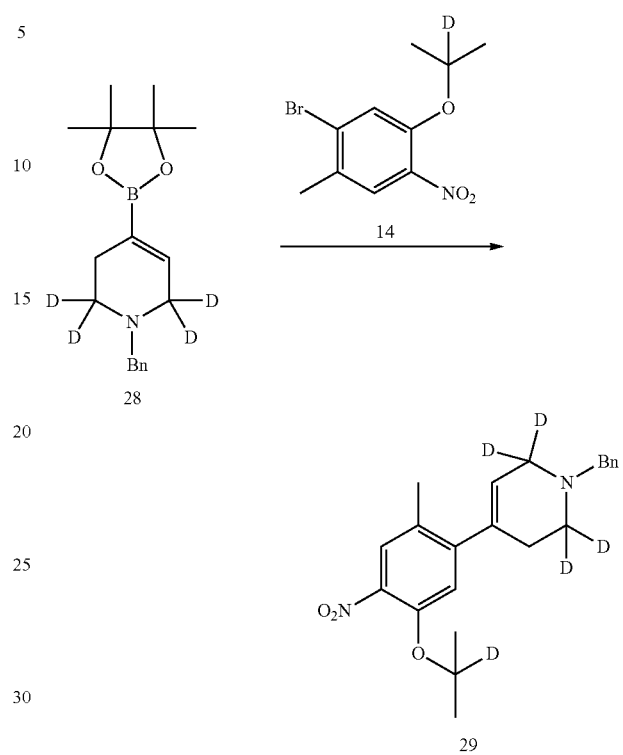

Under nitrogen, compound 1-bromo-5-(2-d-prop-2-yl)oxy-2-methyl-4-nitrobenzene (0.24 g, 0.87 mmol), 1-benzyl-2,2,6,6-d₄-4-(4,4,5,5-tetramethyl-1,3,2-dioxaborolan-2-yl)-1,2,3,6-tetrahydropyridine (0.35 g, 1.13 mmol), palladium acetate (18 mg, 0.078 mmol), 4,5-bisdiphenyl phosphine-9,9-dimethyl-xanthene (35 mg, 0.061 mmol), potassium phosphate trihydrate (0.59 g, 2.62 mmol) and tetrahydrofuran (8 ml) were added to a flask. Upon addition, the reaction mixture was heated to 85° C. and kept overnight. Into the reaction mixture was added water, and extracted with ethyl acetate for three times. The combined organic phase was washed successively with water and brine, dried over anhydrous sodium sulfate, and concentrated to give a crude product. The crude product was purified by preparative TLC to give the desired product (0.24 g, yield: 75%). MS Calcd.: 371; MS Found: 372 (M+H)⁺.

10. Preparation of 2-((2-d-prop-2-yl) oxyl)-5-methyl-4-(2,2,6,6-d₄-piperidin-4-yl) aniline dihydrochloride

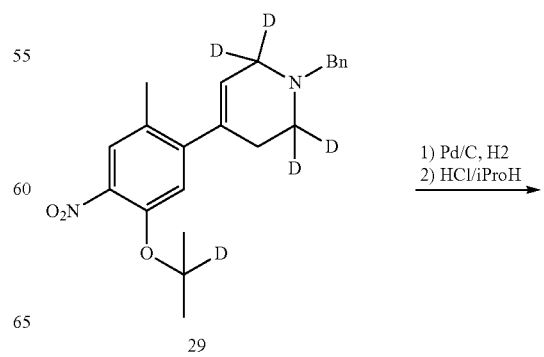

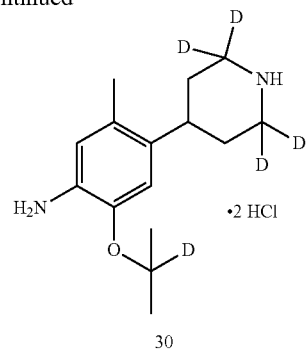

Compound 1-benzyl-2,2,6,6-d4-4-(5-(2-d-prop-2-yl) oxy-2-methyl-4-nitrophenyl)-1,2,3,6-tetrahydropyridine (0.22 g, 0.59 mmol), palladium on carbon (0.022 g, 50% palladium content) and methanol (8 ml) were added into a flask, and replaced with hydrogen for three times. The reaction mixture was heated to 45° C. and kept for 40 hours. Palladium on carbon was removed by filtration; the filtrate was concentrated to obtain a gray solid. The obtained gray solid and hydrochloric acid solution in isopropanol (2M, 2 ml) were sequentially added to the flask and stirred for 2 h. The reaction solution was concentrated under reduced pressure to obtain the desired product as a white solid (0.18 g, yield: 95%).

11. Preparation of 2,5-dichloro-N-(2-(isopropylsulfonyl)phenyl)pyrimidin-4-amine

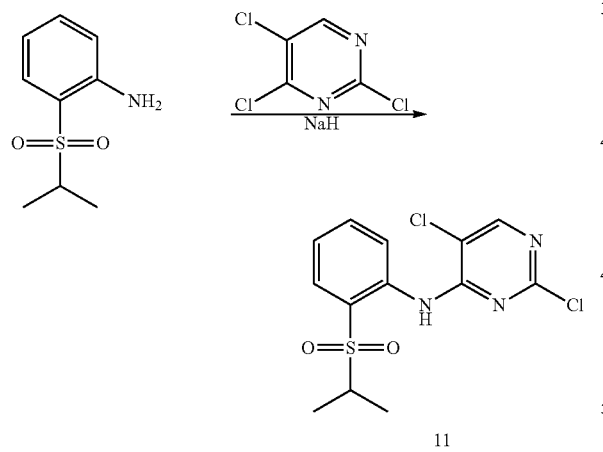

Under the protection of nitrogen, 2-(isopropylsulfonyl) aniline (0.65 g, 3.29 mmol) and anhydrous N, N-dimethylformamide (6 mL) was sequentially added into a flask, cooled to 0° C., and sodium hydride (0.20 g, 60%, 8.24 mmol) was added in batches. Upon addition, the reaction mixture was stirred for 1 hour. 2,4,5-trichloropyrimidine (1.21 g, 6.59 mmol) in N, N-dimethylformamide (3 mL) was added dropwise, and then heated to room temperature and stirred overnight. The reaction mixture was added into pure water to quench the reaction. Then it was extracted with ethyl acetate for three times. The organic layers were combined, and washed with water and brine successively, dried over anhydrous sodium sulfate, filtered and concentrated by a rotary evaporator under vacuo to give a crude product. The crude product was purified by column chromatography to give the desired product as white solid (0.70 g, 63%). MS Calcd.: 345; MS Found: 346 (M+H)+, 368 (M+Na)+. $^1$HNMR (CDCl$_3$, 400 MHz) δ 10.08 (s, 1H), 8.65 (d, J=8.4 Hz, 1H), 8.32 (s, 1H), 7.94 (d, J=8.0 Hz, 1H), 7.75 (t, J=8.4 Hz, 1H), 7.33 (t, J=8.0 Hz, 1H), 3.25-3.12 (m, 1H), 1.34 (d, 6H).

12. Preparation of 5-chloro-N$^2$-(2-(2-d-prop-2-yloxyl)-5-methyl-4-(2,2,6,6-d$_4$-piperidin-4-yl)phenyl)-N$^4$-(2-(isopropylsulfonyl)phenyl)pyrimidine-2,4-diamine

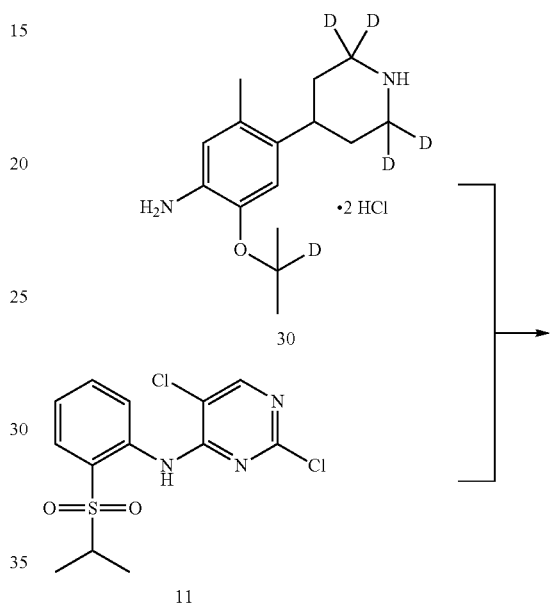

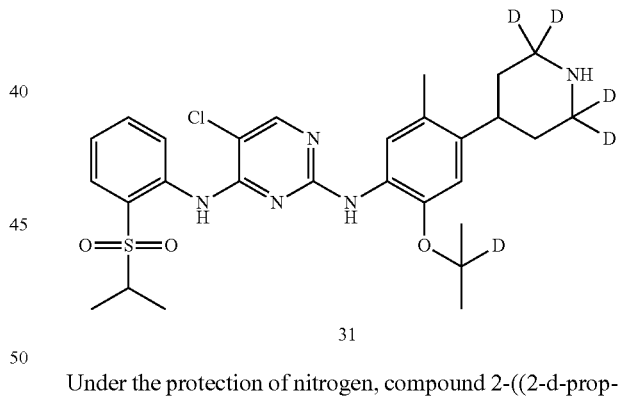

Under the protection of nitrogen, compound 2-((2-d-prop-2-yl) oxyl)-5-methyl-4-(2,2,6,6-d$_4$-piperidin-4-yl) aniline dihydrochloride (0.180 g, 0.52 mmol), 2,5-dichloro-N-(2-(isopropylsulfonyl) phenyl) pyrimidin-4-amine (0.198 g, 0.57 mmol) and isopropanol (4 ml) were added into a flask, warmed to 85° C. and kept overnight. The reaction was monitored as being substantially completed by HPLC, cooled to room temperature, and stirred for 3 hours to precipitate the solid. The solid was filtered, and the filter cake was beating washed with cold isopropanol to give the desired product hydrochloride. The hydrochloride was dissolved in pure water, an aqueous solution of sodium carbonate was added dropwise slowly to neutralize the pH to 8.5, and then extracted with ethyl acetate. The combined organic phase was dried over anhydrous sodium sulfate, and concentrated to give the desired product as a white solid (0.176 g, yield: 60%). MS Calcd.: 562; MS Found: 563

(M+H)⁺, 585 (M+Na)⁺. ¹HNMR (DMSO-d₆+D₂O, 400 MHz) δ 8.49 (d, J=7.6 Hz, 1H), 8.23 (s, 1H), 7.80-7.78 (dd, J=7.6, 2.0 Hz, 1H), 7.46 (t, J=7.6 Hz, 1H), 7.30 (s, 1H), 7.26 (t, J=7.6 Hz, 1H), 6.88 (s, 1H), 3.45-3.38 (m, 1H), 3.02-2.98 (m, 1H), 2.32 (s, 3H), 1.77-1.63 (m, 4H), 1.18 (d, 6H), 1.12 (s, 6H).

Example 3

Preparation of 5-chloro-N²-(2-(2-d-prop-2-yloxyl)-5-methyl-4-(2,2,6,6-d₄-piperidin-4-yl) phenyl)-N⁴-(2-((2-d-prop-2-yl) sulfonyl) phenyl) pyrimidine-2,4-diamine

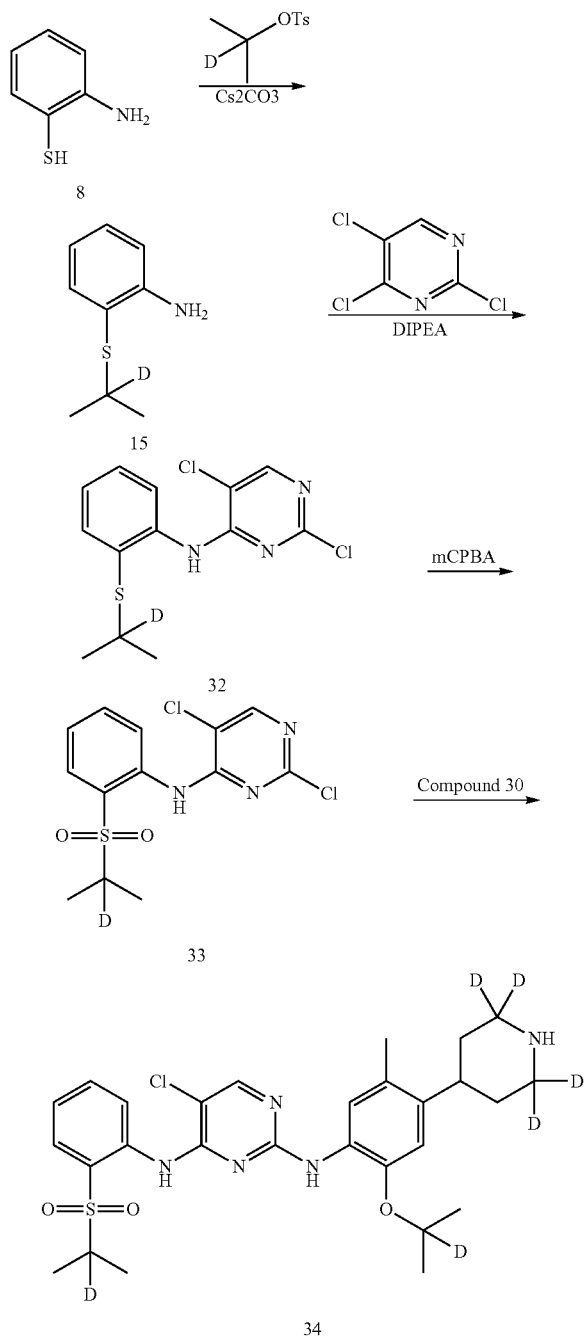

1. Preparation of 2-((2-d-prop-2-yl)thio) aniline (Compound 15)

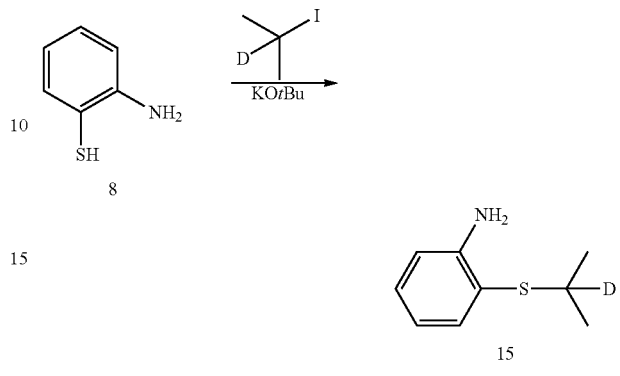

Under the protection of nitrogen, compound 2-aminothiophenol (0.5 g, 4 mmol), 2-iodo-2-d-propane (0.75 g, 4.4 mmol) and ethanol (5 mL) were successively added to a flask. Under stirring, potassium tert-butoxide (0.59 g, 5.2 mmol) was slowly added at 0° C. It was warmed to room temperature and kept for 4 hours. The reaction was monitored as being substantially completed by HPLC. The reaction mixture was filtered through Celite, the filter cake was washed with ethanol and the combined filtrate was concentrated in vacuo by rotary evaporator. The residue was dissolved in ethyl acetate (20 mL), washed with water and brine successively, dried over anhydrous sodium sulfate, filtered and concentrated by a rotary evaporator under vacuo to give a crude product. The crude product was purified by silica gel column chromatography to give the desired product as yellowish oil. MS Calcd.: 168; MS Found: 169 (M+H)⁺.

Compound 15 can also be prepared by the following routes:

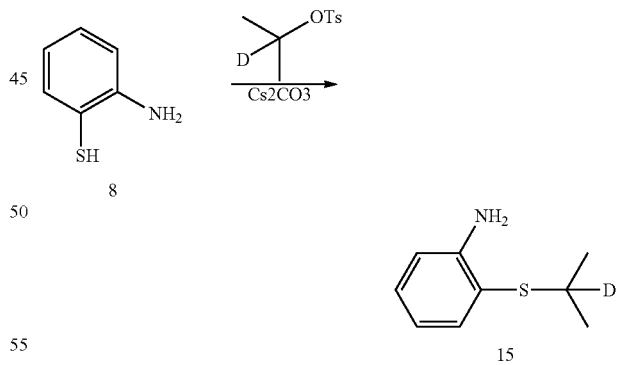

Under the protection of nitrogen, compound 2-aminothiophenol (0.105 g, 0.84 mmol), p-toluenesulfonic-2-d-isopropyl ester (150 mg, 0.70 mmol), cesium carbonate (0.681 g, 2.09 mmol) and N, N-dimethylformamide (5 mL) were added into a flask successively, warmed to 60° C. and kept for 20 hours. The reaction was monitored as being completed by HPLC. Into the reaction mixture was added pure water to quench the reaction. Then the reaction mixture was extracted with ethyl acetate for three times. The organic layers were dried over anhydrous sodium sulfate, filtered and concentrated by a rotary evaporator under vacuo to give a crude product. The crude product was purified by TLC chromatography to give the desired product as slightly yellowish oil. ¹HNMR (CDCl₃, 400 MHz) δ 7.37-7.35 (dd, J=7.6, 2.0 Hz, 1H), 7.12 (t, J=7.6 Hz, 1H), 6.74-6.72 (dd, J=7.6, 2.0 Hz, 1H), 6.67 (t, J=7.6 Hz, 1H), 4.42 (broad, 2H), 1.23 (s, 6H).

2. Preparation of 2,5-dichloro-N-(2-((2-d-prop-2-yl)thio)phenyl)pyrimidin-4-amine

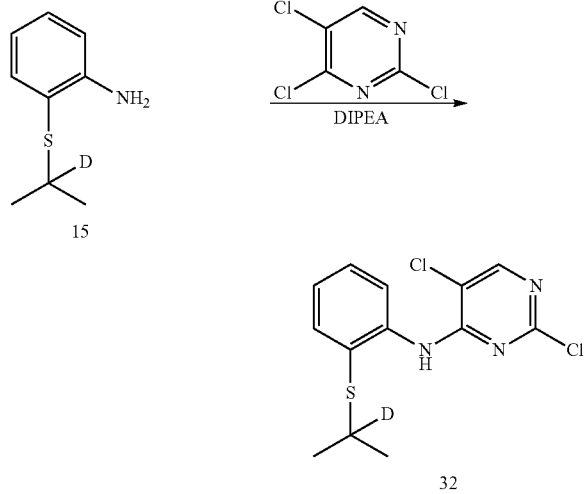

Compound 2-((2-d-prop-2-yl) thio) aniline (137 mg, 0.81 mmol), 2,4,5-trichloropyrimidine (299 mg, 1.63 mmol), diisopropyl ethylamine (157 mg, 1.22 mmol) and n-butanol (4 mL) were added into a flask successively, heated to 100° C. and kept for 20 hours. The reaction mixture was concentrated, and then pure water was added. The obtained mixture was extracted with ethyl acetate for three times. The combined organic layer was dried over anhydrous sodium sulfate, filtered and concentrated by a rotary evaporator under vacuo to give a crude product. The crude product was purified by TLC to give the desired product as a faint yellow solid (128 mg, yield 50%). ¹HNMR (CDCl₃, 400 MHz) δ 9.31 (s, 1H), 8.69-8.67 (dd, J=8.4, 1.2 Hz, 1H), 8.26 (s, 1H), 7.62-7.60 (dd, J=7.6, 1.6 Hz, 1H), 7.48 (t, J=8.8 Hz, 1H), 7.15-7.11 (t, J=8.8 Hz, 1H), 1.29 (s, 6H).

3. Preparation of 2,5-dichloro-N-(2-((2-d-prop-2-yl) sulfonyl) phenyl) pyrimidin-4-amine

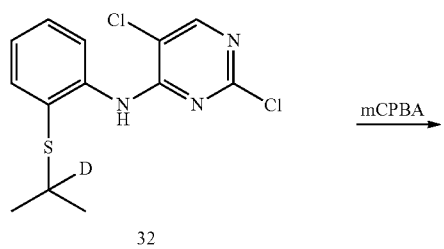

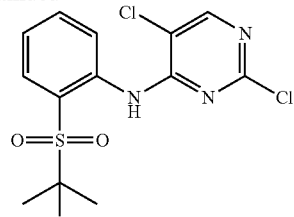

Compound 2,5-dichloro-N-(2-((2-d-prop-2-yl) thio) phenyl) pyrimidin-4-amine (290 mg, 0.92 mmol), 3-chloro peroxybenzoic acid (476 mg, 85%, 2.76 mmol) and dichloromethane (6 mL) were added into a flask successively, heated to 40° C. and kept for 4 hours. The reaction was monitored as being substantially completed by HPLC. Into the reaction mixture was added 5% sodium bicarbonate solution, and then pure water was added. The obtained mixture was extracted with dichloromethane for three times. The combined organic layer was dried over anhydrous sodium sulfate, filtered and concentrated by a rotary evaporator under vacuo to give a crude product. The crude product was purified by TLC to give the desired product as a white solid (307 mg, yield 96%). ¹HNMR (CDCl₃, 400 MHz) δ 10.08 (s, 1H), 8.65 (d, J=7.6 Hz, 1H), 8.32 (s, 1H), 7.95-7.93 (dd, J=8.0, 1.6 Hz, 1H), 7.75 (t, J=8.4 Hz, 1H), 7.34 (t, J=8.0 Hz, 1H), 1.33 (s, 6H).

4. Preparation of 5-chloro-N²-(2-(2-d-prop-2-yloxy)-5-methyl-4-(2,2,6,6-d₄-piperidin-4-yl) phenyl)-N⁴-(2-((2-d-prop-2-yl) sulfonyl) phenyl) pyrimidine-2,4-diamine

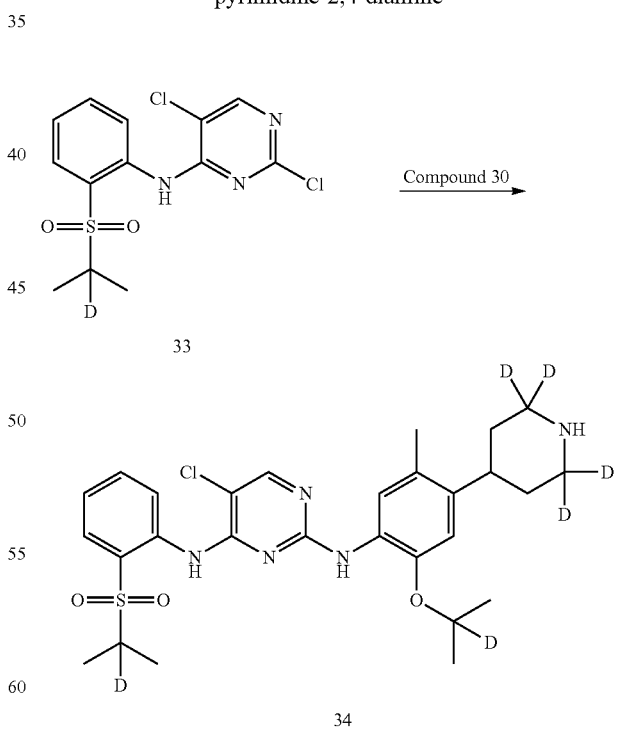

Under the protection of nitrogen, compound 2-((2-d-prop-2-yl) oxyl)-5-methyl-4-(2,2,6,6-d₄-piperidin-4-yl) aniline dihydrochloride (0.124 g, 0.43 mmol), 2,5-dichloro-N-(2-((2-d-prop-2-yl) sulfonyl) phenyl) pyrimidin-4-amine (0.164 g, 0.473 mmol) and isopropanol (3 ml) were added into a flask, warmed to 85° C. and kept for 20 h. After cooled to room temperature, into the reaction mixture was added pure water, and aqueous sodium carbonate solution was added to neutralize the pH to 8.5. The obtained mixture was extracted with ethyl acetate for three times. The organic layers were combined, dried over anhydrous sodium sulfate and concentrated to give a crude product. The crude product was purified by preparative TLC (developing solvent: methanol/dichloromethane=1/9, v/v) to obtain the desired product as a white solid (0.070 g, yield: 30%). MS Calcd.: 563; MS Found: 564 (M+H)$^+$, 586 (M+Na)$^+$. $^1$HNMR (DMSO-d$_6$+D$_2$O, 400 MHz) δ 8.50 (d, J=7.6 Hz, 1H), 8.22 (s, 1H), 7.80-7.78 (dd, J=7.6, 2.0 Hz, 1H), 7.46 (t, J=7.6 Hz, 1H), 7.30 (s, 1H), 7.26 (t, J=7.6 Hz, 1H), 6.89 (s, 1H), 3.00-2.98 (m, 1H), 2.34 (s, 3H), 1.77-1.63 (m, 4H), 1.23 (s, 6H), 1.12 (s, 6H).

Example 4

Preparation of 5-chloro-N$^2$-(2-isopropoxy-5-methyl-4-(2,2,6,6-d$_4$-piperidin-4-yl) phenyl)-N$^4$-(2-((2-d-prop-2-yl)sulfonyl)phenyl)pyrimidine-2,4-diamine

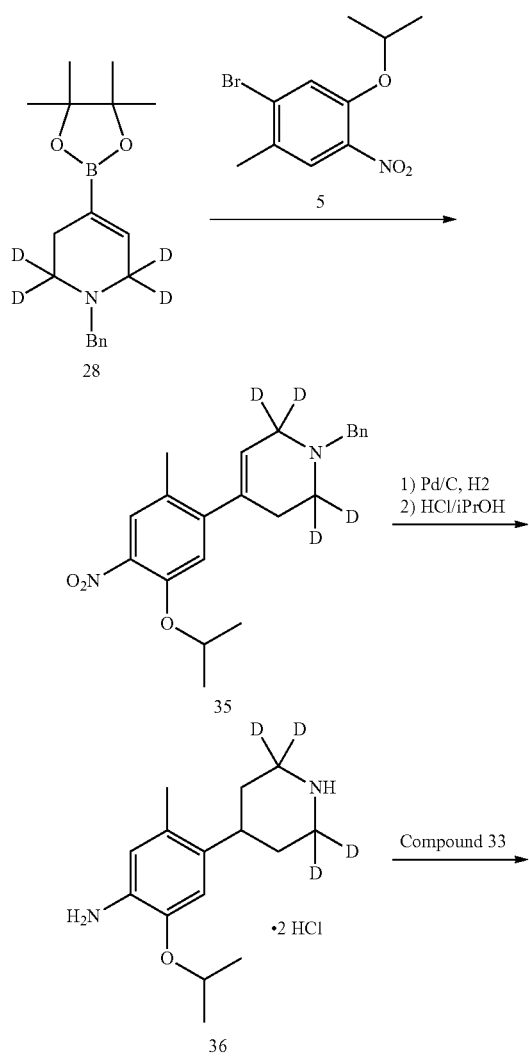

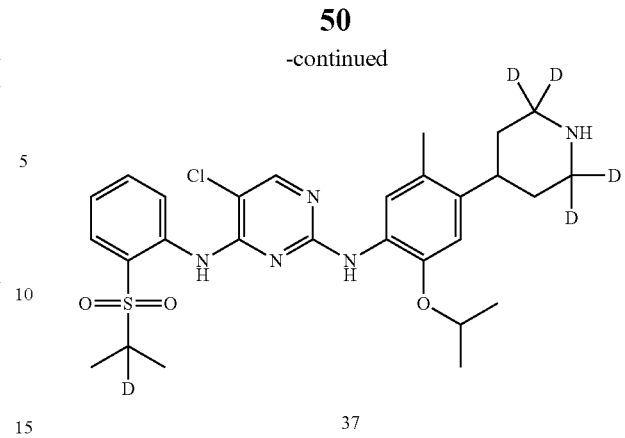

1. Preparation of 1-benzyl-2,2,6,6-d$_4$-4-(5-isopropoxy-2-methyl-4-nitrophenyl)-1,2,3,6-tetrahydropyridine

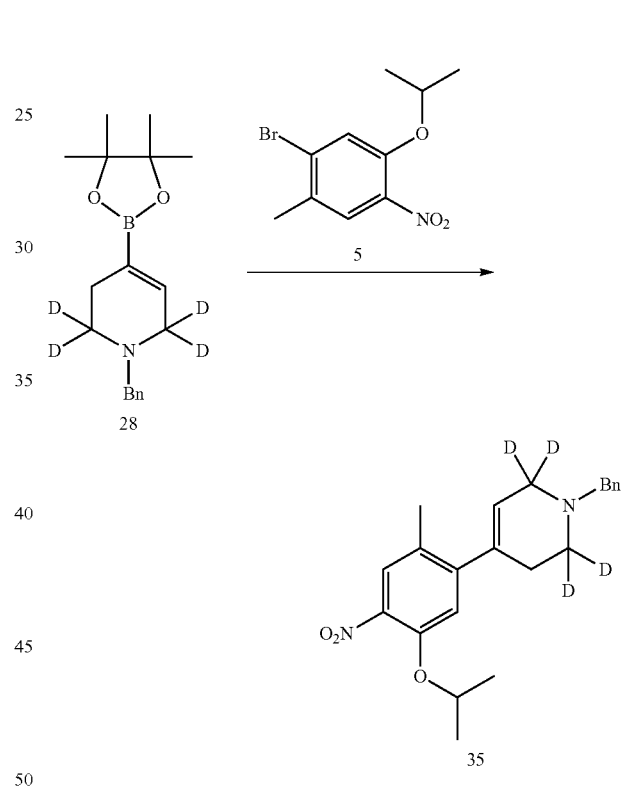

Under the protection of nitrogen, compound 1-bromo-5-isopropoxy-2-methyl-4-nitrobenzene (0.30 g, 1.09 mmol), 1-benzyl-2,2,6,6-d$_4$-4-(4,4,5,5-tetramethyl-1,3,2-dioxaborolan-2-yl)-1,2,3,6-tetrahydropyridine (0.43 g, 1.42 mmol), palladium acetate (22 mg, 0.098 mmol), 4,5-bis-diphenyl phosphine-9,9-dimethyl-xanthene (45 mg, 0.076 mmol), potassium phosphate trihydrate (0.74 g, 3.27 mmol) and tetrahydrofuran (6 ml) were added to a flask, and then heated to 85° C. and kept overnight. Into the reaction mixture was added pure water to quench the reaction, and the obtained mixture was extracted with ethyl acetate. The combined organic phase was washed successively with water and brine, dried over anhydrous sodium sulfate, and concentrated to give a crude product. The crude product was purified by preparative TLC to give the desired product (0.30 g, yield: 75%). MS Calcd.: 370; MS Found: 371 (M+H)$^+$.

2. Phe preparation of 2-isopropoxy-5-methyl-4-(2,2,6,6-d4-piperidin-4-yl) aniline dihydrochloride

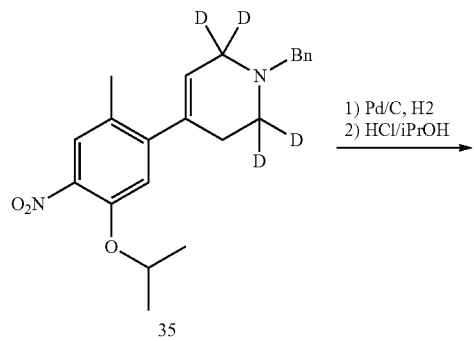

35

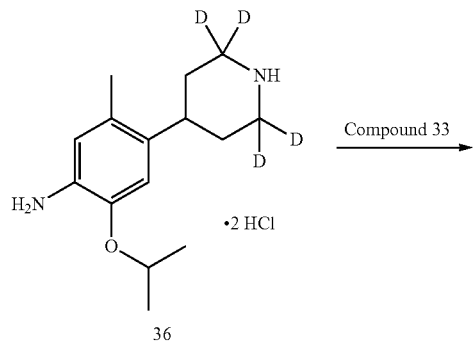

36

Compound 1-benzyl-2,2,6,6-d4-4-(5-isopropoxy-2-methyl-4-nitrophenyl)-1,2,3,6-tetrahydropyridine (0.30 g, 0.81 mmol), palladium on carbon (0.03 g, 50% palladium content) and methanol (10 ml) were added into a flask. The system was replaced with hydrogen for three times, heated to 45° C. and kept for 40 hours. Palladium on carbon was removed by filtration; the filtrate was concentrated to obtain a gray solid. The obtained gray solid and hydrochloric acid solution in isopropanol (2M, 2 ml) were sequentially added to a flask and stirred for 2 h. The reaction solution was concentrated under reduced pressure to obtain the desired product as a white solid (0.26 g, yield: 94%).

3. Preparation of 5-chloro-$N^2$-(2-isopropoxy-5-methyl-4-(2,2,6,6-d4-piperidin-4-yl) phenyl)-$N^4$-(2-((2-d-prop-2-yl) sulfonyl) phenyl) pyrimidine-2,4-diamine

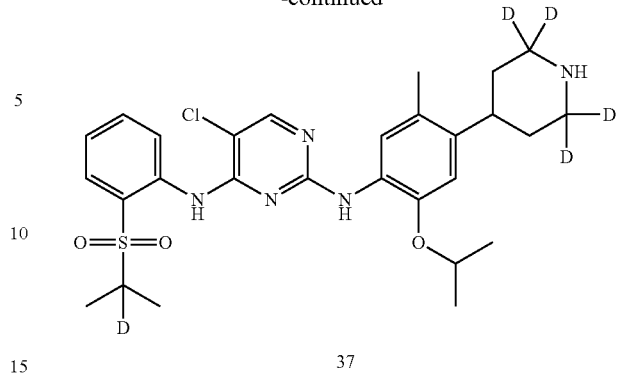

37

Under the protection of nitrogen, compound 2-isopropoxy-5-methyl-4-(2,2,6,6-d4-piperidin-4-yl) aniline dihydrochloride (0.17 g, 0.52 mmol), 2,5-dichloro-N-(2-((2-d-prop-2-yl) sulfonyl) phenyl) pyrimidin-4-amine (0.20 g, 0.57 mmol) and isopropanol (5 ml) were added into a flask, warmed to 85° C. and kept overnight. After cooled to room temperature, into the reaction mixture was added water to quench the reaction, and aqueous sodium carbonate solution was added to neutralize the pH to 8.5. The obtained mixture was extracted with ethyl acetate. The organic layer was combined, dried over anhydrous sodium sulfate and concentrated to give a crude product. The crude product was purified by TLC (developing solvent: methanol/dichloromethane=1/9, v/v) to obtain the desired product as a white solid (0.10 g, yield: 35%). MS Calcd.: 562; MS Found: 563 (M+H)$^+$, 585 (M+Na)$^+$. $^1$HNMR (DMSO-d$_6$+D$_2$O, 400 MHz) δ 8.50 (d, J=7.6 Hz, 1H), 8.22 (s, 1H), 7.80-7.78 (dd, J=7.6, 2.0 Hz, 1H), 7.46 (t, J=7.6 Hz, 1H), 7.30 (s, 1H), 7.26 (t, J=7.6 Hz, 1H), 6.88 (s, 1H), 4.52-4.48 (m, 1H), 3.00-2.97 (m, 1H), 2.32 (s, 3H), 1.77-1.63 (m, 4H), 1.22 (s, 6H), 1.12 (d, 6H).

Example 5

Preparation of 5-chloro-$N^2$-(2-(2-d-prop-2-yloxy)-5-(d$_3$-methyl)-4-(2,2,6,6-d4-piperidin-4-yl)phenyl)-$N^4$-(2-((2-d-prop-2-yl)sulfonyl)phenyl)pyrimidine-2,4-diamine

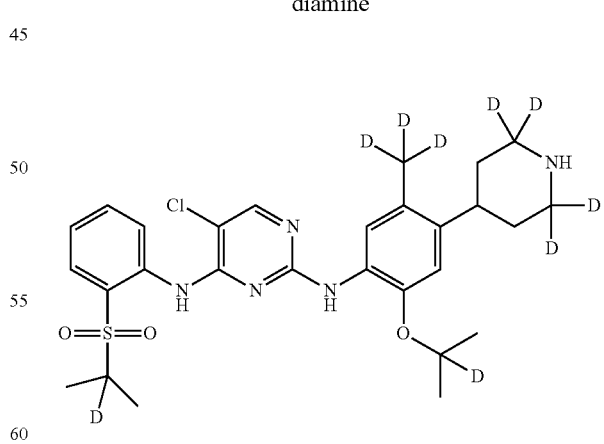

The experiment was conducted according to the method of example 1, except that: 1-bromo-5-(2-d-prop-2-yloxyl)-2-methyl-4-nitrobenzene (compound 14) and 2-((2-d-prop-2-yl)thio)aniline (compound 15) were used to replaced 1-bromo-5-isopropoxy-2-methyl-4-nitrobenzene (compound 5) and 2-(isopropylthio) aniline (compound 9) respectively, and 1-bromo-5-fluoro-2-(d$_3$-methyl)-4-nitrobenzene was used instead of 1-bromo-5-fluoro-2-methyl-4-nitrobenzene (compound 4) to obtain the target compound.

Example 6

Preparation of 5-chloro-N²-(2-isopropoxy-5-methyl-4-(2,2,6,6-d₄-piperidin-4-yl) phenyl)-N⁴-(2-((2-d-prop-2-yl)sulfonyl)phenyl)pyrimidine-2,4-diamine

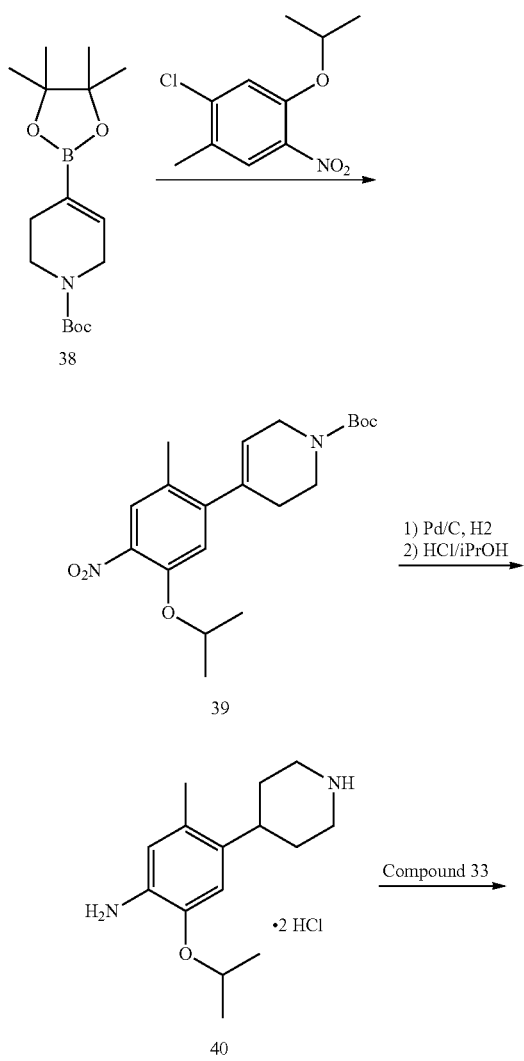

1. Preparation of tert-butyl-4-(5-isopropoxy-2-methyl-4-nitro phenyl)-5,6-dihydropyridine-1(2H)-carboxylate

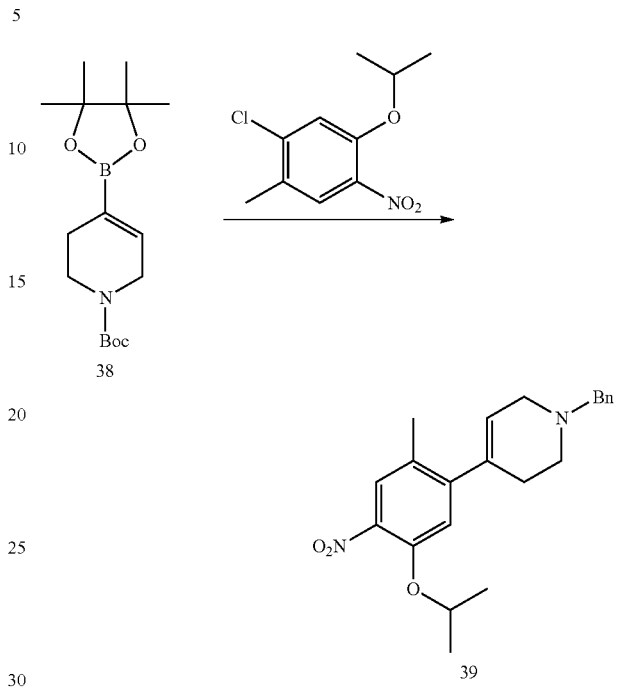

Under the protection of nitrogen, compound 1-chloro-5-isopropoxy-2-methyl-4-nitrobenzene (0.245 g, 1.07 mmol), 3,6-dihydro-2H-pyridine-1-t-butoxycarbonyl-boronic acid pinacol ester (0.495 g, 1.60 mmol), palladium acetate (22 mg, 0.096 mmol), 4,5-bisdiphenyl phosphine-9,9-dimethylxanthene (43 mg, 0.075 mmol), potassium phosphate trihydrate (0.73 g, 3.20 mmol) and tetrahydrofuran (10 ml) were added into a flask, and then heated to 85° C. and kept overnight. The reaction mixture was added with pure water to quench the reaction, and extracted with ethyl acetate for three times. The combined organic phase was washed successively with water and brine, dried over anhydrous sodium sulfate, and concentrated to give a crude product. The crude product was purified by TLC to give the desired product as a colorless clear liquid (0.29 g, yield 73%). ¹HNMR (CDCl₃, 400 MHz) δ 7.63 (s, 1H), 6.80 (s, 1H), 5.62 (m, 1H), 4.65-4.62 (m, 1H), 4.08 (m, 2H), 3.65 (t, 2H), 2.34 (m, 2H), 2.25 (s, 3H), 1.52 (s, 9H), 1.39 (d, 6H).

2. Preparation of 2-isopropoxy-5-methyl-4-(piperidin-4-yl) aniline dihydrochloride

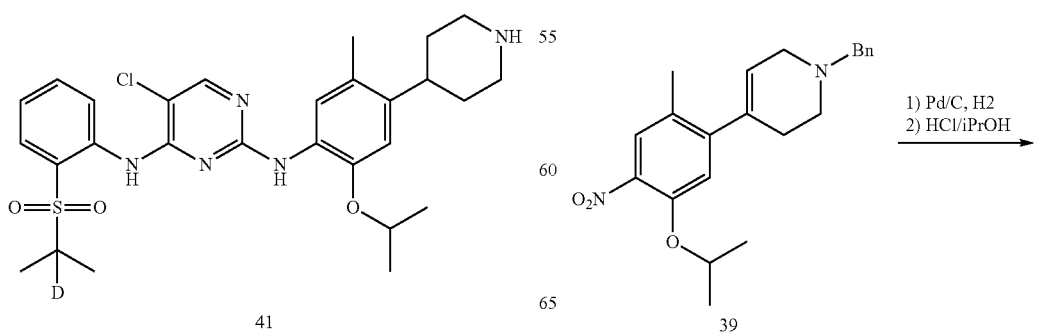

-continued

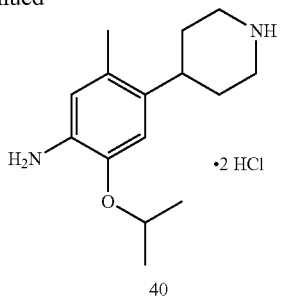

40

Compound tert-butyl 4-(5-isopropoxy-2-methyl-4-nitrophenyl)-5,6-dihydropyridine-1(2H)-carboxylate (0.29 g, 0.77 mmol), palladium on carbon (0.03 g, 50% palladium content) and methanol (10 ml) were added into a flask. The reaction system was replaced with hydrogen for three times, heated to 45° C. and kept overnight. Palladium on carbon was removed by filtration; and the filtrate was concentrated to obtain a pink solid. $^1$HNMR (CD$_3$OD, 400 MHz) δ 6.66 (s, 1H), 6.61 (s, 1H), 4.51-4.48 (m, 1H), 4.23-4.20 (m, 2H), 2.87-2.79 (m, 3H), 2.22 (s, 3H), 1.73-1.70 (m, 2H), 1.54-1.47 (m, 11H), 1.32 (d, 6H).

The pink solid and hydrochloride solution in isopropanol (2M, 2 ml) were successively added into a flask, heated to 55° C. and kept for 2 h. The reaction was monitored as being completed by HPLC. The reaction solution was concentrated under reduced pressure to obtain the desired product as a white solid (0.23 g, yield: 94%).

3. Preparation of 5-chloro-N$^2$-(2-isopropoxy-5-methyl-4-(piperidin-4-yl) phenyl)-N$^4$-(2-((2-d-prop-2-yl) sulfonyl) phenyl)pyrimidine-2,4-diamine

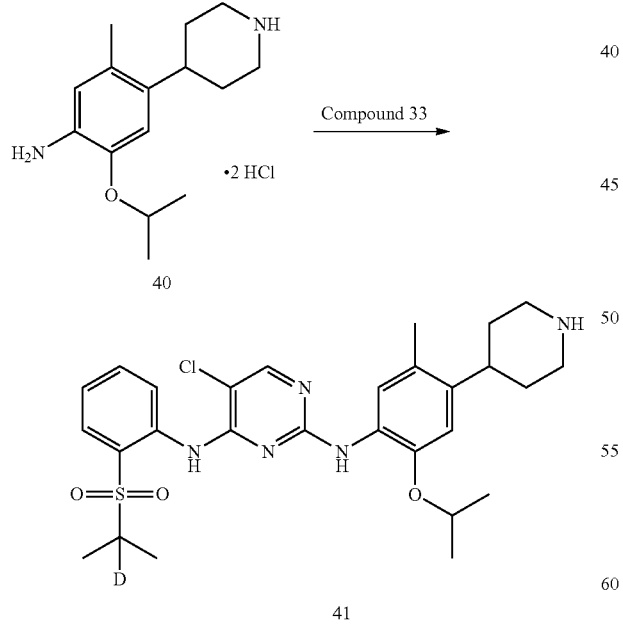

Under the protection of nitrogen, compound 2-isopropoxy-5-methyl-4-(piperidin-4-yl) aniline dihydrochloride (0.10 g, 0.31 mmol), 2,5-dichloro-N-(2-((2-d-prop-2-yl) sulfonyl) phenyl) pyrimidin-4-amine (0.12 g, 0.34 mmol) and isopropanol (3 ml) were added into a flask, warmed to 85° C. and kept overnight. After cooled to room temperature, into the reaction mixture was added pure water to quench the reaction, and aqueous sodium carbonate solution was added to neutralize the pH to 8.5. The obtained mixture was extracted with ethyl acetate. The organic layers were combined, dried over anhydrous sodium sulfate and concentrated to give a crude product. The crude product was purified by TLC (developing solvent: methanol/dichloromethane=1/9, v/v) to obtain the desired product as a white solid (0.054 g, yield: 31%). MS Calcd.: 558; MS Found: 559 (M+H)$^+$, 581 (M+Na)$^+$. $^1$HNMR (DMSO-d$_6$+D2O, 400 MHz) δ 8.48 (d, J=7.6 Hz, 1H), 8.20 (s, 1H), 7.79-7.77 (dd, J=7.6, 2.0 Hz, 1H), 7.46 (t, J=7.6 Hz, 1H), 7.29 (s, 1H), 7.26 (t, J=7.6 Hz, 1H), 6.86 (s, 1H), 4.52-4.48 (m, 1H), 3.30-3.28 (m, 2H), 3.00-2.91 (m, 3H), 2.30 (s, 3H), 1.77-1.63 (m, 4H), 1.22 (s, 6H), 1.12 (d, 6H).

Example 7

5-chloro-N$^2$-(2-isopropoxy-5-methyl-4-(piperidin-4-yl) phenyl)-N$^4$-(2-((d$_7$-isopropyl) sulfonyl) phenyl) pyrimidine-2,4-diamine

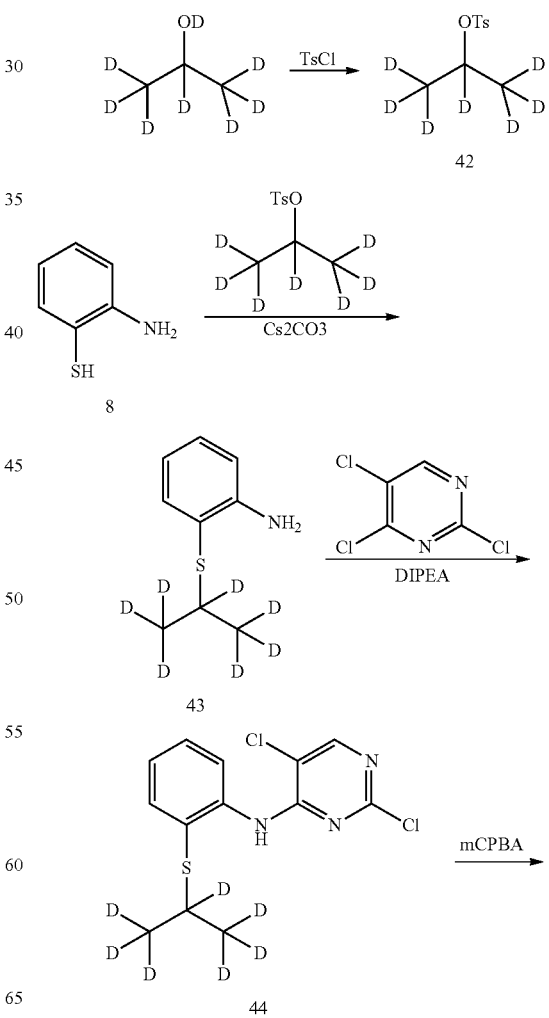

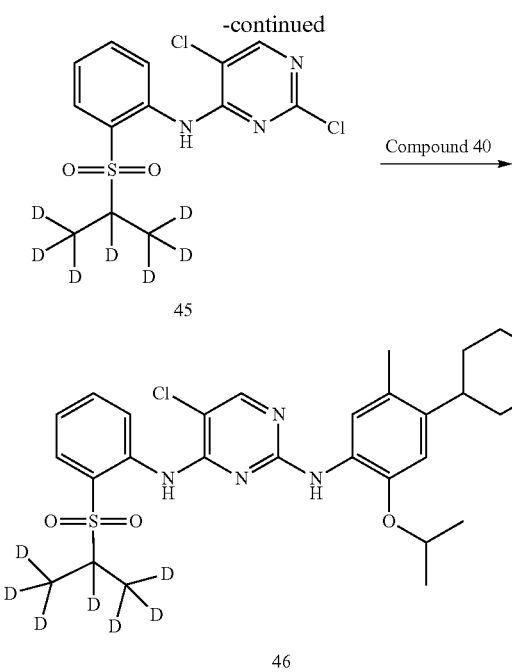

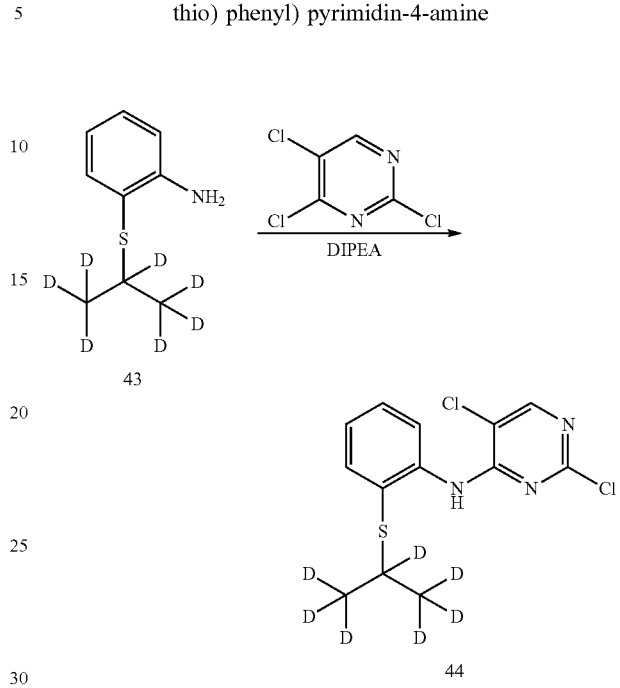

obtained by replacing p-toluene sulfonic acid-2-d-isopropyl with p-toluenesulfonic-$d_7$-isopropyl.

3. Preparation of 2,5-dichloro-N-(2-($d_7$-isopropyl-thio) phenyl) pyrimidin-4-amine The synthesis was conducted according to step 2 of example 3, and slightly yellowish oily target product was obtained by replacing 2-((2-d-prop-2-yl) thio) aniline with 2-($d_7$-isopropylthio) aniline.

4. Preparation of 2,5-dichloro-N-(2-($d_7$-isopropyl-sulfonyl) phenyl) pyrimidin-4-amine

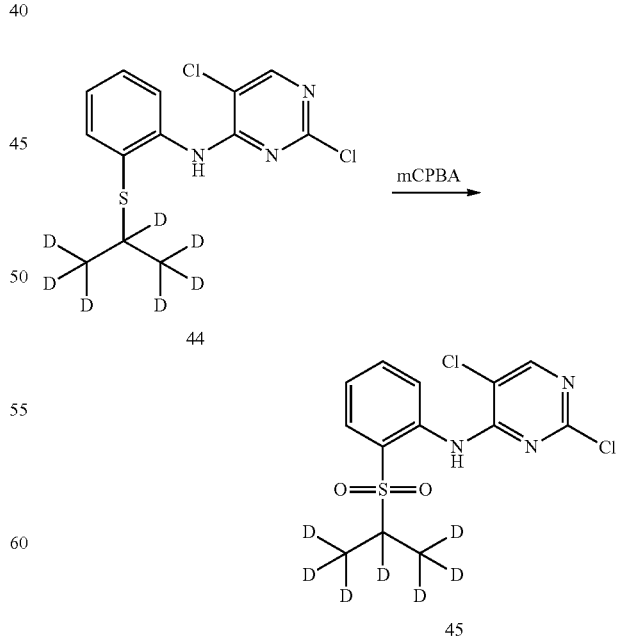

Compound 2,5-dichloro-N-(2-($d_7$-isopropylthio) phenyl) pyrimidin-4-amine (200 mg, 0.62 mmol), 3-chloro peroxy- 1. Preparation of $d_7$-isopropyl-4-methylbenzenesulfonate

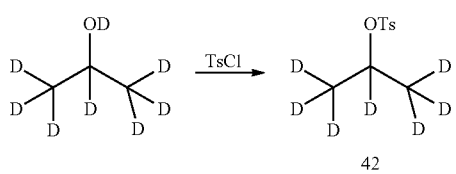

Compound $d_8$-isopropanol (1.0 g, 27.74 mmol), triethylamine (8.4 g, 83.22 mmol) and dichloromethane (150 ml) were added into a flask, warmed to 40° C. and kept for two days. The reaction liquid was added with water, and extracted with dichloromethane for three times. The combined organic phase was washed successively with aqueous sodium carbonate and water, dried over anhydrous sodium sulfate, and concentrated to give a crude product. The crude product was purified by column chromatography to give the desired product as white solid.

2. Preparation of 2-($d_7$-isopropylthio) aniline

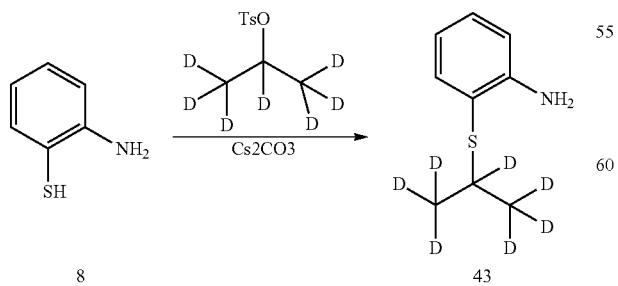

The synthesis was conducted according to step 1 of example 3, and slightly yellowish oily target product was benzoic acid (379 mg, 85%, 1.87 mmol) and methylene chloride (4 mL) were added into a flask successively, heated to 40° C. and kept for 6 hours. The reaction was monitored as being substantially completed by HPLC. Into the reaction mixture was added 5% sodium carbonate solution to neutralize to neutral, and then pure water was added. The obtained mixture was extracted with methylene chloride. The combined organic layers were dried over anhydrous sodium sulfate, filtered and concentrated by a rotary evaporator under vacuo to give a crude product. The crude product was purified by preparative TLC to give the desired product as a white solid (197 mg, yield 90%). $^1$HNMR (CDCl$_3$, 400 MHz) δ 10.05 (s, 1H), 8.65-8.62 (dd, J=8.4, 0.8 Hz, 1H), 8.30 (s, 1H), 7.96-7.93 (dd, J=8.0, 1.6 Hz, 1H), 7.73 (t, J=8.4 Hz, 1H), 7.34 (t, J=8.4 Hz, 1H).

5. 5-chloro-$N^2$-(2-isopropoxy-5-methyl-4-(piperidin-4-yl) phenyl)-$N^4$-(2-((d$_7$-isopropyl) sulfonyl) phenyl) pyrimidine-2,4-diamine

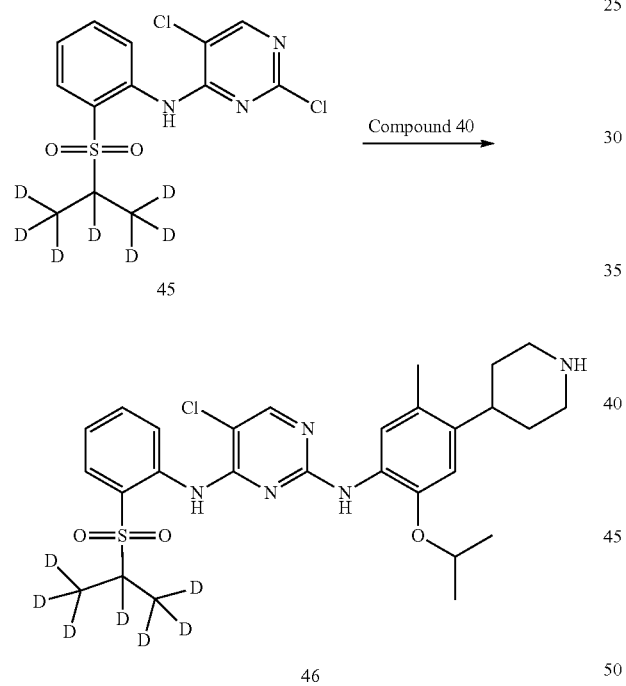

Under the protection of nitrogen, compound 2-isopropoxy-5-methyl-4-(piperidin-4-yl) aniline dihydrochloride (0.10 g, 0.31 mmol), 2,5-dichloro-N-(2-(d$_7$-isopropylsulfonyl) phenyl) pyrimidin-4-amine (0.12 g, 0.34 mmol) and isopropanol (3 ml) were added into a flask, warmed to 85° C. and kept overnight. After cooled to room temperature, into the reaction mixture was added pure water to quench the reaction, and aqueous sodium carbonate solution was added to neutralize the pH to 8.5. The obtained mixture was extracted with ethyl acetate. The organic layers were combined, dried over anhydrous sodium sulfate and concentrated to give a crude product. The crude product was purified by TLC (developing solvent: methanol/dichloromethane=1/9, v/v) to obtain the desired product as a white solid (0.063 g, yield: 36%). MS Calcd.: 564; MS Found: 565 (M+H)$^+$, 587 (M+Na)$^+$.

Example 8

5-chloro-$N^2$-((2-d-prop-2-yloxy)-5-methyl-4-(piperidin-4-yl) phenyl)-$N^4$- (2(isopropylsulfonyl) phenyl) pyrimidine-2,4-diamine

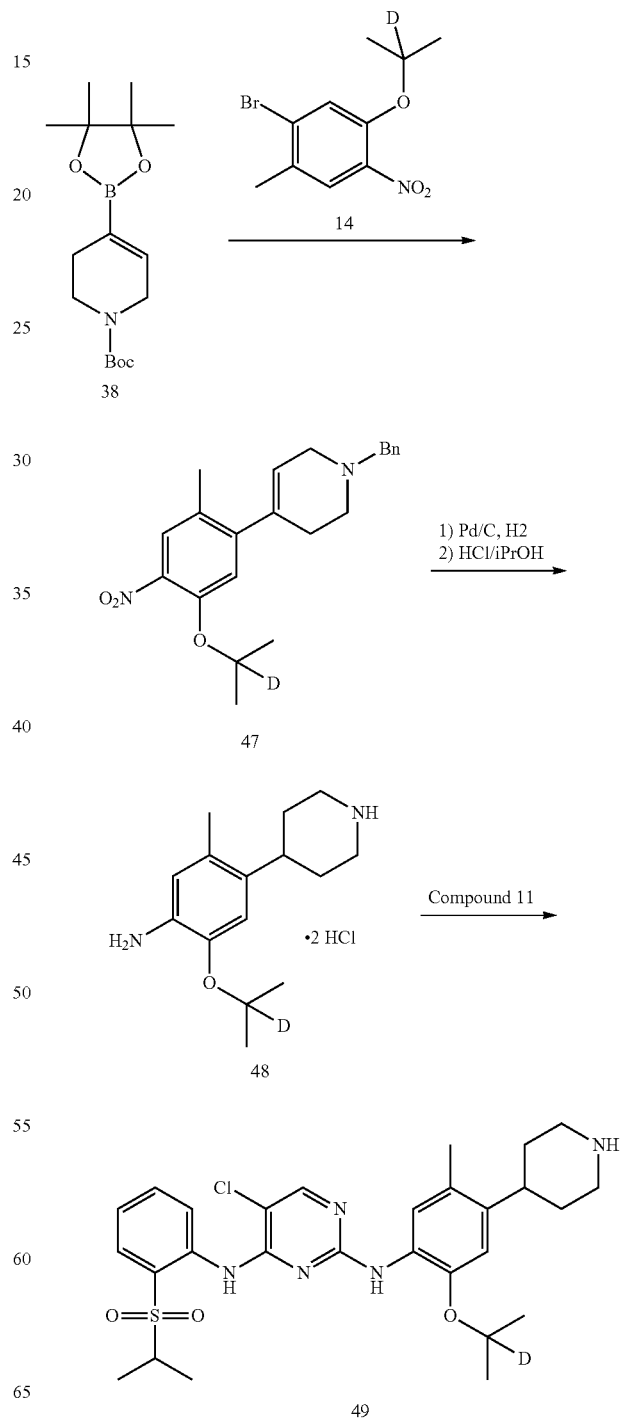

1. Preparation of tert-butyl 4-(5-(2-d-prop-2-yl)oxy-2-methyl-4-nitrophenyl)-5,6-dihydropyridine-1(2H)-carboxylate

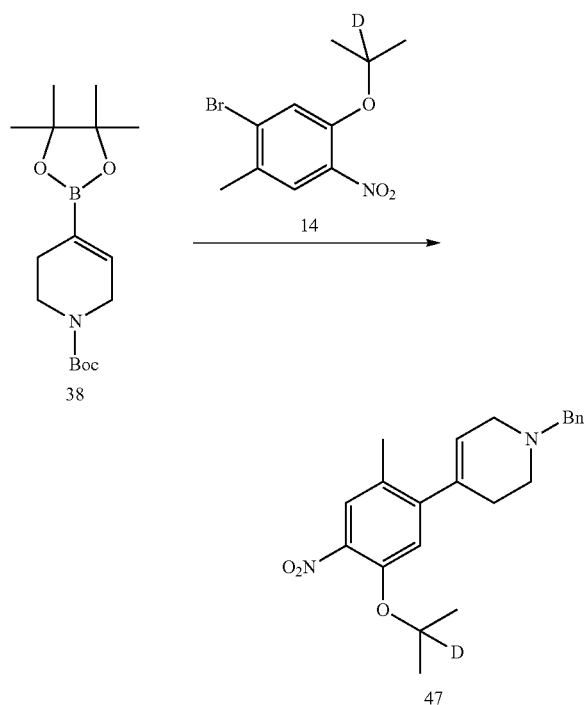

Under the protection of nitrogen, compound 1-bromo-5-(2-d-prop-2-yl)oxy-2-methyl-4-nitrobenzene (0.30 g, 1.09 mmol), 3,6-dihydro-2H-pyridine-1-t-butoxycarbonyl-boronic acid pinacol ester (0.51 g, 1.64 mmol), palladium acetate (22 mg, 0.098 mmol), 4,5-bisdiphenyl phosphine-9,9-dimethyl-xanthene (44 mg, 0.076 mmol), potassium phosphate trihydrate (0.74 g, 3.27 mmol) and tetrahydrofuran (10 ml) were added into a flask, and then heated to 85° C. and kept for 20 h. The reaction mixture was added with water, and extracted with ethyl acetate for three times. The combined organic phase was washed successively with water and brine, dried over anhydrous sodium sulfate, and concentrated to give a crude product. The crude product was purified by TLC to give the desired product as a colorless clear liquid (0.30 g, yield 73%). $^1$HNMR (CDCl$_3$, 400 MHz) δ, 7.60 (s, 1H), 6.88 (s, 1H), 5.62 (m, 1H), 4.05 (m, 2H), 3.63 (t, 2H), 2.33 (m, 5H), 1.52 (s, 9H), 1.41 (s, 6H).

2. Preparation of 2-((2-d-prop-2-yl) oxyl)-5-methyl-4-(piperidin-4-yl) aniline dihydrochloride

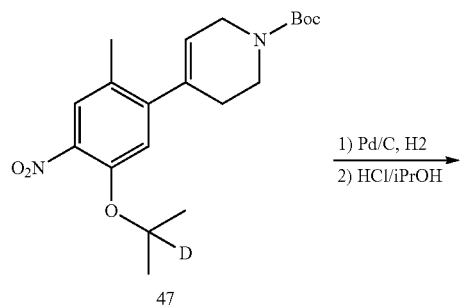

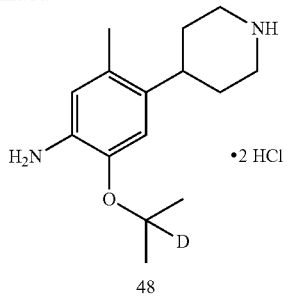

Compound tert-butyl 4-(5-(2-d-prop-2-yl) oxy-2-methyl-4-nitrophenyl)-5,6-dihydropyridine-1 (2H)-carboxylate (0.130 g, 0.34 mmol), palladium on carbon (0.013 g, 50% palladium content) and methanol (10 ml) were added into a flask. The reaction system was replaced with hydrogen for three times, heated to 45° C. and kept for 20 h. Palladium on carbon was removed by filtration; the filtrate was concentrated to obtain a pink solid.

The pink solid and hydrochloride solution in isopropanol (2M, 2 ml) were successively added to a flask, heated to 55° C. and kept for 2 h. The reaction was monitored as being completed by HPLC. The reaction solution was concentrated under reduced pressure to obtain the desired product as a white solid (0.106 g, yield: 96%). $^1$HNMR (DMSO-d$_6$, 400 MHz) δ 9.75 (broad, 3H), 8.99 (broad, 2H), 7.20 (s, 1H), 7.03 (s, 1H), 3.36-3.33 (m, 2H), 3.03-2.98 (m, 3H), 2.32 (s, 3H), 1.80-1.70 (m, 4H), 1.30 (s, 6H).

3. 5-chloro-N$^2$-((2-d-prop-2-yloxy)-5-methyl-4-(piperidin-4-yl) phenyl)-N$^4$-(2-(isopropylsulfonyl) phenyl) pyrimidine-2,4-diamine

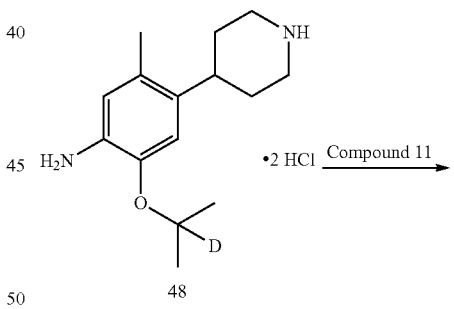

Under the protection of nitrogen, compound 2-((2-d-prop-2-yl) oxyl)-5-methyl-4-(piperidin-4-yl) aniline dihydrochloride (0.107 g, 0.43 mmol), 2,5-dichloro-N-(2-(isopropylsulfonyl) phenyl) pyrimidin-4-amine (0.164 g, 0.473 mmol) and isopropanol (2.5 ml) were added into a flask, warmed to 85° C. and kept 20 h. After cooled to room temperature, into the reaction mixture was added water, and aqueous sodium carbonate solution was added to neutralize the pH to 8.5. The obtained mixture was extracted with ethyl acetate for three times. The organic layers were combined, dried over anhydrous sodium sulfate and concentrated to give a crude product. The crude product was purified by TLC (developing solvent: methanol/dichloromethane=1/9, v/v) to obtain the desired product as a white solid (0.07 g, yield: 30%). MS Calcd.: 558; MS Found: 559 (M+H)$^+$, 581 (M+Na)$^+$. $^1$HNMR (DMSO-d$_6$+D$_2$O, 400 MHz) δ 8.47 (d, J=7.6 Hz, 1H), 8.19 (s, 1H), 7.79-7.77 (dd, J=7.6, 2.0 Hz, 1H), 7.45 (t, J=7.6 Hz, 1H), 7.29 (s, 1H), 7.27 (t, J=7.6 Hz, 1H), 6.89 (s, 1H), 3.45-3.38 (m, 1H), 3.31-3.29 (m, 2H), 3.02-2.92 (m, 3H), 2.33 (s, 3H), 1.79-1.64 (m, 4H), 1.16 (d, 6H), 1.12 (s, 6H).

Example 9

5-chloro-N$^2$-(2-(d$_7$-isopropoxy)-5-methyl-4-(piperidin-4-yl) phenyl)-N$^4$-(2-(isopropylsulfonyl)phenyl) pyrimidine-2,4-diamine

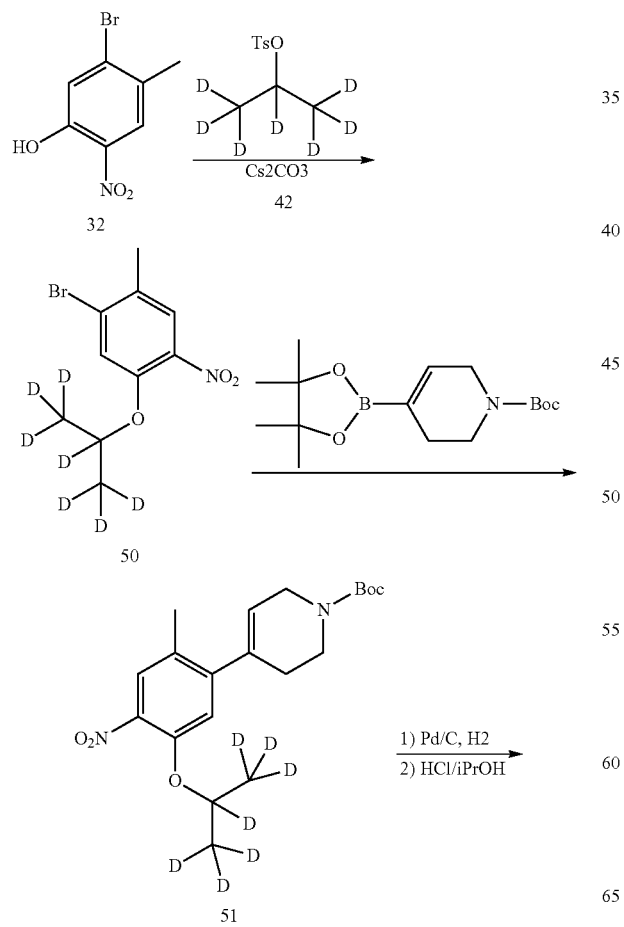

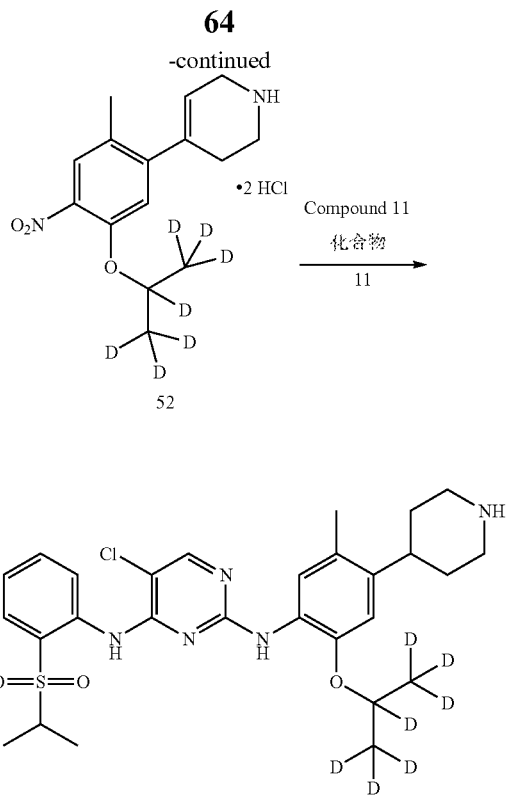

1. Preparation of 1-bromo-5-(d$_7$-isopropoxy)-2-methyl-4-nitrobenzene

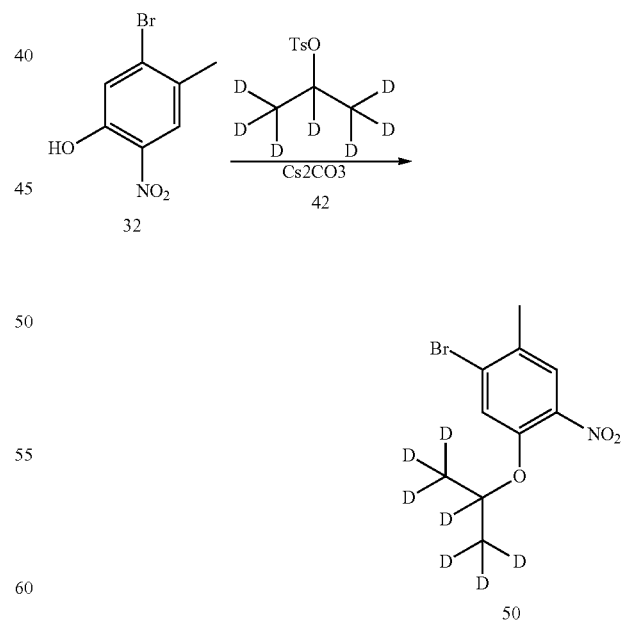

The synthesis was conducted according to step 1 of example 2, and slightly yellowish oily target product was obtained by replacing p-toluene sulfonic acid-2-d-isopropyl with p-toluenesulfonic-d$_7$-isopropyl.

2. Preparation of tert-butyl 4-(5-(d₇-isopropoxy)-2-methyl-4-nitrophenyl)-5,6-dihydropyridine-1 (2H)-carboxylate

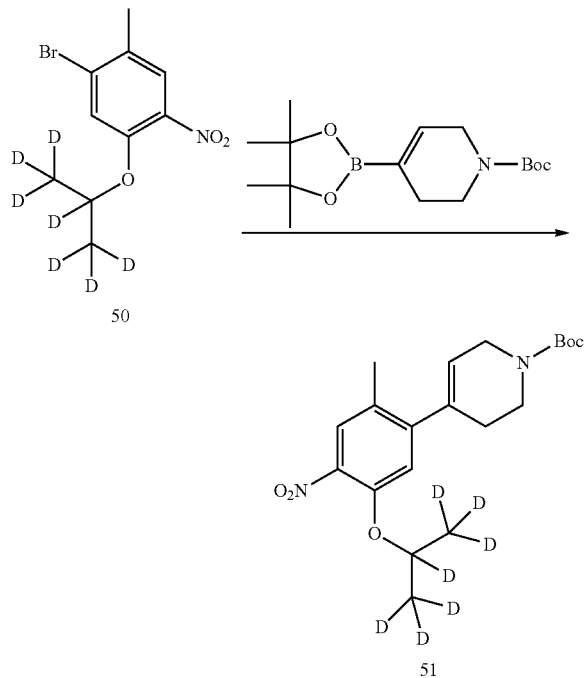

Under the protection of nitrogen, compound 1-bromo-5-(d₇-isopropoxyl)-2-methyl-4-nitrobenzene (0.30 g, 1.07 mmol), 3,6-dihydro-2H-pyridine-1-t-butoxycarbonyl-boronic acid pinacol ester (0.495 g, 1.60 mmol), palladium acetate (22 mg, 0.096 mmol), (i) 4,5-bisdiphenyl phosphine-9,9-dimethyl-xanthene (43 mg, 0.075 mmol), potassium phosphate trihydrate (0.73 g, 3.20 mmol) and tetrahydrofuran (10 ml) were added into a flask, and then heated to 85° C. and kept overnight. The reaction mixture was added with pure water to quench, and extracted with ethyl acetate for three times. The combined organic phase was washed successively with water and brine, dried over anhydrous sodium sulfate, and concentrated to give a crude product. The crude product was separated and purified by TLC to give the desired product as a colorless clear liquid (0.29 g, yield 70%).

3. Preparation of 2-(d₇-isopropoxy)-5-methyl-4-(piperidin-4-yl) aniline dihydrochloride

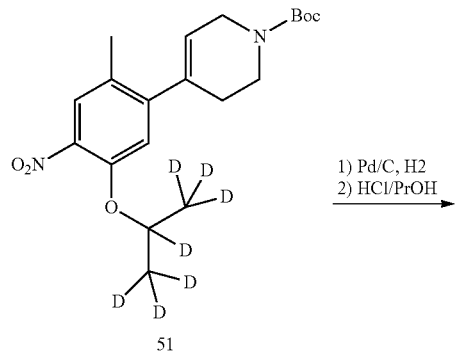

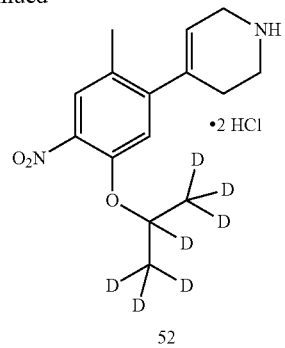

Compound tert-butyl 4-(5-(d₇-isopropoxyl)-2-methyl-4-nitrophenyl)-5,6-dihydropyridine-1 (2H)-carboxylate (0.28 g, 0.73 mmol), palladium on carbon (0.028 g, 50% palladium content) and methanol (10 ml) were added into a flask, and the system was replaced with hydrogen for three times, heated to 45° C. and kept overnight. Palladium on carbon was removed by filtration; and the filtrate was concentrated to obtain a pink solid.

The pink solid and hydrochloride solution in isopropanol (2M, 2 ml) were successively added to a flask, heated to 55° C. and kept for 2 h. The reaction was monitored as being completed by HPLC. The reaction solution was concentrated under reduced pressure to obtain the desired product as a white solid (0.24 g, yield: 98%).

4. 5-chloro-N²-(2-(d₇-isopropoxy)-5-methyl-4-(piperidin-4-yl) phenyl)-N⁴-(2-(isopropylsulfonyl) phenyl) pyrimidine-2,4-diamine

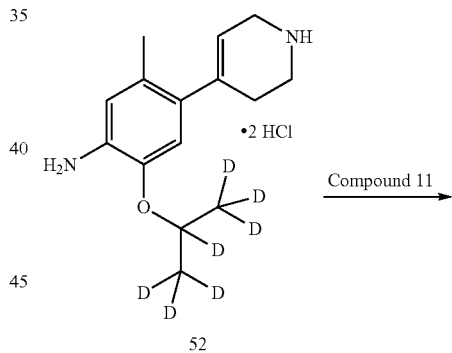

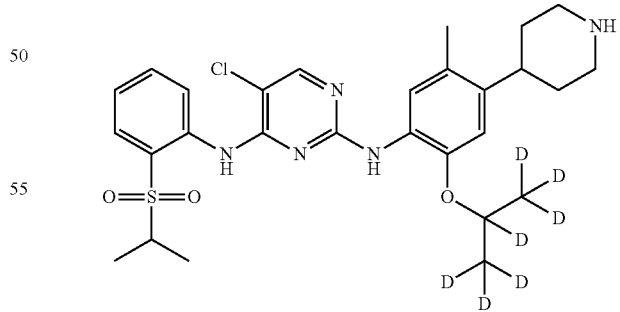

Under the protection of nitrogen, compound 2-(d₇-isopropoxyl)-5-methyl-4-(piperidin-4-yl) aniline dihydrochloride (0.12 g, 0.37 mmol), 2,5-dichloro-N-(2-(isopropylsulfonyl) phenyl) pyrimidin-4-amine (0.14 g, 0.40 mmol) and isopropanol (3 ml) were added into a flask, warmed to 85° C. and kept overnight. After cooled to room temperature, into the reaction mixture was added water, and aqueous sodium carbonate solution was added to neutralize the pH to 8.5. The obtained mixture was extracted with ethyl acetate. The organic layers were combined, dried over anhydrous sodium sulfate and concentrated to give a crude product. The crude product was purified by preparative TLC (developing solvent: methanol/dichloromethane=1/9, v/v) to obtain the desired product as a white solid. MS Calcd.: 564; MS Found: 565 (M+H)$^+$, 587 (M+Na)$^+$.

Example 10

Preparation of 5-chloro-N$^2$-((2-d-prop-2-yloxy)-5-methyl-4-(piperidin-4-yl) phenyl-N$^4$-(2-((2-d-prop-2-yl)sulfonyl)phenyl)pyrimidine-2,4-diamine

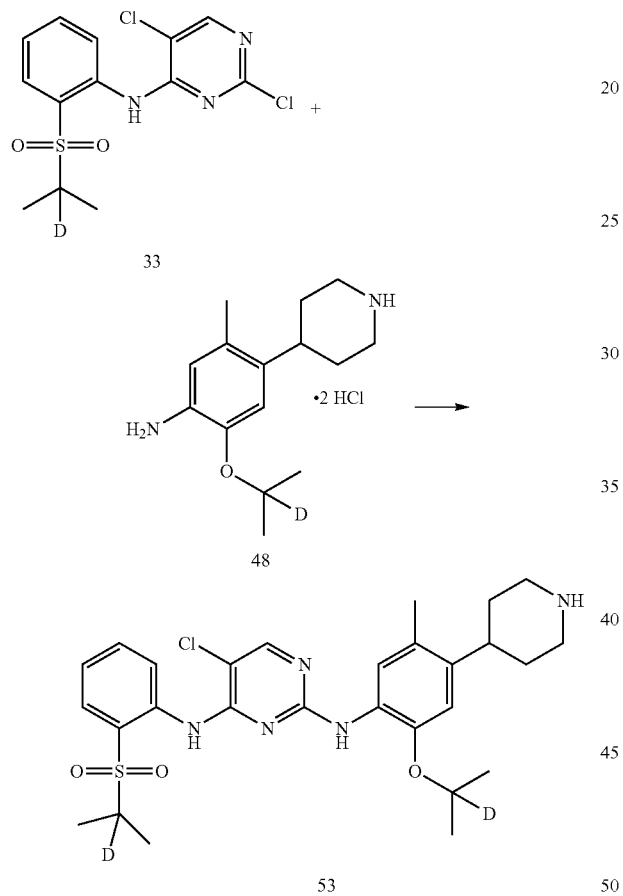

Under the protection of nitrogen, compound 2-((2-d-prop-2-yl) oxyl)-5-methyl-4-(piperidin-4-yl) aniline dihydrochloride (0.055 g, 0.17 mmol), 2,5-dichloro-N-(2-((2-d-prop-2-yl) sulfonyl) phenyl) pyrimidin-4-amine (0.066 g, 0.19 mmol) and isopropanol (3 ml) were added into a flask, warmed to 85° C. and kept overnight. After cooled to room temperature, into the reaction mixture was added with water, and aqueous sodium carbonate solution was added to neutralize the pH to 8.5. The obtained mixture was extracted with ethyl acetate. The organic layers were combined, dried over anhydrous sodium sulfate and concentrated to give a crude product. The crude product was purified by preparative TLC (developing solvent: methanol/dichloromethane=1/9, v/v) to obtain the desired product as a white solid (39 mg, yield: 40%). MS Calcd.: 559; MS Found: 560 (M+H)$^+$, 582 (M+Na)$^+$. $^1$HNMR (DMSO-d$_6$+D$_2$O, 400 MHz) δ 8.49 (d, J=8.0 Hz, 1H), 8.19 (s, 1H), 7.79-7.77 (dd, J=8.0, 1.6 Hz, 1H), 7.45 (m, 1H), 7.29-7.25 (m, 2H), 6.89 (s, 1H), 3.32-3.29 (m, 2H), 3.03-2.93 (m, 3H), 2.33 (s, 3H), 1.79-1.65 (m, 4H), 1.16 (s, 6H), 1.12 (s, 6H).

Example 11

5-chloro-N$^2$-(d$_7$-isopropyloxy-5-methyl-4-(2,2,6,6-d$_4$-piperidin-4-yl)phenyl)-N$^4$-(2-((d$_7$-isopropyl)sulfonyl)phenyl)pyrimidine-2,4-diamine

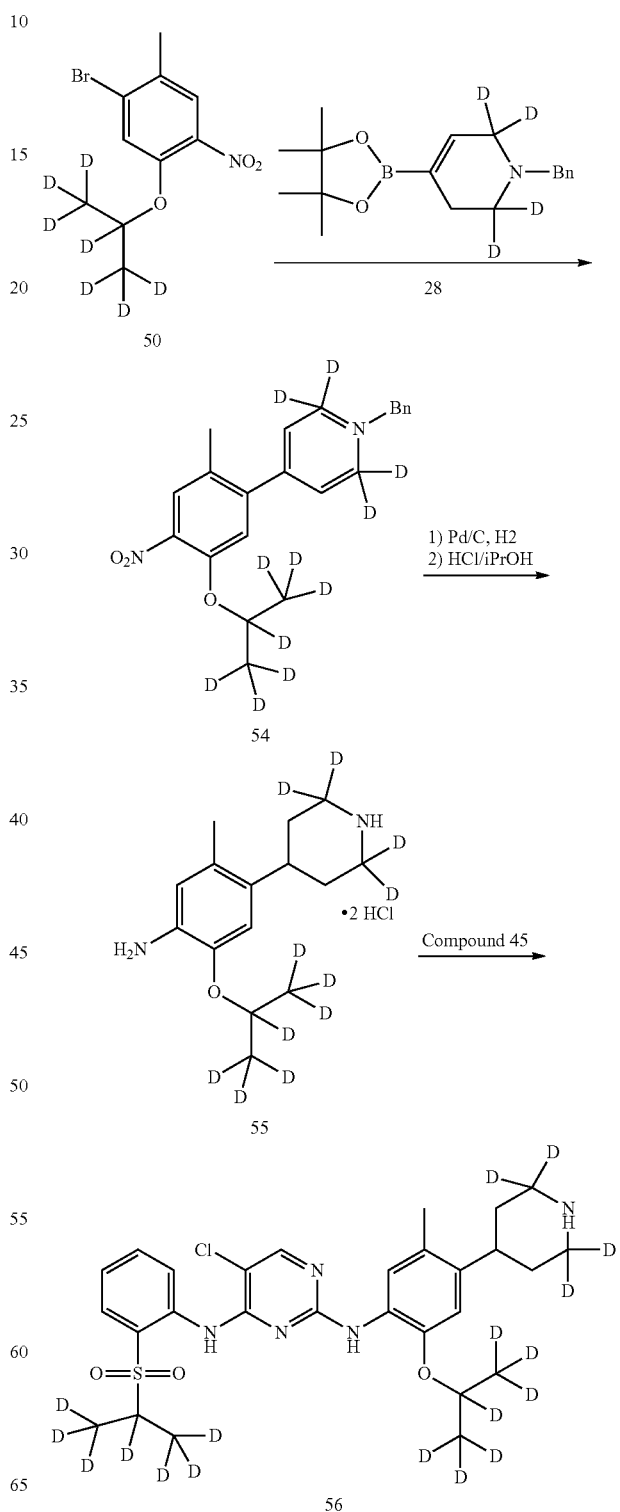

1. Preparation of 1-benzyl-2,2,6,6-d$_4$-4-(5-(d$_7$-isopropoxyl)-2-methyl-4-nitrophenyl)-1,2,3,6-tetrahydropyridine

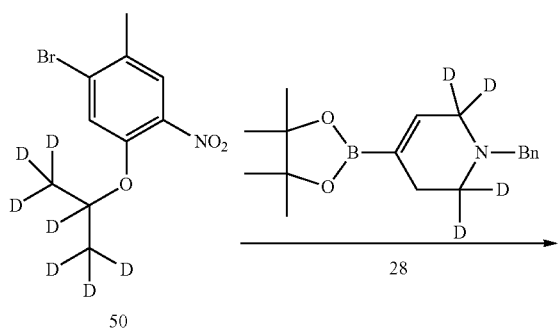

50    28

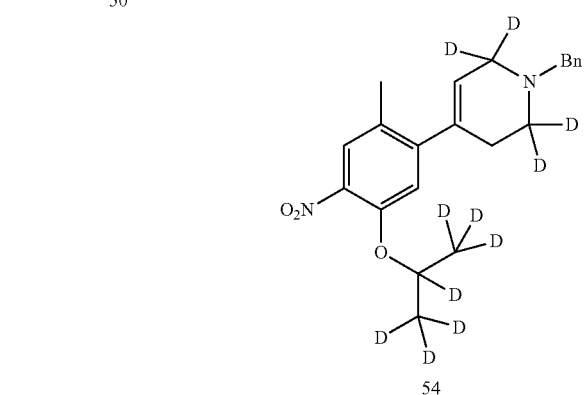

54

Under nitrogen, compound 1-bromo-5-(d$_7$-isopropoxy)-2-methyl-4-nitrobenzene (0.24 g, 0.71 mmol), 1-benzyl-2,2,6,6-d$_4$-4-(4,4,5,5-tetramethyl-1,3,2-dioxaborolan-2-yl)-1,2,3,6-tetrahydropyridine (0.28 g, 0.93 mmol), palladium acetate (15 mg, 0.064 mmol), 4,5-bis-diphenyl phosphine-9,9-dimethyl-xanthene (29 mg, 0.050 mmol), potassium phosphate trihydrate (0.48 g, 2.13 mmol) and tetrahydrofuran (8 ml) were added into a flask, and then heated to 85° C. and kept overnight. The reaction mixture was added with pure water to quench the reaction, and extracted with ethyl acetate. The combined organic phase was washed successively with water and brine, dried over anhydrous sodium sulfate, and concentrated to give a crude product. The crude product was purified by preparative TLC to give the desired product (0.20 g, yield: 75%). MS Calcd.: 377; MS Found: 378 (M+H)$^+$.

2. Preparation of 2-(d$_7$-isopropoxyl)-5-methyl-4-(2,2,6,6-d$_4$-piperidin-4-yl) aniline dihydrochloride

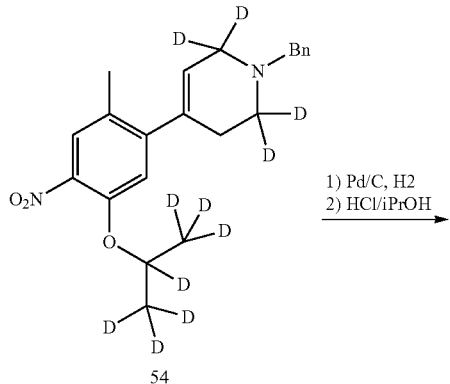

54

1) Pd/C, H2
2) HCl/iPrOH

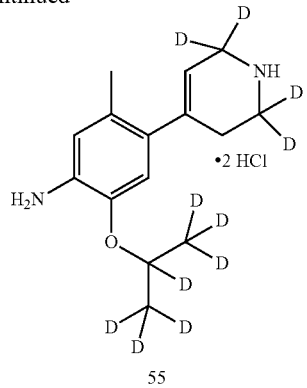

55

Compound 1-benzyl-2,2,6,6-d$_4$-4-(5-(d$_7$-isopropoxyl)-2-methyl-4-nitrophenyl)-1,2,3,6-tetrahydropyridine (0.38 g, 1.01 mmol), palladium on carbon (0.038 g, 50% palladium content) and methanol (10 ml) were added into a flask. The system was replaced with hydrogen for three times, heated to 45° C. and kept for 40 hours. Palladium on carbon was removed by filtration, and the filtrate was concentrated to obtain a gray solid. The obtained gray solid and hydrochloric acid solution in isopropanol (2M, 2 ml) were sequentially added to a flask and stirred for 2 h. The reaction solution was concentrated under reduced pressure to obtain the desired product as a white solid (0.32 g, yield: 95%).

3. 5-chloro-N$^2$-(d$_7$-isopropyloxy)-5-methyl-4-(2,2,6,6-d$_4$-piperidin-4-yl) phenyl)-N$^4$-(2-((d$_7$-isopropyl)sulfonyl)phenyl)pyrimidine-2,4-diamine

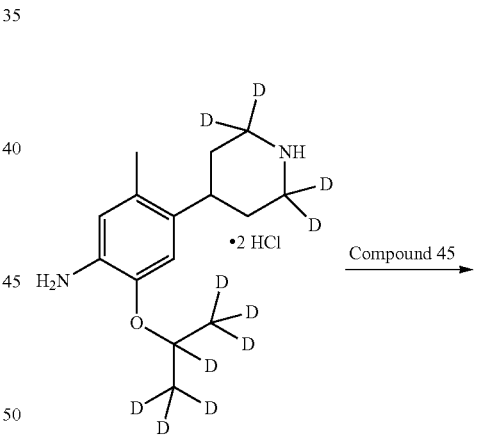

Compound 45

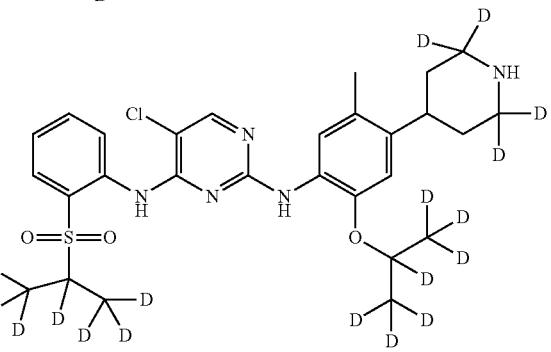

Under the protection of nitrogen, compound 2-(d$_7$-isopropoxyl)-5-methyl-4-(2,2,6,6-d$_4$-piperidin-4-yl) aniline dihydrochloride (0.09 g, 0.27 mmol), 2,5-dichloro-N-(2-(d$_7$-isopropylsulfonyl) phenyl) pyrimidin-4-amine (0.11 g, 0.30 mmol) and isopropanol (3 ml) were added into a flask, warmed to 85° C. and kept overnight. After cooled to room temperature, into the reaction mixture was added water, and aqueous sodium carbonate solution was added to neutralize the pH to 8.5. The obtained mixture was extracted with ethyl acetate. The organic layers were combined, dried over anhydrous sodium sulfate and concentrated to give a crude product. The crude product was purified by preparative TLC (developing solvent: methanol/dichloromethane=1/9, v/v) to obtain the desired product as a white solid (54 mg, yield: 35%).

Example 12

5-chloro-N$^2$-((2-d-prop-2-yloxy)-5-methyl-4-(2,2,6,6-d$_4$-piperidin-4-yl)-6-d-phenyl)-N$^4$-(2-((2-d-prop-2-yl)sulfonyl)phenyl)pyrimidine-2,4-diamine

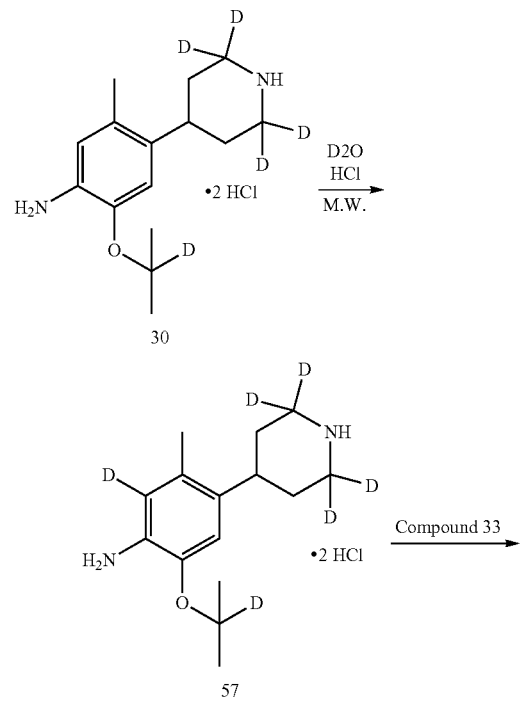

1. Preparation of 2-((2-d-prop-2-yl) oxyl)-5-methyl-4-(2,2,6,6-d$_4$-piperidin-4-yl)-6-d-aniline dihydrochloride

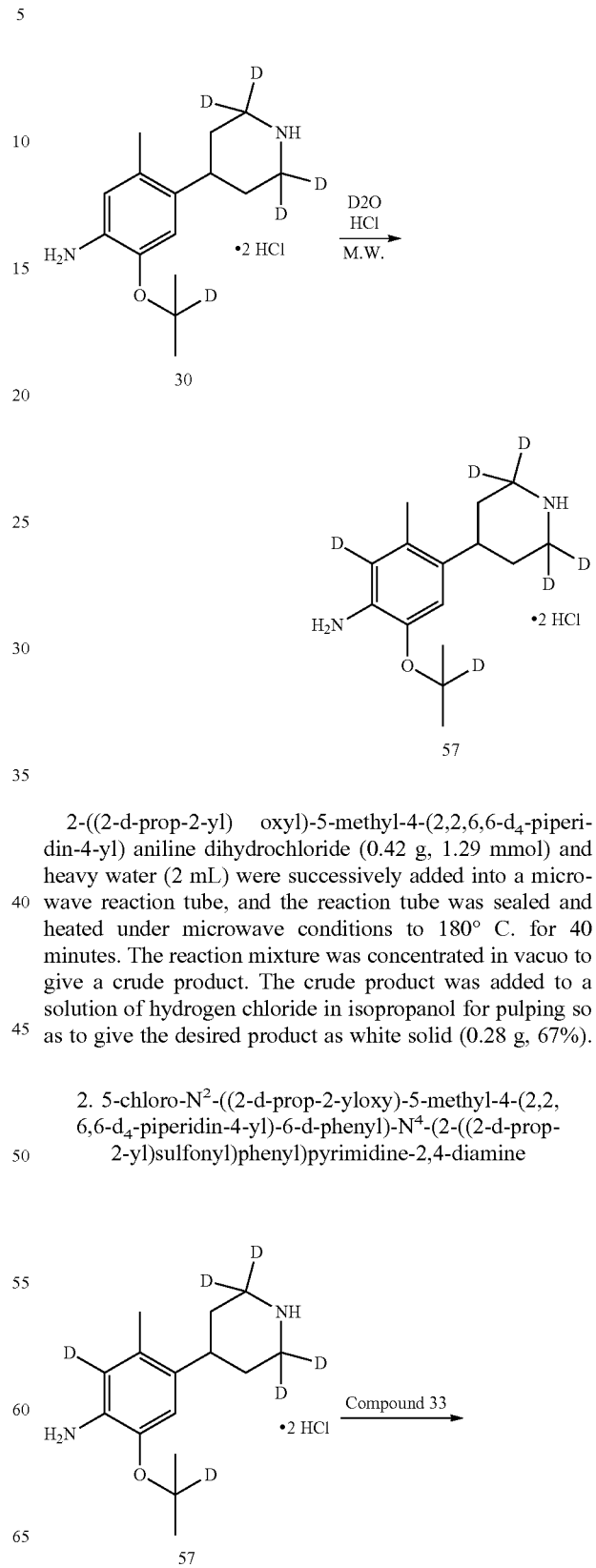

2-((2-d-prop-2-yl) oxyl)-5-methyl-4-(2,2,6,6-d$_4$-piperidin-4-yl) aniline dihydrochloride (0.42 g, 1.29 mmol) and heavy water (2 mL) were successively added into a microwave reaction tube, and the reaction tube was sealed and heated under microwave conditions to 180° C. for 40 minutes. The reaction mixture was concentrated in vacuo to give a crude product. The crude product was added to a solution of hydrogen chloride in isopropanol for pulping so as to give the desired product as white solid (0.28 g, 67%).

2. 5-chloro-N$^2$-((2-d-prop-2-yloxy)-5-methyl-4-(2,2,6,6-d$_4$-piperidin-4-yl)-6-d-phenyl)-N$^4$-(2-((2-d-prop-2-yl)sulfonyl)phenyl)pyrimidine-2,4-diamine

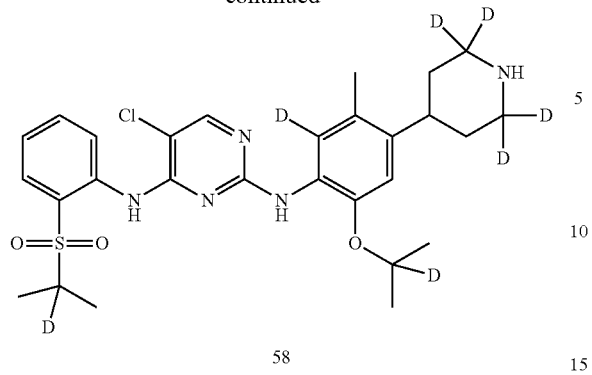

58

Under the protection of nitrogen, compound 2-((2-d-prop-2-yl) oxyl)-5-methyl-4-(2,2,6,6-$d_4$-piperidin-4-yl)-6-d-aniline dihydrochloride (0.087 g, 0.30 mmol), 2,5-dichloro-N-(2-((2-d-prop-2-yl) sulfonyl) phenyl) pyrimidin-4-amine (0.12 g, 0.33 mmol) and isopropanol (3 ml) were added into a flask, warmed to 85° C. and kept overnight. After cooled to room temperature, into the reaction mixture was added pure water, and aqueous sodium carbonate solution was added to neutralize the pH to 8.5. The obtained mixture was extracted with ethyl acetate for three times. The organic layers were combined, dried over anhydrous sodium sulfate and concentrated to give a crude product. The crude product was purified by preparative TLC (developing solvent: methanol/dichloromethane=1/9, v/v) to obtain the desired product as a white solid (0.05 g, yield: 30%). MS Calcd.: 564; MS Found: 565 (M+H)$^+$, 587 (M+Na)$^+$. $^1$HNMR (DMSO-$d_6$+$D_2O$, 400 MHz) δ 8.50 (d, J=7.6 Hz, 1H), 8.22 (s, 1H), 7.80-7.78 (dd, J=7.6, 2.0 Hz, 1H), 7.46 (t, J=7.6 Hz, 1H), 7.30 (s, 1H), 7.26 (t, J=7.6 Hz, 1H), 3.00-2.98 (m, 1H), 2.34 (s, 3H), 1.77-1.65 (m, 4H), 1.23 (s, 6H), 1.12 (s, 6H).

Example 13

5-chloro-N$^2$-((2-d-prop-2-yloxyl)-5-methyl-4-(2,2,6,6-$d_4$-piperidin-4-yl)-6-d-phenyl)-N$^4$-(2-(isopropylsulfonyl)phenyl)pyrimidine-2,4-diamine

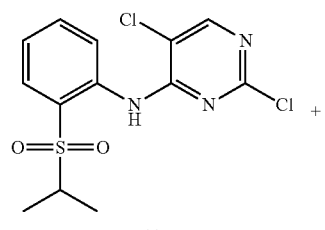

11

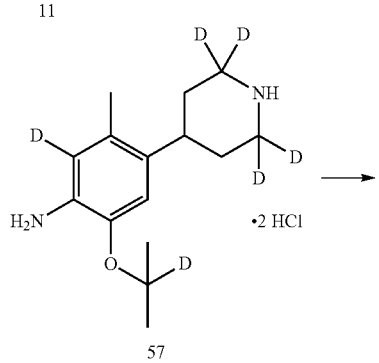

57

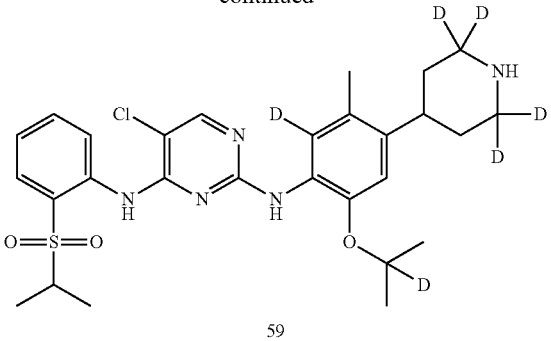

59

Under the protection of nitrogen, compound 2-((2-d-prop-2-yl) oxyl)-5-methyl-4-(2,2,6,6-$d_4$-piperidin-4-yl)-6-d-aniline dihydrochloride (0.087 g, 0.30 mmol), 2,5-dichloro-N-(2-(isopropylsulfonyl) phenyl) pyrimidin-4-amine (0.12 g, 0.33 mmol) and isopropanol (3 ml) were added into a flask, warmed to 85° C. and kept overnight. After cooled to room temperature, into the reaction mixture was added pure water, and aqueous sodium carbonate solution was added to neutralize the pH to 8.5. The obtained mixture was extracted with ethyl acetate for three times. The organic layers were combined, dried over anhydrous sodium sulfate and concentrated to give a crude product. The crude product was purified by preparative TLC (developing solvent: methanol/methylene chloride=1/9, v/v) to obtain the desired product as a white solid (0.06 g, yield: 35%). MS Calcd.: 563; MS Found: 564 (M+H)$^+$, 586 (M+Na)$^+$.

Example 14

5-chloro-N$^2$-(2-isopropoxy-5-methyl-4-(2,2,6,6-$d_4$-piperidin-4-yl)-6-d-phenyl)-N$^4$-(2-((2-d-prop-2-yl)sulfonyl)phenyl)pyrimidine-2,4-diamine

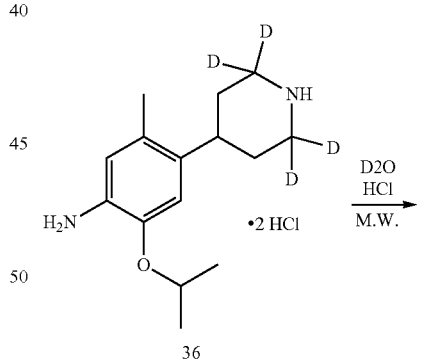

36

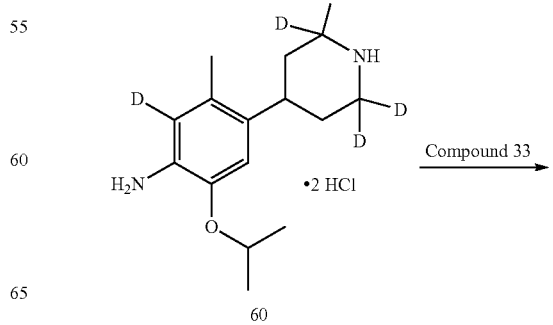

60

-continued

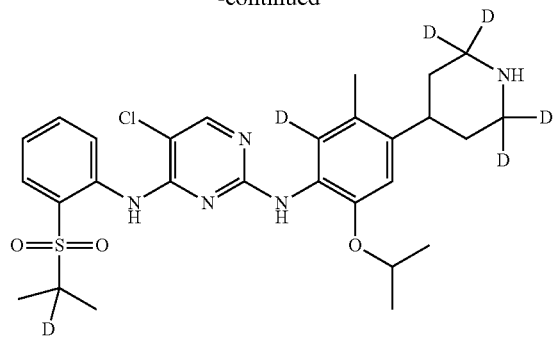

61

1. Preparation of 2-isopropoxy-5-methyl-4-(2,2,6,6-d4-piperidin-4-yl)-6-d-aniline dihydrochloride

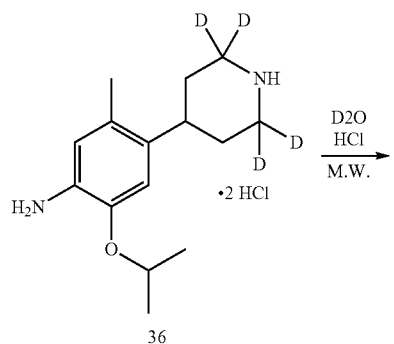

2-isopropoxy-5-methyl-4-(2,2,6,6-d4-piperidin-4-yl) aniline dihydrochloride (0.21 g, 0.65 mmol) and heavy water (2 mL) were successively added into a microwave reaction tube, and the reaction tube was sealed and heated under microwave conditions to 180° C. for 40 minutes. The reaction mixture was concentrated in vacuo to give a crude product. The crude product was added to a solution of hydrogen chloride in isopropanol for pulping so as to give the desired product as white solid (0.15 g, 70%).

2. Preparation of 5-chloro-$N^2$-(2-isopropoxy)-5-methyl-4-(2,2,6,6-d4-piperidin-4-yl)-6-d-phenyl)-$N^4$-(2-((2-d-prop-2-yl)sulfonyl)phenyl)pyrimidine-2,4-diamine

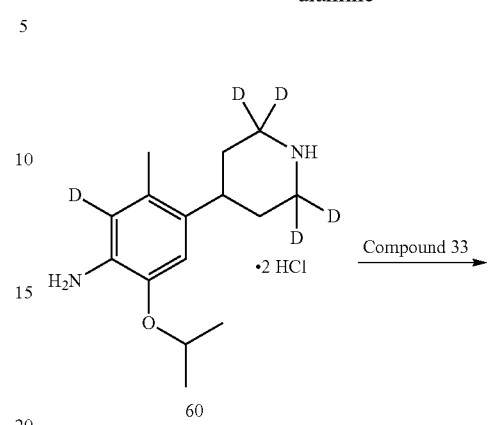

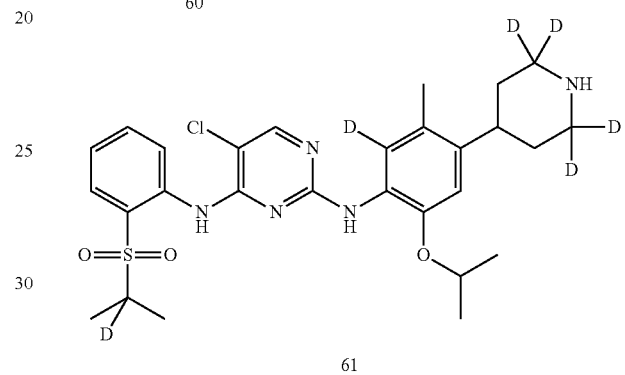

61

Under the protection of nitrogen, compound 2-isopropoxy-5-methyl-4-(2,2,6,6-d4-piperidin-4-yl)-6-d-aniline dihydrochloride (0.070 g, 0.21 mmol), 2,5-dichloro-N-(2-((2-d-prop-2-yl) sulfonyl) phenyl) pyrimidin-4-amine (0.083 g, 0.24 mmol) and isopropanol (3 ml) were added into a flask, warmed to 85° C. and kept overnight. After cooled to room temperature, into the reaction mixture was added water, and aqueous sodium carbonate solution was added to neutralize the pH to 8.5. The obtained mixture was extracted with ethyl acetate. The organic layers were combined, dried over anhydrous sodium sulfate and concentrated to give a crude product. The crude product was purified by preparative TLC (developing solvent: methanol/methylene chloride=1/9, v/v) to obtain the desired product as a white solid (0.045 g, yield: 38%). MS Calcd.: 563; MS Found: 564 (M+H)+, 586 (M+Na)+.

Example 15

5-chloro-$N^2$-((2-d-prop-2-yloxy)-5-methyl-4-(d9-piperidin-4-yl)-phenyl)-$N^4$-(2-(isopropylsulfonyl)phenyl)pyrimidine-2,4-diamine

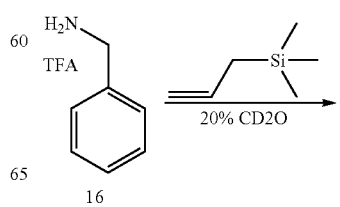

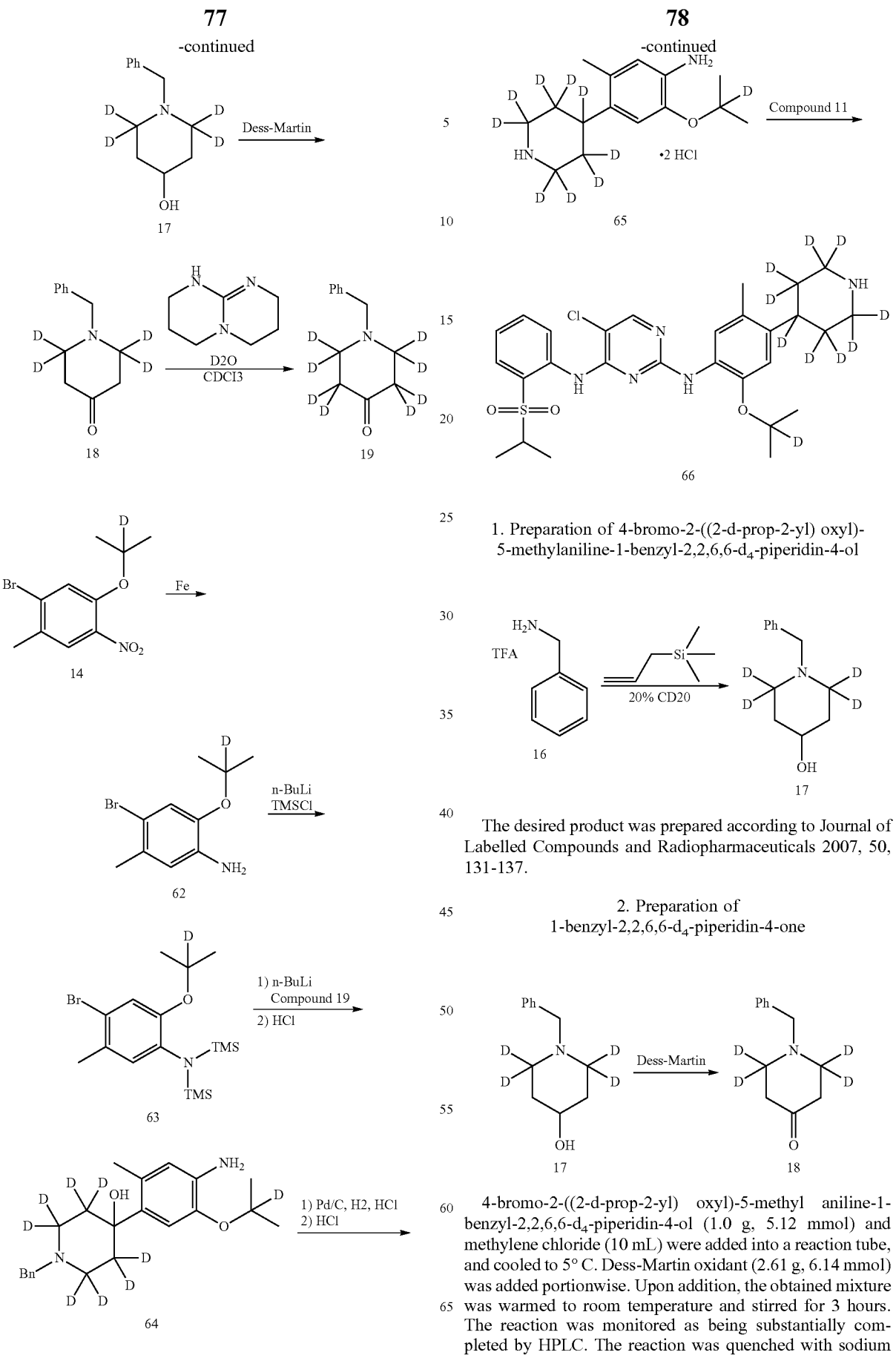

1. Preparation of 4-bromo-2-((2-d-prop-2-yl) oxyl)-5-methylaniline-1-benzyl-2,2,6,6-d4-piperidin-4-ol The desired product was prepared according to Journal of Labelled Compounds and Radiopharmaceuticals 2007, 50, 131-137.

2. Preparation of 1-benzyl-2,2,6,6-d4-piperidin-4-one 4-bromo-2-((2-d-prop-2-yl) oxyl)-5-methyl aniline-1-benzyl-2,2,6,6-d4-piperidin-4-ol (1.0 g, 5.12 mmol) and methylene chloride (10 mL) were added into a reaction tube, and cooled to 5° C. Dess-Martin oxidant (2.61 g, 6.14 mmol) was added portionwise. Upon addition, the obtained mixture was warmed to room temperature and stirred for 3 hours. The reaction was monitored as being substantially completed by HPLC. The reaction was quenched with sodium

3. Preparation of 1-benzyl-2,2,3,3,5,5,6,6-d$_8$-piperidin-4-one

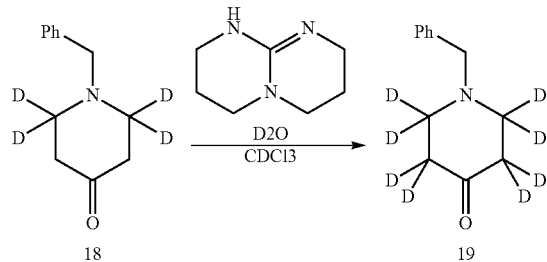

1-benzyl-2,2,6,6-d$_4$-piperidin-4-one (0.26 g) was dissolved in deuteriochloroform (CDCl$_3$, 5 mL, 99.9% D) and heavy water (5 mL, 99.9% D), and 1,5,7-triazabicyclo[4.4.0]dec-5 ene was added. The obtained mixture was sealed and stirred at room temperature overnight. The reaction was monitored with HNMR until the hydrogen peak of ortho to carbonyl was invisible. Diluted hydrochloric acid was added to quench the reaction. The obtained mixture was extracted with ethyl acetate, and dried over anhydrous sodium sulfate. The crude product was obtained by concentrating under reduced pressure, and was purified by preparative TLC to give the desired product. $^1$HNMR (CDCl$_3$, 400 MHz) δ 7.39-7.31 (m, 5H), 3.61 (s, 2H).

4. Preparation of 4-bromo-2-((2-d-prop-2-yl) oxyl)-5-methylaniline

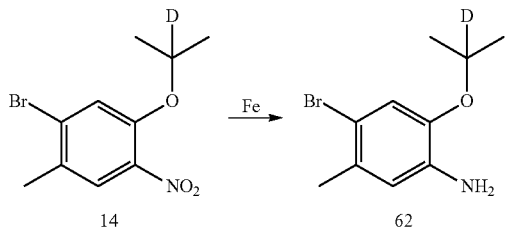

Under the protection of nitrogen, compounds 1-bromo-5-(2-d-prop-2-yloxyl)-2-methyl-4-nitrobenzene (100 mg, 0.36 mmol), reduced iron powders (306 mg, 5.5 mmol) and acetic acid (2 mL) were added into a flask, and stirred overnight at room temperature. Water and ethyl acetate were added into the reaction mixture successively, the aqueous phase was separated and extracted with ethyl acetate, the combined organic phase was washed with sodium bicarbonate solution, dried over anhydrous magnesium sulfate, filtered, and the filtrate was concentrated in vacuo with rotary evaporator to give a crude product, and purified by TLC preparative plate chromatography (developing solvent: petroleum ether/ethyl acetate=1/10, v/v) to give the desired product as a brown solid (70 mg, 78% yield). $^1$HNMR (DMSO-d6, 400 MHz) δ 6.82 (s, 1H), 6.78 (s, 1H), 4.70 (s, 2H), 2.17 (s, 3H), 1.26 (s, 6H).

5. Preparation of 4-(4-amino-5-((2-d-prop-2-yl) oxyl)-2-methylphenyl)-1-benzyl-(d$_8$-piperidin)-4-ol

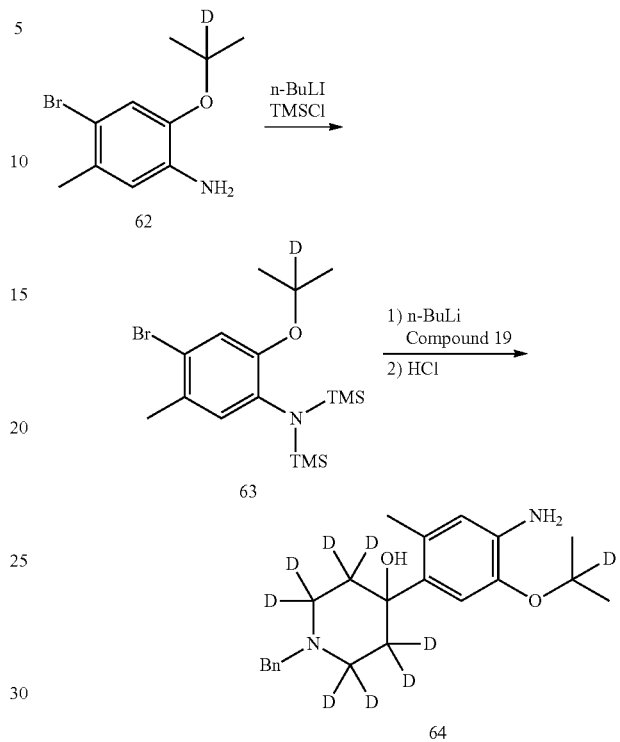

Under the protection of nitrogen, compound 4-bromo-2-((2-d-prop-2-yl) oxyl)-5-methylaniline (0.37 g, 1.5 mmol) and tetrahydrofuran (5 mL) were added into a flask, and cooled to below −78° C. Then n-butyllithium in n-hexane (1.6M, 0.94 mL, 1.5 mmol) was added, and stirred for 5 minutes. The temperature was kept below −70° C., and trimethyl chlorosilane (0.16 g, 1.5 mmol) was added dropwise, and stirred for 20 minutes. The temperature was kept below −70° C., and n-butyllithium in n-hexane (0.94M, 3.12 mL, 1.5 mmol) and trimethyl chlorosilane (0.18 g, 1.7 mmol) were added. Upon addition, the temperature was gradually raised to −5° C. N-hexane and aqueous sodium bicarbonate were added, and the aqueous layer was separated and extracted with n-hexane. The organic layers were combined, washed with water and brine successively, dried over anhydrous sodium sulfate and concentrated under reduced pressure to give crude compound 63, which was used in the next step reaction without being purified.

Under the protection of nitrogen, crude product compound 63 was solved in anhydrous tetrahydrofuran (3 mL), and cooled to below −78° C. N-butyllithium in n-hexane (1.6M, 0.94 mL, 1.5 mmol) was added and stirred for 60 minutes. The temperature was kept below −70° C., and 1-benzyl-2,2,3,3,5,5,6,6-d$_8$-piperidine-4-one (0.25 g, 1.3 mmol) in tetrahydrofuran (1 mL) was added dropwise. Upon addition, the obtained mixture was slowly warmed to room temperature and stirred overnight. Concentrated hydrochloric acid (0.5 mL) was added, and stirred overnight. The obtained mixture was neutralized with saturated sodium bicarbonate solution to neutrality, and Then extracted with ethyl acetate. The organic layers were combined, washed with sodium bicarbonate and water successively, dried over anhydrous sodium sulfate, and concentrated in vacuo to give a crude product. The crude product was purified by preparative TLC to give the desired product.

6. Preparation of 2-((2-d-prop-2-yl) oxyl)-5-methyl-4-(d₉-piperidin-4-yl) aniline dihydrochloride

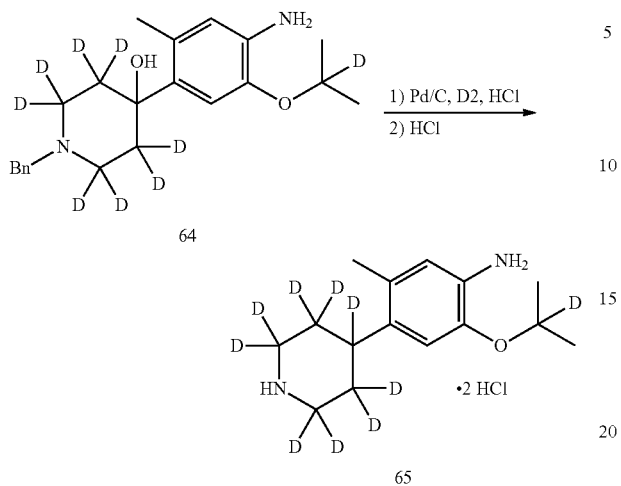

Compound 4-(4-amino-5-((2-d-prop-2-yl) oxy)-2-methylphenyl)-1-benzyl-(d₈-piperidine)-4-ol (0.125 g, 0.34 mmol), palladium on carbon (15 mg, 50% Pd), concentrated hydrochloric acid, and deuterated methanol (CD₃OD, 8 ml) were added into a flask, and the system was replaced with deuterium for three times, heated to 40° C. for 8 hours under 50 psi. Palladium on carbon was removed by filtration; and the filtrate was concentrated to obtain a gray solid. The obtained gray solid and hydrochloric acid solution in isopropanol (2M, 2 ml) were sequentially added into a flask and stirred for 2 h. The reaction solution was concentrated under reduced pressure to obtain the desired product as a white solid.

7. Preparation of 5-chloro-N²-((2-d-prop-2-yloxy)-5-methyl-4-(d₉-piperidin-4-yl)-phenyl)-N⁴-(2-(isopropylsulfonyl) phenyl) pyrimidine-2,4-diamine

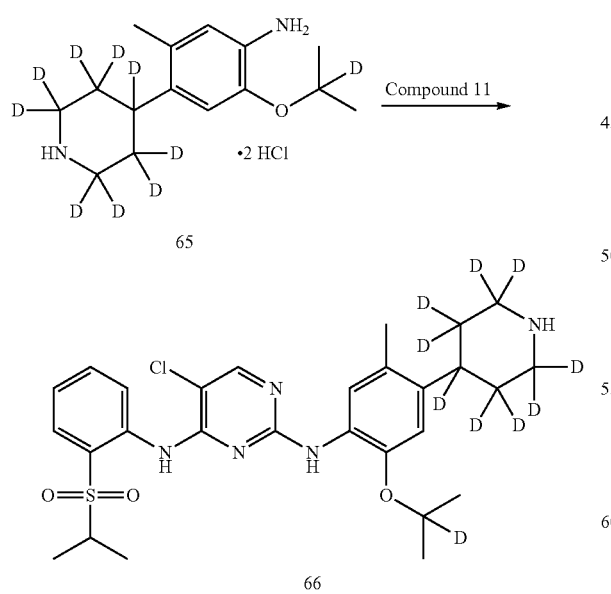

Under the protection of nitrogen, compound 2-((2-d-prop-2-yl) oxy)-5-methyl-4-(d₉-piperidin-4-yl) aniline dihydrochloride (0.050 g, 0.15 mmol), 2,5-dichloro-N-(2-(isopropylsulfonyl) phenyl) pyrimidin-4-amine (0.063 g, 0.18 mmol) and isopropanol (2 ml) were added into a flask, warmed to 85° C. and kept overnight. After cooled to room temperature, into the reaction mixture was added pure water to quench the reaction, and aqueous sodium carbonate solution was added to neutralize the pH to 8.5. The obtained mixture was extracted with ethyl acetate. The organic layers were combined, dried over anhydrous sodium sulfate and concentrated to give a crude product. The crude product was separated by preparative TLC (developing solvent: methanol/methylene chloride=1/9, v/v) to obtain the desired product as a white solid. MS Calcd.: 567; MS Found: 568 (M+H)⁺, 590 (M+Na)⁺.

Example 16

5-chloro-N²-N²-d-prop-2-yloxy)-5-methyl-4-(2,2,3,3,5,5,6,6-d₈-piperidin-4-yl)-phenyl)-N⁴-(2-(isopropylsulfonyl)phenyl)pyrimidine-2,4-diamine

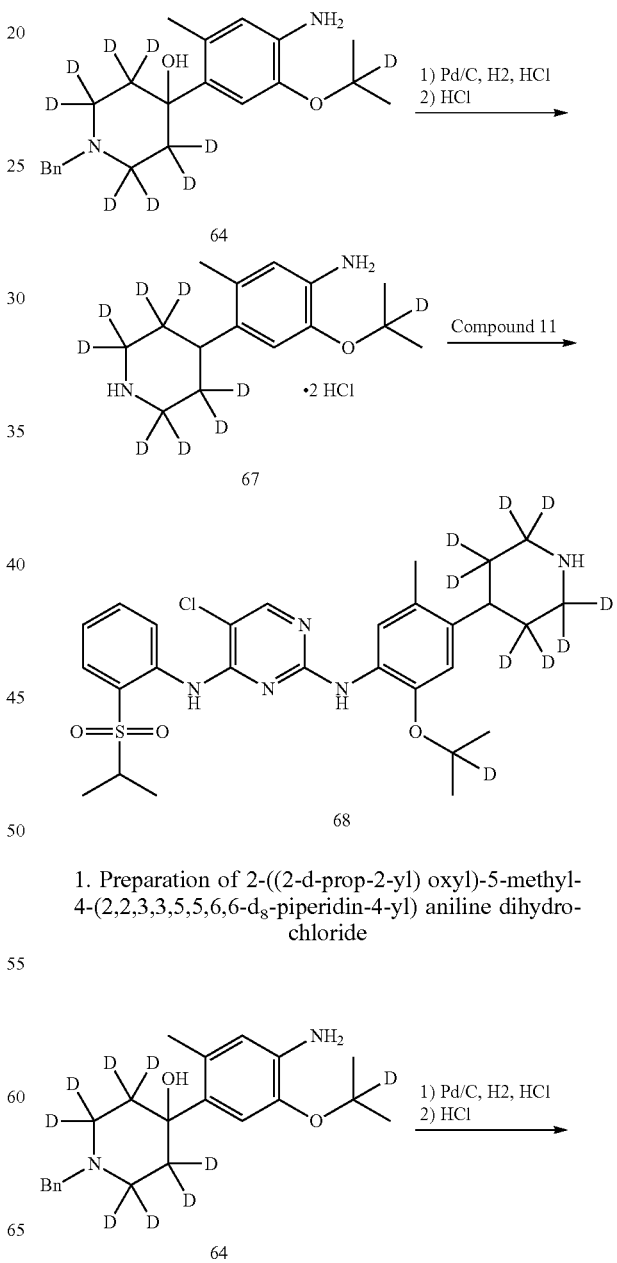

1. Preparation of 2-((2-d-prop-2-yl) oxyl)-5-methyl-4-(2,2,3,3,5,5,6,6-d₈-piperidin-4-yl) aniline dihydrochloride

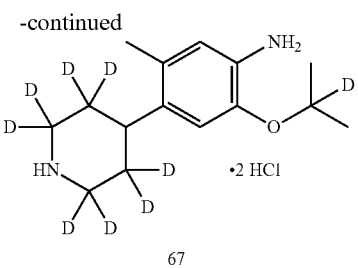

67

Compound 4-(4-amino-5-((2-d-prop-2-yl) oxy)-2-methylphenyl)-1-benzyl-(d$_8$-piperidine)-4-ol (0.125 g, 0.34 mmol), palladium on carbon (15 mg, 50% Pd), concentrated hydrochloric acid, and methanol (8 ml) were added into a flask, and the system was replaced with hydrogen for three times, was heated to 40° C. for 8 hours under 50 psi. Palladium on carbon was removed by filtration, and the filtrate was concentrated to obtain a gray solid. The obtained gray solid and hydrochloric acid solution in isopropanol (2M, 2 ml) were sequentially added to a flask and stirred for 2 h. The reaction solution was concentrated under reduced pressure to obtain the desired product as a white solid.

2. Preparation of 5-chloro-N$^2$-((2-d-prop-2-yloxy)-5-methyl-4-(2,2,3,3,5,5,6,6-d$_8$-piperidin-4-yl)-phenyl)-N$^4$-(2-(isopropylsulfonyl)phenyl)pyrimidine-2,4-diamine

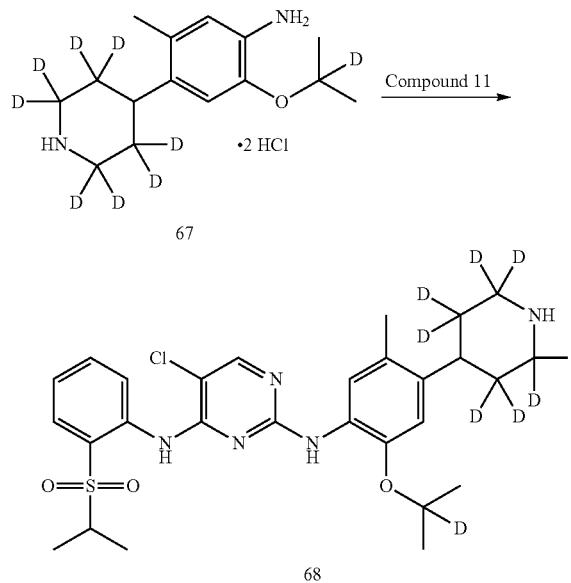

Under the protection of nitrogen, compound 2-((2-d-prop-2-yl) oxy)-5-methyl-4-(2,2,3,3,5,5,6,6-d$_8$-piperidin-4-yl) aniline dihydrochloride (0.045 g, 0.14 mmol), 2,5-dichloro-N-(2-(isopropylsulfonyl) phenyl) pyrimidin-4-amine (0.058 g, 0.17 mmol) and isopropanol (2 ml) were added into a reaction tube, warmed to 85° C. and kept overnight. After cooled to room temperature, into the reaction mixture was added pure water to quench the reaction, and aqueous sodium carbonate solution was added to neutralize the pH to 8.5. The obtained mixture was extracted with ethyl acetate. The organic layers were combined, dried over anhydrous sodium sulfate and concentrated to give a crude product. The crude product was purified by preparative TLC (developing solvent: methanol/dichloromethane=1/9, v/v) to obtain the desired product as a white solid. MS Calcd.: 566; MS Found: 567 (M+H)$^+$, 589 (M+Na)$^+$.

Example 17

Pharmacokinetic Evaluation in Rats 8 male Sprague-Dawley rats (7-8 weeks old, approximately 200 g body weight), were divided into two groups with four in each group. A dose of 5 mg/kg of (a) the control compound 5-chloro-N$^2$-(2-isopropoxy-5-methyl-4-(piperidin-4-yl) phenyl)-N$^4$-(2-(isopropylsulfonyl) phenyl) pyrimidine-2,4-diamine (CERITINIB) and (b) test compound: compounds prepared in example 1-16 was orally administrated for each time, and the difference in pharmacokinetics between the two groups was compared.

Rats were fed with standard feed, and given water ad libitum, and started to fast 16 hours before the test. The drug is dissolved with PEG400 and dimethylsulfoxide. Orbital blood collection was conducted at 0.083 hour, 0.25 hour, 0.5 hour, 1 hour, 2 hour, 4 hour, 6 hour, 8 hour, 12 hour and 24 hour after administration.

The rats are shortly anesthesiaed by inhalation of ether; 300 pt of orbital blood was collected into a test tube. There were 30 μL 1% heparin saline solutions in the test tube. Before use, test tubes were dried overnight at 60° C. After the blood sample was collected at the subsequent time point, rats were anesthetized with ether and euthanatized.

After the blood sample was collected, the tubes were gently inverted at least 5 times immediately to ensure adequate mixing, and placed on ice. At 4° C., blood samples were centrifuged at 5000 rpm for 5 minutes to separate plasma and red blood cells. 100 μL of plasma was pipetted into a clean plastic centrifuge tube, and the name of compounds and the time point was indicated. Plasma was stored at −80° C. before performing the analysis. The concentration of compound of the invention in plasma was determined with LC-MS/MS. The pharmacokinetic parameters were calculated based on the plasma concentration of compound in each animal at different time points.

Figure 2:
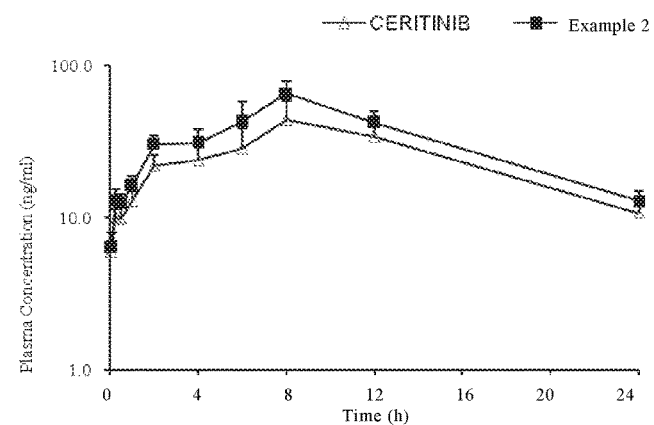
FIG. 2 is a curve of time vs the plasma concentration of compound in male rats respectively administered with 5 mg/kg of control compound CERITINIB and compound of Example 2 by gavage.
Figure 3:
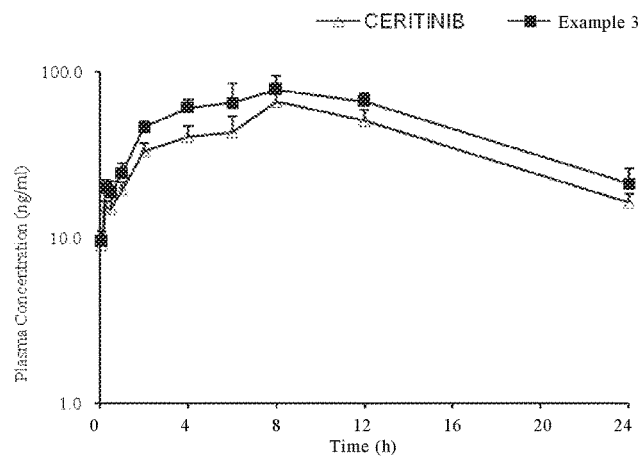
FIG. 3 is a curve of time vs the plasma concentration of compound in male rats respectively administered with 5 mg/kg of control compound CERITINIB and compound of Example 3 by gavage.
Figure 4:
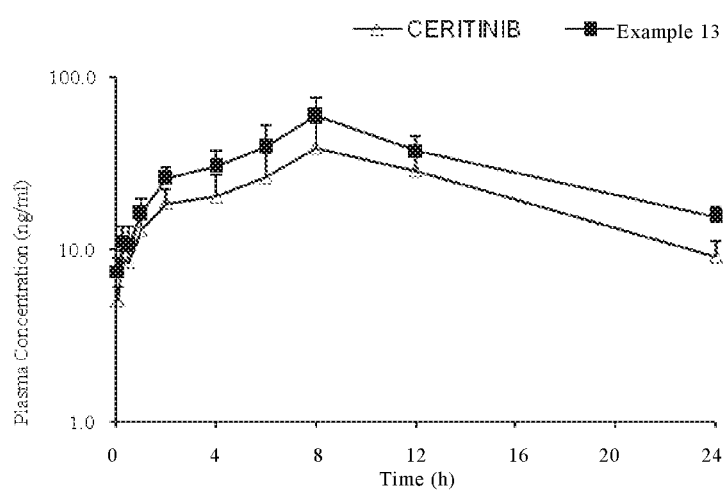
FIG. 4 is a curve of time vs the plasma concentration of compound in male rats respectively administered with 5 mg/kg of control compound CERITINIB and compound of Example 13 by gavage.

It can be seen from the results that, compared with the control compound, compounds of the present invention are of better pharmacokinetics in animals (higher plasma concentrations (e.g., FIGS. 1 to 4), longer half-life and lower clearance rate), which has better pharmacodynamic and therapeutic effects.

Example 18

In Vitro Pharmacodynamics Evaluation to ALK Kinases of the Compounds of the Invention The determination of IC$_{50}$ of the inhibiting effect to kinase ALK 96-well plates was coated under 37° C. with coating buffer (125 μl/well) overnight, and coating buffer was polypeptide substrate [Poly (4:1 Glu, Tyr) Peptide, available from SignalChem] containing 2.5 μg/well ALK kinase in PBS. Then, each well was washed with 200 μl of buffer (PBS containing 0.05% Tween 80), and placed at 37° C. for at least 2 hours to dryness.

Serial diluted test compounds in different concentrations (compounds prepared in any one of Examples 1 to 16, dissolved in DMSO) were added to each well in 5/well, followed by addition of kinase buffer (25 mM Hepes, pH 7.5, 5 mM MnCl$_2$, 5 mM MgCl$_2$), 0.3 mM ATP, and 100 ng/well recombinant human ALK (Abnova Corporation), to a total volume of 100 μl each well. After kept at 30° C. for 15 minutes, the reaction mixture was removed, and washed with 200 μl of wash buffer (PBS containing 0.05% Tween 80) for 5 times.

100 μl/well of mouse anti-phosphotyrosine monoclonal antibody (clone 4G10, purchased from EMD Millipore Corporation) were used in the detection of phosphorylated peptide substrate.

Monoclonal antibody was diluted at 1:500 with PBS containing 4% bovine serum albumin. After incubated at room temperature for 30 minutes, the antibody solution was removed, and each well was washed with 200 μl of wash buffer (PBS containing 0.05% Tween 80) for 5 times.

100 μl/well of secondary antibody (anti-mouse IgG) was added. The secondary antibody was diluted at 1:1000 with PBS containing 4% bovine serum albumin, incubated for 30 minutes at room temperature; and the wells were washed again as said above.

100 μl/well of TMB substrate solution was used for color development, and the same volume of 0.18 M $H_2SO_4$ was added to terminate the color development. Finally, the absorbance at 450 nm or 490 nm was read, and the $IC_{50}$ was calculated.

The results are shown in table 1. It can be seen that the compounds of the present invention have excellent inhibitory activity and selectivity to ALK kinase.

TABLE 1

| Compound | ALK kinase inhibitory activity ($IC_{50}$) |
|---|---|
| Example 1 | <5 nM |
| Example 2 | <5 nM |
| Example 3 | <5 nM |
| Example 4 | <5 nM |
| Example 5 | <5 nM |
| Example 6 | <5 nM |
| Example 7 | <5 nM |
| Example 8 | <5 nM |
| Example 9 | <5 nM |
| Example 10 | <5 nM |
| Example 11 | <5 nM |
| Example 12 | <5 nM |
| Example 13 | <5 nM |
| Example 14 | <5 nM |
| Example 15 | <5 nM |
| Example 16 | <5 nM |

Example 19

Pharmaceutical Composition

| Compound (Example 1-16) | 10 g |
|---|---|
| Starch | 140 g |
| Microcrystalline cellulose | 60 g |

The above substances were mixed by conventional methods, then filled into general gelatin capsules to obtain 100 capsules.

All literatures mentioned in the present application are incorporated herein by reference, as though each one is individually incorporated by reference. Additionally, it should be understood that after reading the above teachings, those skilled in the art can make various changes and modifications to the present invention. These equivalents also fall within the scope defined by the appended claims.

The invention claimed is:

1. A deuterated diaminopyrimidine compound, or a crystal form, pharmaceutically acceptable salt, hydrate or solvate thereof of formula (I):

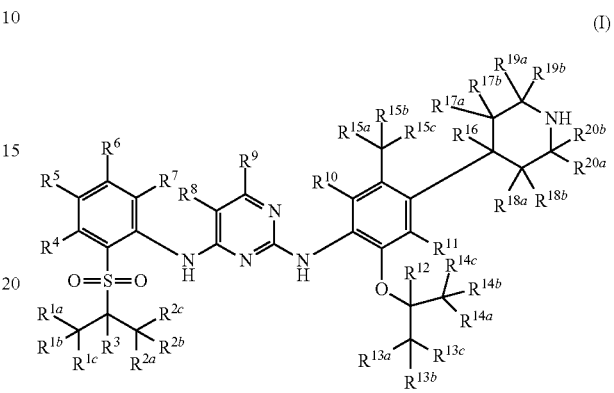

wherein:
$R^{1a}$, $R^{1b}$, $R^{1c}$, $R^{2a}$, $R^{2b}$, $R^{2c}$, $R^3$, $R^4$, $R^5$, $R^6$, $R^7$, $R^9$, $R^{10}$, $R^{11}$, $R^{12}$, $R^{13a}$, $R^{13b}$, $R^{13c}$, $R^{14a}$, $R^{14b}$, $R^{14c}$, $R^{15a}$, $R^{15b}$, $R^{15c}$, $R^{16}$, $R^{17a}$, $R^{17b}$, $R^{18a}$, $R^{18b}$, $R^{19a}$, $R^{19b}$, $R^{20a}$ and $R^{20b}$ are independently hydrogen, deuterium or halogen;

$R^8$ is halogen;

with the proviso that at least four of $R^{1a}$, $R^{1b}$, $R^{1c}$, $R^{2a}$, $R^{2b}$, $R^{2c}$, $R^3$, $R^{12}$, $R^{13a}$, $R^{13b}$, $R^{13c}$, $R^{14a}$, $R^{14b}$, $R^{14c}$, $R^{19a}$, $R^{19b}$, $R^{20a}$ and $R^{20b}$ are deuterium.

2. The compound of claim 1, wherein $R^{1a}$, $R^{1b}$, $R^{1c}$, $R^{2a}$, $R^{2b}$, $R^{2c}$ and $R^3$ are independently deuterium or hydrogen.

3. The compound of claim 1, wherein $R^{12}$, $R^{13a}$, $R^{13b}$, $R^{13c}$, $R^{14a}$, $R^{14b}$ and $R^{14c}$ are independently deuterium or hydrogen.

4. The compound of claim 1, wherein $R^{15a}$, $R^{15b}$ and $R^{15c}$ are independently deuterium or hydrogen.

5. The compound of claim 1, wherein $R^{16}$, $R^{17a}$, $R^{17b}$, $R^{18a}$, $R^{18b}$, $R^{19a}$, $R^{19b}$, $R^{20a}$ and $R^{20b}$ are independently deuterium or hydrogen.

6. The compound of claim 1, wherein $R^8$ is chlorine.

7. The compound of claim 1, wherein $R^{12}$ is deuterium.

8. The compound of claim 1, wherein $R^{19a}$, $R^{19b}$, $R^{20a}$ and $R^{20b}$ are deuterium.

9. The compound of claim 1, wherein the compound is selected from the group consisting of:

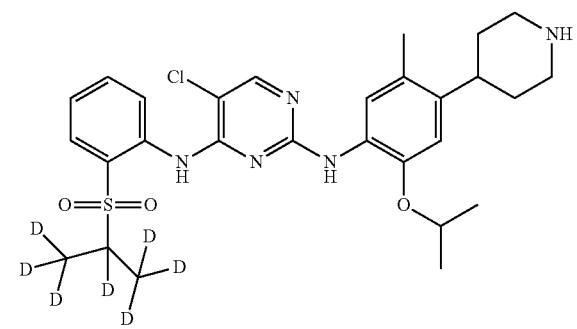

87
-continued
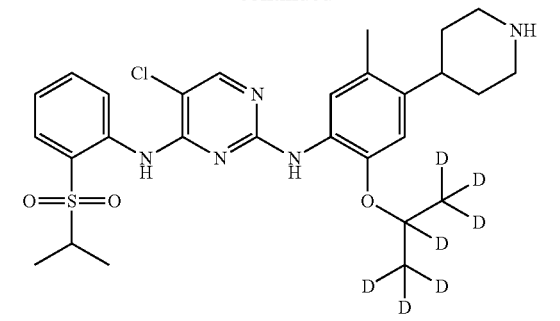
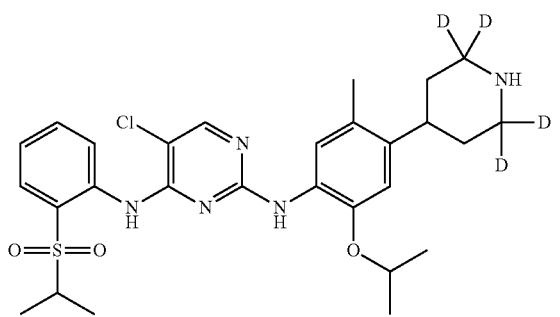
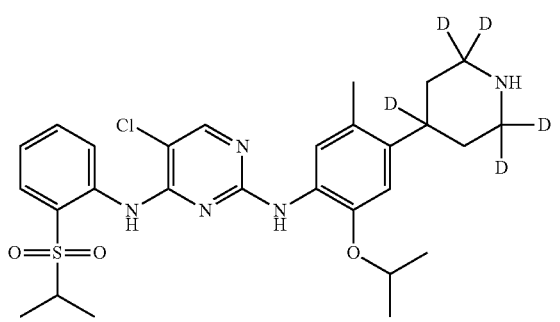
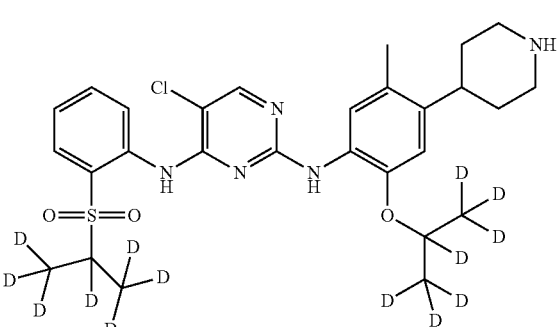
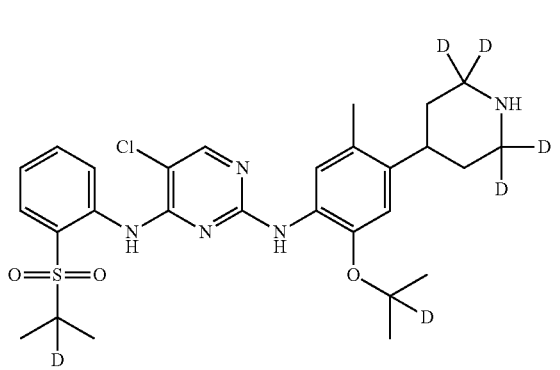
88
-continued
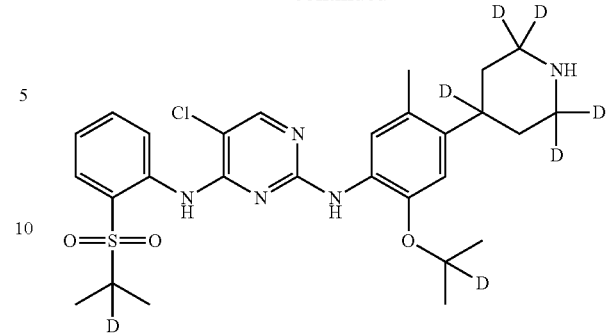
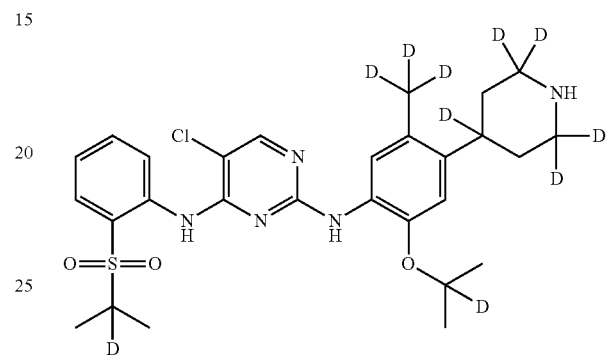
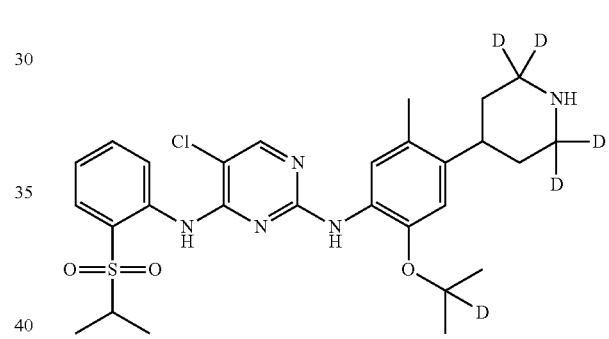
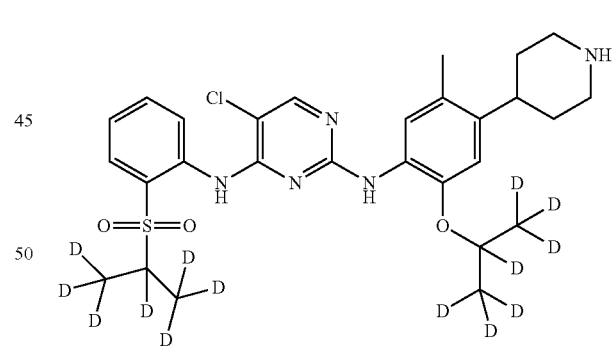
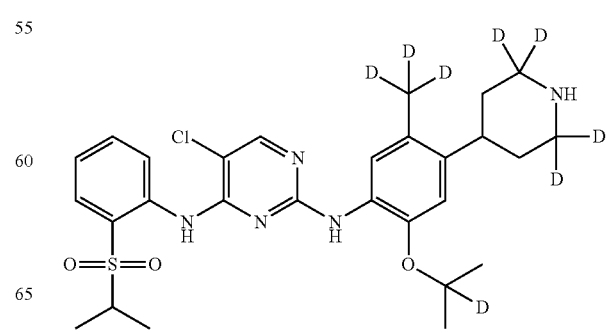

89
-continued
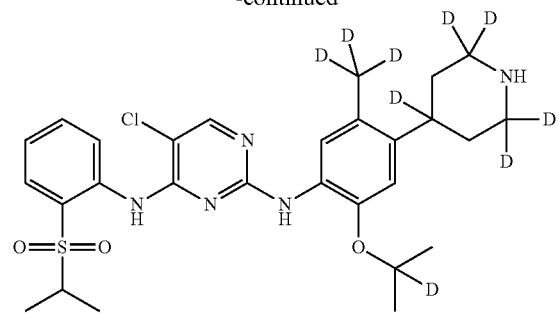
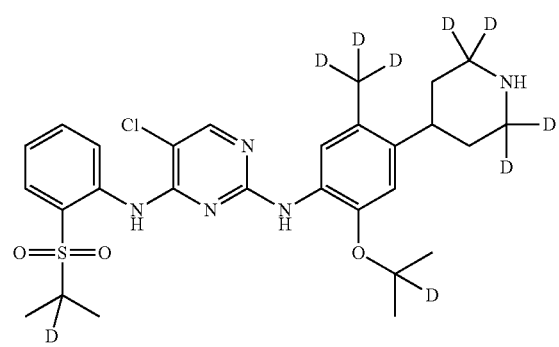
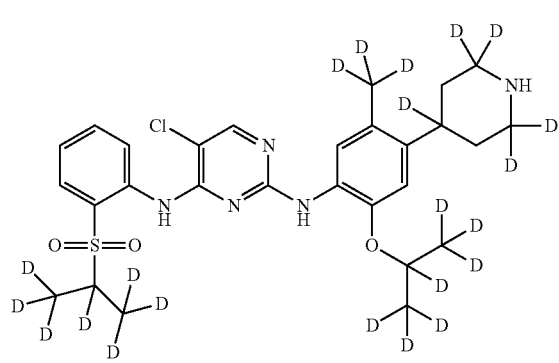
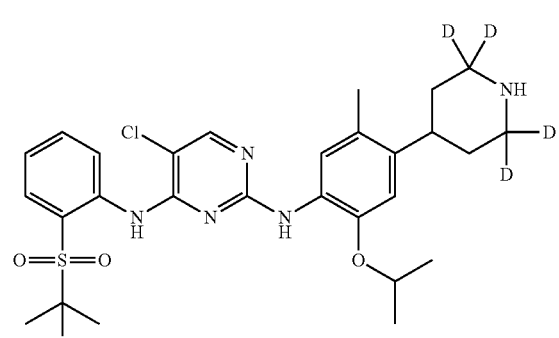
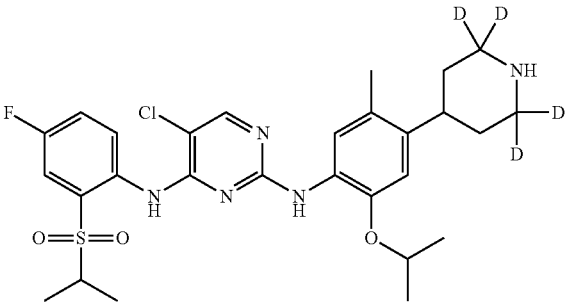
90
-continued
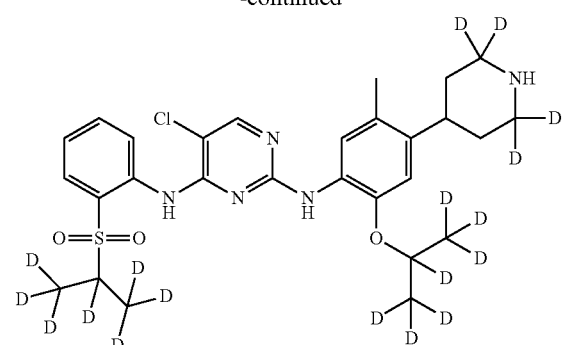
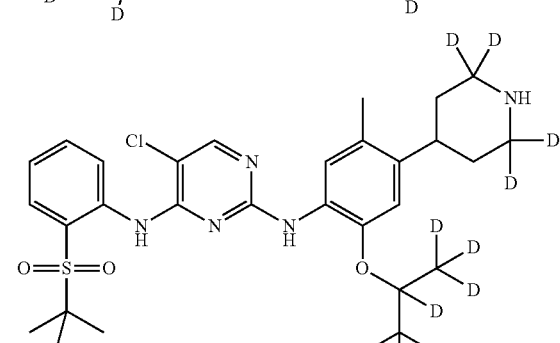
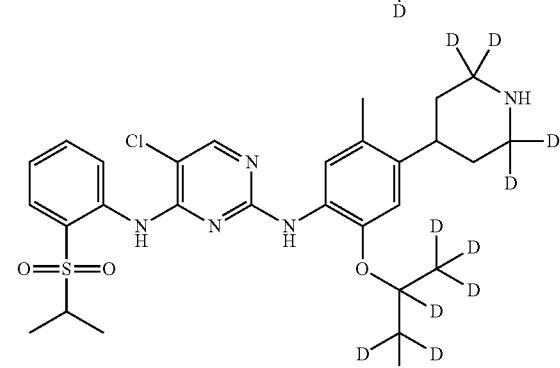
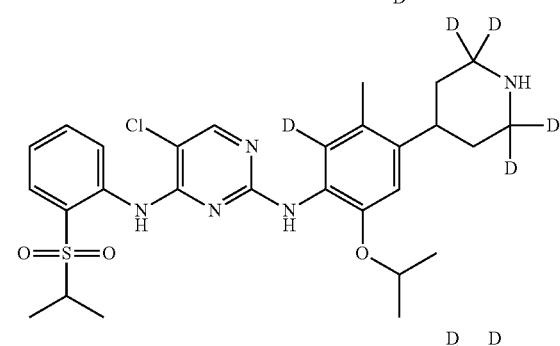
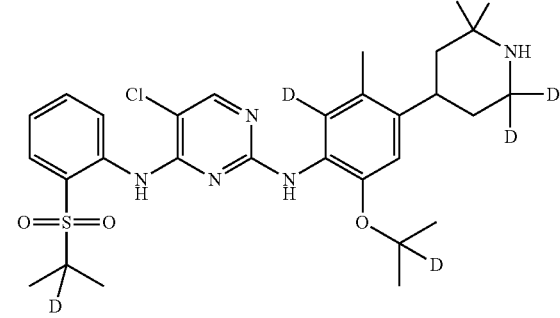

-continued

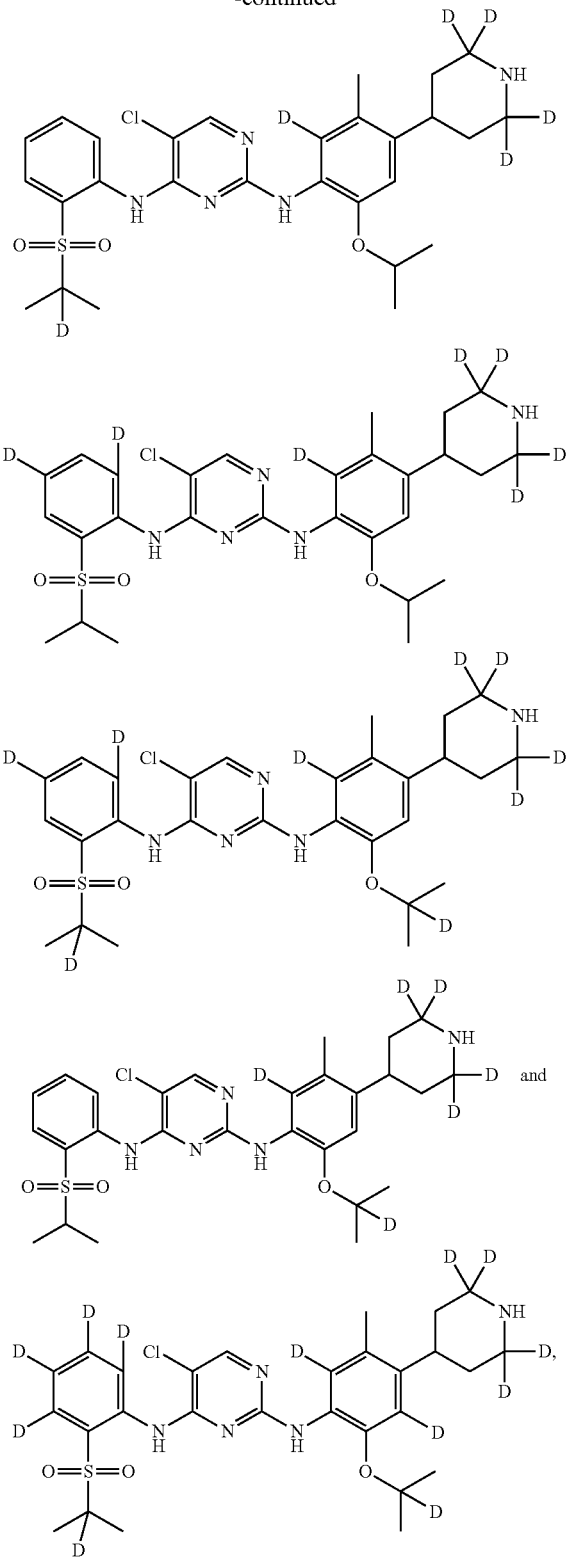

or a pharmaceutically acceptable salt thereof.

10. A method of preparing a pharmaceutical composition, comprising the following step: mixing the compound of claim 1, or a crystal form, pharmaceutically acceptable salt, hydrate or solvate thereof and a pharmaceutically acceptable carrier, thereby forming the pharmaceutical composition.

11. A pharmaceutical composition, comprising a pharmaceutically acceptable carrier and the compound of claim 1, or a crystal form, pharmaceutically acceptable salt, hydrate or solvate thereof.

12. The pharmaceutical composition of claim 11, wherein the pharmaceutical composition further comprises other therapeutic medicines, and the other therapeutic medicines are medicines for treating cancers, cell proliferative disorders, cardiovascular diseases, inflammations, infections, autoimmune diseases, viral diseases, or metabolic disorders.

13. A preparation method for the compound of claim 1, or a crystal form, pharmaceutically acceptable salt, hydrate or solvate thereof, comprising the following step:
reacting compound A6 with compound XV, thereby obtaining compound I;

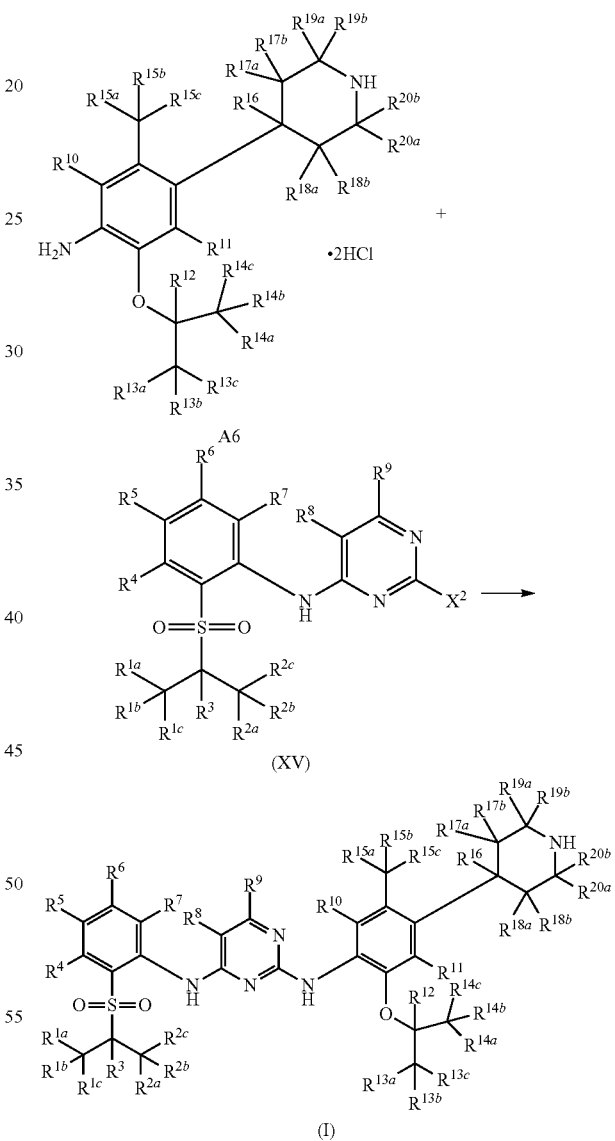

wherein $X^2$ is F, Cl, Br, or I.

14. The preparation method of claim 13, wherein compound A6 is obtained by the following steps:
(a) Reacting compound IV with compound A4, thus obtaining compound A5;
(b) Conducting reduction reaction and deprotection reaction to compound A5, thereby obtaining compound A6;

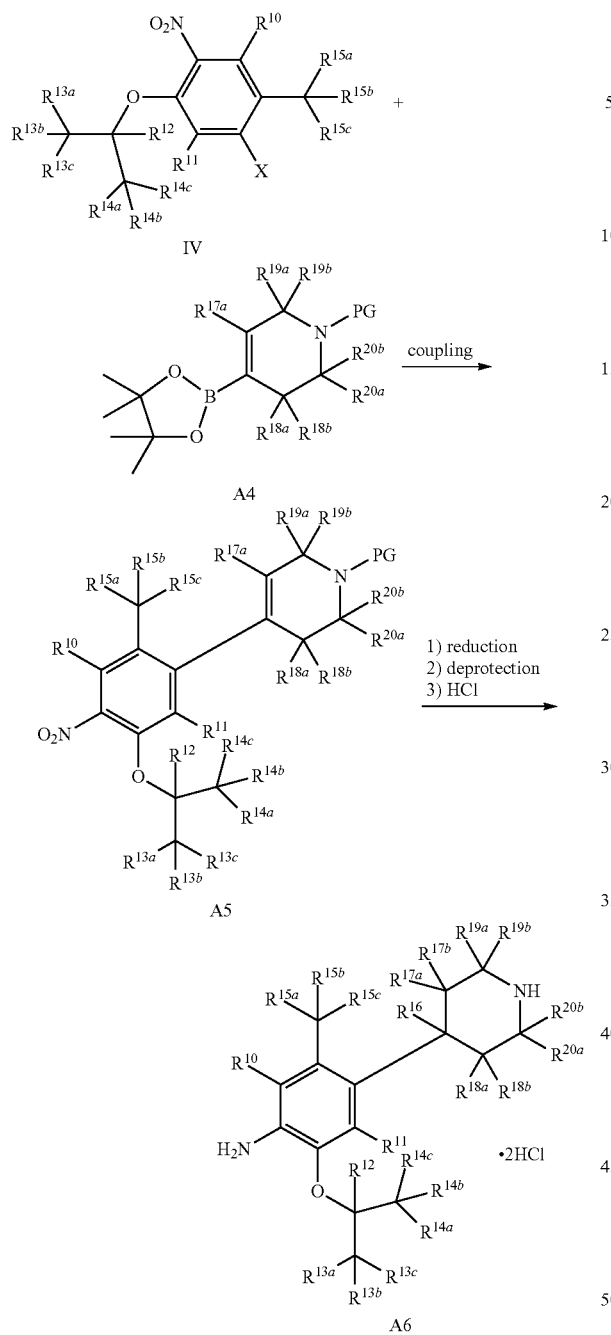
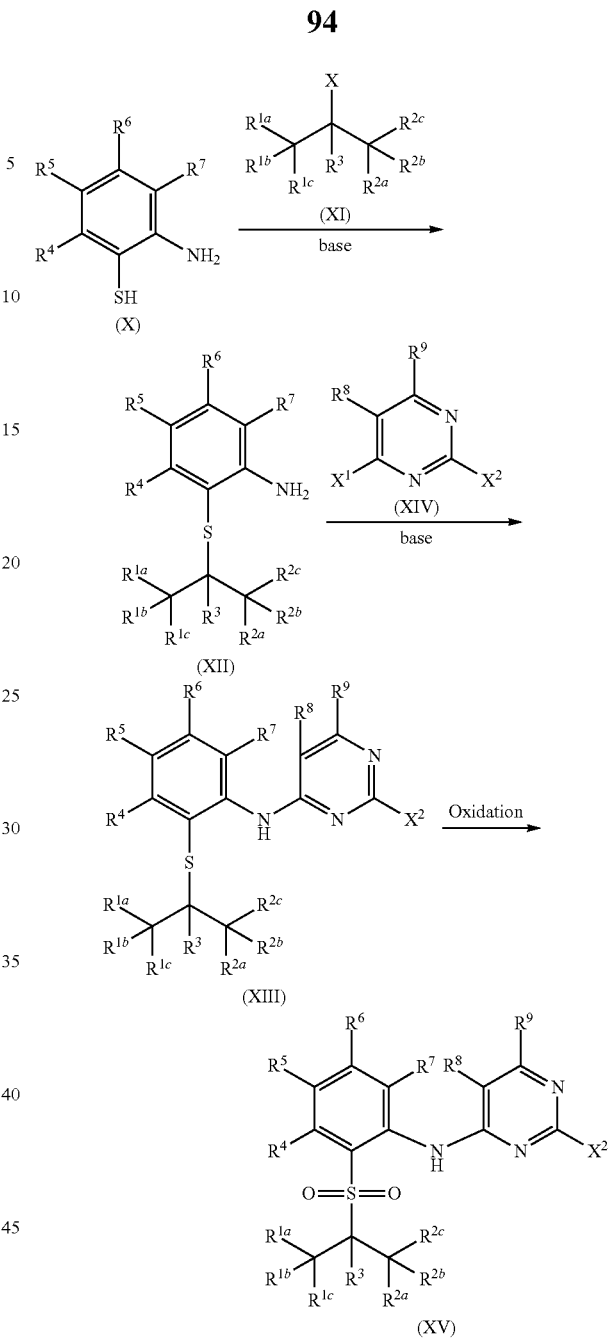

wherein X is F, Cl, Br, I, or OTf; and PG is an amino protection group.

15. The preparation method of claim 13, wherein compound XV is obtained by the following steps:
(a) Reacting compound X with compound XI, thereby obtaining compound XII;
(b) Reacting compound XII with compound XIV, thereby obtaining compound XIII;
(c) Conducting oxidation reaction to compound XIII, thereby obtaining compound XV;

wherein X, $X^1$, and $X^2$ are F, Cl, Br, I, OTs, OMs, or OTf.

16. A method of treating a cancer selected from the group consisting of lung cancer, head and neck cancer, breast cancer, prostate cancer, esophageal cancer, colorectal cancer, colon cancer, nasopharyngeal cancer, uterine cancer, pancreatic cancer, lymphoma, leukemia, osteosarcoma, melanoma, kidney cancer, stomach cancer, liver cancer, bladder cancer, and thyroid cancer in a subject in need thereof, the method comprising administering to the subject the pharmaceutical composition of claim 11.

* * * * *